(12) United States Patent
Lipp et al.

(10) Patent No.: US 11,667,722 B2
(45) Date of Patent: Jun. 6, 2023

(54) ANTIBODY THAT BINDS CD269 (BCMA) SUITABLE FOR USE IN THE TREATMENT OF PLASMA CELL DISEASES SUCH AS MULTIPLE MYELOMA AND AUTOIMMUNE DISEASES

(71) Applicant: Max-Delbrück-Centrum für Molekulare Medizin in der Helmholtz-Gemeinschaft, Berlin (DE)

(72) Inventors: Martin Lipp, Glienicke (DE); Felix Oden, Berlin (DE); Uta Höpken, Berlin (DE); Gerd Müller, Berlin (DE); Oliver Daumke, Berlin (DE); Stephen Marino, Berlin (DE); Daniel Olal, Berlin (DE)

(73) Assignee: Max-Delbrück-Centrum für Molekulare Medizin in der Helmholtz-Gemeinschaft, Berlin (DE)

( * ) Notice: Subject to any disclaimer, the term of this patent is extended or adjusted under 35 U.S.C. 154(b) by 339 days.

(21) Appl. No.: 16/923,726

(22) Filed: Jul. 8, 2020

(65) Prior Publication Data

US 2020/0369778 A1 Nov. 26, 2020

Related U.S. Application Data

(62) Division of application No. 16/219,379, filed on Dec. 13, 2018, now Pat. No. 10,745,486, which is a division of application No. 14/440,165, filed as application No. PCT/EP2013/072857 on Nov. 1, 2013, now Pat. No. 10,189,906.

(30) Foreign Application Priority Data

| Nov. 1, 2012 | (EP) | 12190970 |
| Feb. 21, 2013 | (EP) | 13156091 |
| Aug. 15, 2013 | (EP) | 13180548 |

(51) Int. Cl.

| C07K 16/28 | (2006.01) |
| A61K 47/68 | (2017.01) |
| A61P 35/00 | (2006.01) |
| C07K 16/30 | (2006.01) |
| A61K 39/00 | (2006.01) |
| A61K 39/395 | (2006.01) |

(52) U.S. Cl.
CPC ...... *C07K 16/2878* (2013.01); *A61K 47/6867* (2017.08); *A61P 35/00* (2018.01); *C07K 16/3061* (2013.01); *A61K 39/395* (2013.01); *A61K 2039/505* (2013.01); *C07K 2317/24* (2013.01); *C07K 2317/34* (2013.01); *C07K 2317/41* (2013.01); *C07K 2317/55* (2013.01); *C07K 2317/565* (2013.01); *C07K 2317/73* (2013.01); *C07K 2317/76* (2013.01); *C07K 2317/92* (2013.01)

(58) Field of Classification Search
CPC ............ C07K 16/2878; C07K 16/3061; C07K 2317/24; C07K 2317/34; C07K 2317/41; C07K 2317/55; C07K 2317/565; C07K 2317/73; C07K 2317/76; C07K 2317/92; A61K 47/6867; A61K 39/395; A61K 2039/505; A61P 35/00
See application file for complete search history.

(56) References Cited

U.S. PATENT DOCUMENTS

| 2003/0012783 A1 | 1/2003 | Kindsvogel |
| 2019/0112382 A1 | 4/2019 | Oden et al. |

FOREIGN PATENT DOCUMENTS

| WO | WO 02/066516 A2 | 8/2002 |
| WO | WO 2010/104949 A2 | 9/2010 |
| WO | WO 2010/115553 A1 | 10/2010 |
| WO | WO 2012/066058 A1 | 5/2012 |
| WO | WO 2012/143498 A1 | 10/2012 |
| WO | WO 2012/163805 A1 | 12/2012 |

OTHER PUBLICATIONS

Bendig 1995 "Humanization of rodent monoclonal antibodies by CDR grafting" *Methods: A Companion to Methods in Enzymology* 8: 83-93.
Colman 1994 "Effects of amino acid sequence changes on antibody-antigen interactions" *Research in Immunology* 145: 33-36.
Dissertation 2014 "Generation of an antibody targeting B cell maturation antigen for the treatment of multiple myeloma and autoimmune diseases" Retrieved from the Internet at http://www.diss.tu-berlin.de/diss/servlets/MCRFlleNodeServiet/FUDISS_derivate_000000016111/Dissertation_FO_ohne.pdf, downloaded Jun. 15, 2015).
Genetex 2017 "BCMA antibody [Vicky-1]" downloaded from the World-Wide Web at: genetex.com/BCMA-antibody-Vicky-1-GTX17323.html, downloaded Jul. 24, 2017.
Greenspan et al. 1999 "Defining epitopes: It's not as easy as it seems" *Nature Biotechnology* 17: 936-937.

(Continued)

*Primary Examiner* — Nelson B Moseley, II
(74) *Attorney, Agent, or Firm* — Knobbe, Martens, Olson & Bear, LLP

(57) ABSTRACT

A composition comprising a cell or a population thereof, wherein the cell comprises a polynucleotide encoding an antibody or a fragment thereof that binds CD269 (BCMA), wherein the binding to CD269 (BCMA) disrupts the interaction between CD269 and its native ligands (BAFF and APRIL). Also disclosed is treatment of plasma cell-mediated diseases such as multiple myeloma and autoimmune diseases.

11 Claims, 17 Drawing Sheets

Specification includes a Sequence Listing.

(56) References Cited

OTHER PUBLICATIONS

Khantasup, et al. 2015 "Design and generation of humanized single-chain Fv derived from mouse hybridoma for potential targeting application" *Monoclonal Antibodies in Innumodiagnosis and Immunotherapy* 34: 404-417.
Paul 1993 "Fundamental Immunology: Third Edition" pp. 292-295.
Portolano, et al. 1993 "Lack of promiscuity in autoantigen-specific H and L chain combinations as revealed by human H and L chain 'Roulette'" *The Journal of Immunology* 150(3): 880-887.
R&D Systems 2008 "Monoclonal Anti-human BCMA/TNFRSF17 Antibody" Product Information Sheet (in one page).
R&D Biosystems 2017 "Human BCMA/TNFRSF17 Antibody" downloaded from the World-Wide Web at: rndsystems.com/products/human-bcma-tnfrsf17-antibody-335004_mab193, downloaded Jul. 24, 2017.
Rudikoff et al. 1982 "Single amino acid substitution altering antigen-binding specificity" *Proc. Natl. Acad. Sci.* 79: 1979-1983.
Ryan, M.C. et al. 2007 "Antibody targeting of B-cell maturation antigen on malignant plasma cells" *Molecular Cancer Therapeutics* 6(11): 3009-3018.
Tzartos 1996 "Epitope mapping by antibody competition" *Methods in Molecular Biology* 66: 55-66.
White, et al. 2001 "Antibody-targeted immunotherapy for treatment of malignancy" *Annu. Rev. Med.* 52: 125-145.

A

B d-1

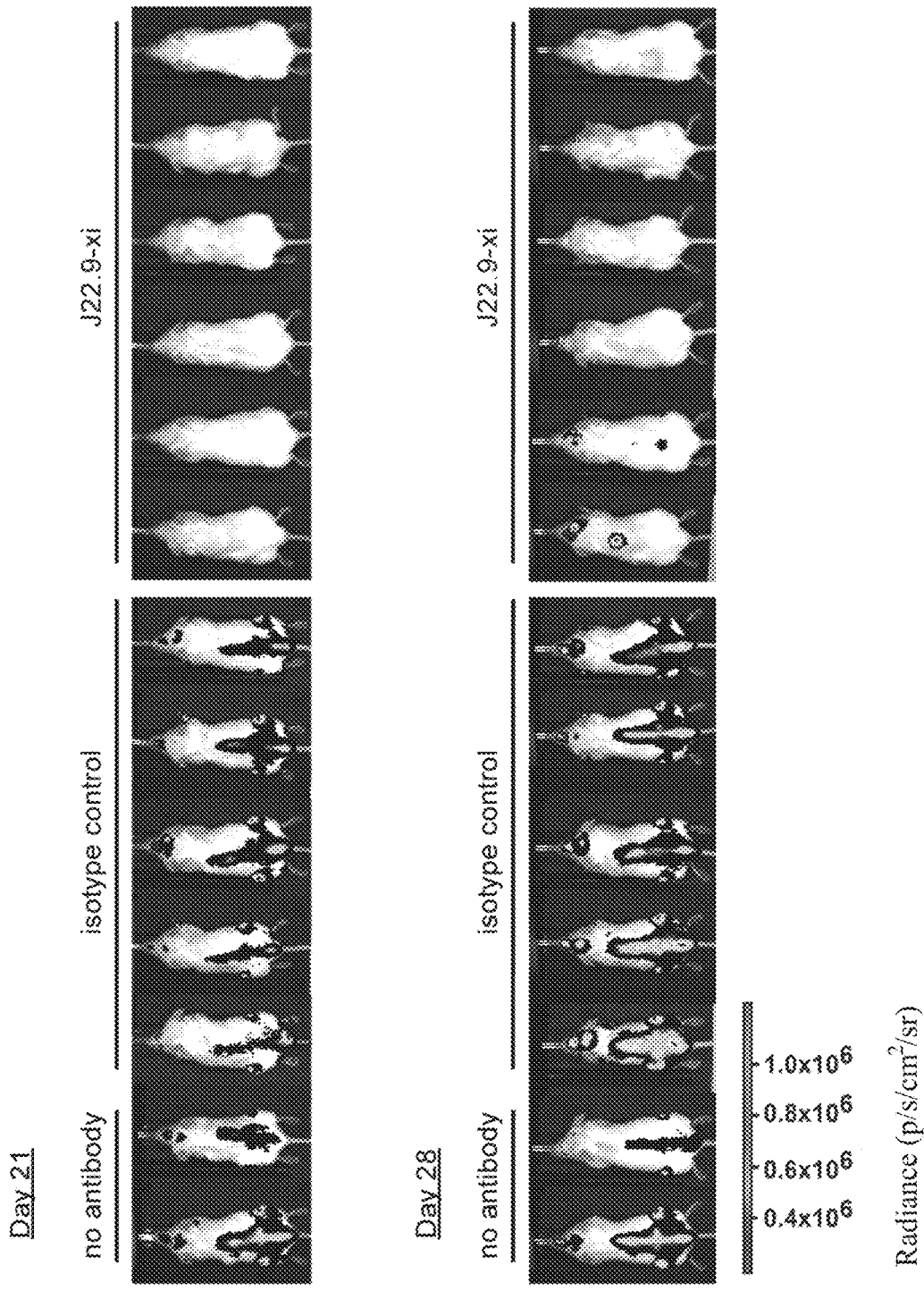

e f g

Experimental time line d

Experimental time line

Fig. 8

**Heavy chain of J22.9 (X24.1pg.45, DSP2.2, JH4 / IGHV4-1*01, IGHD2-4*01, IGHJ4*01)**

DNA sequence (SEQ ID No. 9):

CAGGTGCAGCTGCAGCAGTCTGGAGGTGGCCTGGTGCAGCCTGGAGGATCCCTGAAACTCTCCTGTGCAGCCT
CAGGAATCGATTTTAGTAGATACTGGATGAGTTGGGTTCGGCGGGCTCCAGGGAAAGGACTAGAATGGATTGG
AGAAATTAATCCAGATAGCAGTACAATAAACTATGCACCATCTCTAAAGGATAAATTCATCATCTCCAGAGAC
AACGCCAAAAATACGTTGTACCTGCAAATGAGCAAAGTGAGATCTGAGGACACAGCCCTTTATTACTGTGCAA
GTCTCTACTATGATTACGGGGATGCTATGGACTACTGGGGTCAAGGAACCTCAGTCACCGTCTCCTCA

Protein sequence (single-letter-code, SEQ ID No. 7):

QVQLQ QSGGG LVQPG GSLKL SCAAS GIDFS RY<u>W</u>M<u>S</u> WVRRA PGKGL EWIG<u>E</u> INPDS STINY APSLK DKFII SRDNA KNTLY LQMSK VRSED TALYY CAS<u>LY Y</u>DYGD AMDYW GQGTS VTVSS

Complementarity determining regions (CDRs) are underlined. Amino acids implicated in direct binding to the target extracellular domain of CD269 are emphasized in enlarged bold type.

Protein sequence (three-letter-code, SEQ ID No. 7):

Gln Val Gln Leu Gln Gln Ser Gly Gly Gly Leu Val Gln Pro Gly Gly Ser Leu
Lys Leu Ser Cys Ala Ala Ser Gly Ile Asp Phe Ser Arg Tyr Trp Met Ser Trp
Val Arg Arg Ala Pro Gly Lys Gly Leu Glu Trp Ile Gly Glu Ile Asn Pro Asp
Ser Ser Thr Ile Asn Tyr Ala Pro Ser Leu Lys Asp Lys Phe Ile Ile Ser Arg
Asp Asn Ala Lys Asn Thr Leu Tyr Leu Gln Met Ser Lys Val Arg Ser Glu Asp
Thr Ala Leu Tyr Tyr Cys Ala Ser Leu Tyr Tyr Asp Tyr Gly Asp Ala Met Asp
Tyr Trp Gly Gln Gly Thr Ser Val Thr Val Ser Ser

Fig. 8 (cont.)

**Light chain of J22.9 (19-15, JK5 / IGKV6-15*01, IGKJ5*01)**

DNA sequence (SEQ ID No. 10):

GACATTGTGATGACTCAGTCTCAAAGATTCATGACCACATCAGTAGGAGACAGGGTCAGCGTCACCTGCAAGG
CCAGTCAGAGTGTGGATAGTAATGTAGCCTGGTATCAACAGAAACCTCGGCAATCTCCTAAAGCACTGATTTT
CTCGGCATCCCTCCGGTTCAGTGGAGTCCCTGCTCGCTTCACAGGCAGTGGATCTGGGACAGATTTCACTCTC
ACCATCAGCAATCTGCAGTCTGAAGACTTGGCAGAGTATTTCTGTCAACAATATAACAACTATCCTCTCACGT
TCGGTGCTGGGACCAAGCTGGAGCTGAAACGT

Protein sequence (single-letter-code, SEQ ID No. 8):

DIVMT QSQRF MTTSV GDRVS VTCKA SQSVD S<sub>N</sub>VA<sub>W</sub> Y<sub>QQKP</sub> RQSPK AL<sub>I</sub>FS <sub>A</sub>SL<sub>R</sub>F SGVPA RFTGS GSGTD FTLTI SNLQS EDLAE YFCQ<sub>Q</sub> Y<sub>NN</sub>Y<sub>P</sub> LTFGA GTKLE LKR Complementarity determining regions (CDRs) are underlined. Amino acids involved in direct binding to the target extracellular domain of CD269 are emphasized in enlarged bold type.

Protein sequence (three-letter-code, SEQ ID No. 8):

Asp Ile Val Met Thr Gln Ser Gln Arg Phe Met Thr Thr Ser Val Gly Asp Arg
Val Ser Val Thr Cys Lys Ala Ser Gln Ser Val Asp Ser Asn Val Ala Trp Tyr
Gln Gln Lys Pro Arg Gln Ser Pro Lys Ala Leu Ile Phe Ser Ala Ser Leu Arg
Phe Ser Gly Val Pro Ala Arg Phe Thr Gly Ser Gly Ser Gly Thr Asp Phe Thr
Leu Thr Ile Ser Asn Leu Gln Ser Glu Asp Leu Ala Glu Tyr Phe Cys Gln Gln
Tyr Asn Asn Tyr Pro Leu Thr Phe Gly Ala Gly Thr Lys Leu Glu Leu Lys Arg

GST-BCMA-His tag (SEQ ID No. 11):

MSPILGYWKIKGLVQPTRLLLEYLEEKYEEHLYERDEGDKWRNKKFELGLEFPNLPYYIDGDVKLTQSMAIIR
YIADKHNMLGGCPKERAEISMLEGAVLDIRYGVSRIAYSKDFETLKVDFLSKLPEMLKMFEDRLCHKTYLNGD
HVTHPDFMLYDALDVVLYMDPMCLDAFPKLVCFKKRIEAIPQIDKYLKSSKYIAWPLQGWQATFGGGDHPPKS
DLVPRGSMAGQCSQNEYFDSLLHACIPCQLRCSSNTPPLTCQRYCNASVTNSVKGTNALEHHHHHH

The extracellular domain of BCMA (SEQ ID No. 12);

<u>MAGQCSQNEYFDSLLHACIPCQLRCSSNTPPLTCQRYCNASVTNSVKGTNALE</u> is underlined.

Fig. 9

**HC (IGHV3-74*02, IGHD3-16*02, IGHJ4*01)**

```
         1           11          21          31          41
HX:  XVQLX XSGGG LVQPG GSLXL SCAAS GXXFX XYWMS WVRXA PGKGL EWXGE
HM:  QVQLQ QSGGG LVQPG GSLKL SCAAS GIDFS RYWMS WVRRA PGKGL EWIGE
H0:  EVQLV ESGGG LVQPG GSLRL SCAAS GFTFD DYWMS WVRQA PGKGL EWVGE
H1:  EVQLV QSGGG LVQPG GSLRL SCAAS GFTFD DYWMS WVRQA PGKGL EWVGE
H2:  EVQLV ESGGG LVQPG GSLRL SCAAS GFTFS RYWMS WVRQA PGKGL EWVGE
H3:  EVQLV ESGGG LVQPG GSLRL SCAAS GFTFD DYWMS WVRRA PGKGL EWVGE
H4:  EVQLV QSGGG LVQPG GSLRL SCAAS GFTFS RYWMS WVRQA PGKGL EWVGE
H5:  EVQLV QSGGG LVQPG GSLRL SCAAS GFTFD DYWMS WVRRA PGKGL EWVGE
H6:  EVQLV ESGGG LVQPG GSLRL SCAAS GFTFS RYWMS WVRRA PGKGL EWVGE
H7:  EVQLV QSGGG LVQPG GSLRL SCAAS GFTFS RYWMS WVRRA PGKGL EWVGE 51          61          71          81          91
HX:  INPDS STINY APSLK XXFXI SRDNA KNTLY LQMXX XRXED TAXYY CASLY
HM:  INPDS STINY APSLK DKFII SRDNA KNTLY LQMSK VRSED TALYY CASLY
H0:  INPDS STINY APSLK GRFTI SRDNA KNTLY LQMNS LRAED TAVYY CASLY
H1:  INPDS STINY APSLK GRFTI SRDNA KNTLY LQMNS LRAED TAVYY CASLY
H2:  INPDS STINY APSLK GRFTI SRDNA KNTLY LQMNS LRAED TAVYY CASLY
H3:  INPDS STINY APSLK GRFTI SRDNA KNTLY LQMNS LRAED TAVYY CASLY
H4:  INPDS STINY APSLK GRFTI SRDNA KNTLY LQMNS LRAED TAVYY CASLY
H5:  INPDS STINY APSLK GRFTI SRDNA KNTLY LQMNS LRAED TAVYY CASLY
H6:  INPDS STINY APSLK GRFTI SRDNA KNTLY LQMNS LRAED TAVYY CASLY
H7:  INPDS STINY APSLK GRFTI SRDNA KNTLY LQMNS LRAED TAVYY CASLY 101         111
HX:  YDYGD AMDYW GQGTX VTVSS
HM:  YDYGD AMDYW GQGTS VTVSS
H0:  YDYGD AMDYW GQGTL VTVSS
H1:  YDYGD AMDYW GQGTL VTVSS
H2:  YDYGD AMDYW GQGTL VTVSS
H3:  YDYGD AMDYW GQGTL VTVSS
H4:  YDYGD AMDYW GQGTL VTVSS
H5:  YDYGD AMDYW GQGTL VTVSS
H6:  YDYGD AMDYW GQGTL VTVSS
H7:  YDYGD AMDYW GQGTL VTVSS
```

Black: Amino acids changed for human sequence.
Underlined: CDR regions
X: Variable amino acid according to either mouse or humanised sequences

Fig. 9 (cont.)

LC (IGKV1-16*01, IGKJ2*04)

```
            1           11          21          31          41
 LX: DIVMT QSXXX XXXSV GDXVX XTCKA SQSVD SNVAW YQQKP XQXPK XLIXS
 LM: DIVMT QSQRF MTTSV GDRVS VTCKA SQSVD SNVAW YQQKP RQSPK ALIFS
 L0: DIVMT QSPAT LSVSV GDEVT LTCKA SQSVD SNVAW YQQKP GQAPK LLIYS
 L1: DIVMT QSPAT LSVSV GDEVT LTCKA SQSVD SNVAW YQQKP GQSPK LLIYS
 L2: DIVMT QSPAT LSVSV GDEVT LTCKA SQSVD SNVAW YQQKP GQAPK ALIYS
 L3: DIVMT QSPAT LSVSV GDEVT LTCKA SQSVD SNVAW YQQKP GQAPK LLIYS
 L4: DIVMT QSPAT LSVSV GDEVT LTCKA SQSVD SNVAW YQQKP GQAPK LLIYS
 L5: DIVMT QSPAT LSVSV GDEVT LTCKA SQSVD SNVAW YQQKP GQSPK ALIYS
 L6: DIVMT QSPAT LSVSV GDEVT LTCKA SQSVD SNVAW YQQKP GQSPK LLIYS
 L7: DIVMT QSPAT LSVSV GDEVT LTCKA SQSVD SNVAW YQQKP GQSPK LLIYS
 L8: DIVMT QSPAT LSVSV GDEVT LTCKA SQSVD SNVAW YQQKP GQAPK ALIYS
 L9: DIVMT QSPAT LSVSV GDEVT LTCKA SQSVD SNVAW YQQKP GQAPK ALIYS
L10: DIVMT QSPAT LSVSV GDEVT LTCKA SQSVD SNVAW YQQKP GQAPK LLIYS
L11: DIVMT QSPAT LSVSV GDEVT LTCKA SQSVD SNVAW YQQKP GQSPK ALIYS
L12: DIVMT QSPAT LSVSV GDEVT LTCKA SQSVD SNVAW YQQKP GQSPK ALIYS
L13: DIVMT QSPAT LSVSV GDEVT LTCKA SQSVD SNVAW YQQKP GQSPK LLIYS
L14: DIVMT QSPAT LSVSV GDEVT LTCKA SQSVD SNVAW YQQKP GQAPK ALIYS
L15: DIVMT QSPAT LSVSV GDEVT LTCKA SQSVD SNVAW YQQKP GQSPK ALIYS
L16: DIVMT QSPAT LSVSV GDEVT LTCKA SQSVD SNVAW YQQKP GQAPK LLIFS
L17: DIVMT QSPAT LSVSV GDEVT LTCKA SQSVD SNVAW YQQKP GQSPK LLIFS
L18: DIVMT QSPAT LSVSV GDEVT LTCKA SQSVD SNVAW YQQKP GQSPK ALIFS
L19: DIVMT QSPAT LSVSV GDEVT LTCKA SQSVD SNVAW YQQKP GQSPK ALIFS
L20: DIVMT QSPAT LSVSV GDEVT LTCKA SQSVD SNVAW YQQKP GQSPK ALIFS
L21: DIVMT QSPAT LSVSV GDEVT LTCKA SQSVD SNVAW YQQKP GQSPK ALIFS
L22: DIVMT QSPAT LSVSV GDEVT LTCKA SQSVD SNVAW YQQKP GQSPK LLIFS
L23: DIVMT QSPAT LSVSV GDEVT LTCKA SQSVD SNVAW YQQKP GQSPK LLIFS
L24: DIVMT QSPAT LSVSV GDEVT LTCKA SQSVD SNVAW YQQKP GQAPK ALIFS
L25: DIVMT QSPAT LSVSV GDEVT LTCKA SQSVD SNVAW YQQKP GQAPK ALIFS
L26: DIVMT QSPAT LSVSV GDEVT LTCKA SQSVD SNVAW YQQKP GQAPK LLIFS
L27: DIVMT QSPAT LSVSV GDEVT LTCKA SQSVD SNVAW YQQKP GQSPK ALIFS
L28: DIVMT QSPAT LSVSV GDEVT LTCKA SQSVD SNVAW YQQKP GQSPK ALIFS
L29: DIVMT QSPAT LSVSV GDEVT LTCKA SQSVD SNVAW YQQKP GQSPK LLIFS
L30: DIVMT QSPAT LSVSV GDEVT LTCKA SQSVD SNVAW YQQKP GQAPK ALIFS
```

Black: Amino acids changed for human sequence.
Underlined: CDR regions
X: Variable amino acid according to either mouse or humanised sequences

Fig. 9 (cont.)

```
         51    61    71    71    81    91
LX:  XXLRF SGVPA RFXGS GSGTD FTLTI SXLQS EDXAX YXCQQ YNNYP
LM:  ASLRF SGVPA RFTGS GSGTD FTLTI SNLQS EDLAE YFCQQ YNNYP
L0:  DDLRF SGVPA RFSGS GSGTD FTLTI SSLQS EDFAV YYCQQ YNNYP
L1:  DDLRF SGVPA RFSGS GSGTD FTLTI SSLQS EDFAV YYCQQ YNNYP
L2:  DDLRF SGVPA RFSGS GSGTD FTLTI SSLQS EDFAV YYCQQ YNNYP
L3:  ASLRF SGVPA RFSGS GSGTD FTLTI SSLQS EDFAV YYCQQ YNNYP
L4:  DDLRF SGVPA RFSGS GSGTD FTLTI SSLQS EDFAE YYCQQ YNNYP
L5:  DDLRF SGVPA RFSGS GSGTD FTLTI SSLQS EDFAV YYCQQ YNNYP
L6:  ASLRF SGVPA RFSGS GSGTD FTLTI SSLQS EDFAV YYCQQ YNNYP
L7:  DDLRF SGVPA RFSGS GSGTD FTLTI SSLQS EDFAE YYCQQ YNNYP
L8:  ASLRF SGVPA RFSGS GSGTD FTLTI SSLQS EDFAV YYCQQ YNNYP
L9:  DDLRF SGVPA RFSGS GSGTD FTLTI SSLQS EDFAE YYCQQ YNNYP
L10: ASLRF SGVPA RFSGS GSGTD FTLTI SSLQS EDFAE YYCQQ YNNYP
L11: ASLRF SGVPA RFSGS GSGTD FTLTI SSLQS EDFAV YYCQQ YNNYP
L12: DDLRF SGVPA RFSGS GSGTD FTLTI SSLQS EDFAE YYCQQ YNNYP
L13: ASLRF SGVPA RFSGS GSGTD FTLTI SSLQS EDFAE YYCQQ YNNYP
L14: ASLRF SGVPA RFSGS GSGTD FTLTI SSLQS EDFAE YYCQQ YNNYP
L15: ASLRF SGVPA RFSGS GSGTD FTLTI SSLQS EDFAE YYCQQ YNNYP
L16: DDLRF SGVPA RFSGS GSGTD FTLTI SSLQS EDFAV YYCQQ YNNYP
L17: DDLRF SGVPA RFSGS GSGTD FTLTI SSLQS EDFAV YYCQQ YNNYP
L18: DDLRF SGVPA RFSGS GSGTD FTLTI SSLQS EDFAV YYCQQ YNNYP
L19: ASLRF SGVPA RFSGS GSGTD FTLTI SSLQS EDFAV YYCQQ YNNYP
L20: ASLRF SGVPA RFSGS GSGTD FTLTI SSLQS EDFAE YYCQQ YNNYP
L21: DDLRF SGVPA RFSGS GSGTD FTLTI SSLQS EDFAV YYCQQ YNNYP
L21: ASLRF SGVPA RFSGS GSGTD FTLTI SSLQS EDFAV YYCQQ YNNYP
L23: DDLRF SGVPA RFSGS GSGTD FTLTI SSLQS EDFAE YYCQQ YNNYP
L24: ASLRF SGVPA RFSGS GSGTD FTLTI SSLQS EDFAV YYCQQ YNNYP
L25: DDLRF SGVPA RFSGS GSGTD FTLTI SSLQS EDFAE YYCQQ YNNYP
L26: ASLRF SGVPA RFSGS GSGTD FTLTI SSLQS EDFAE YYCQQ YNNYP
L27: ASLRF SGVPA RFSGS GSGTD FTLTI SSLQS EDFAV YYCQQ YNNYP
L28: DDLRF SGVPA RFSGS GSGTD FTLTI SSLQS EDFAE YYCQQ YNNYP
L29: ASLRF SGVPA RFSGS GSGTD FTLTI SSLQS EDFAE YYCQQ YNNYP
L30: ASLRF SGVPA RFSGS GSGTD FTLTI SSLQS EDFAE YYCQQ YNNYP
```

Black: Amino acids changed for human sequence.
Underlined: CDR regions
X: Variable amino acid according to either mouse or humanised sequences

Fig. 9 (cont.)

```
             101
 LX: LTFGA GTKLE LKR
 LM: LTFGA GTKLE LKR
 L0: LTFGA GTKLE LKR
 L1: LTFGA GTKLE LKR
 L2: LTFGA GTKLE LKR
 L3: LTFGA GTKLE LKR
 L4: LTFGA GTKLE LKR
 L5: LTFGA GTKLE LKR
 L6: LTFGA GTKLE LKR
 L7: LTFGA GTKLE LKR
 L8: LTFGA GTKLE LKR
 L9: LTFGA GTKLE LKR
L10: LTFGA GTKLE LKR
L11: LTFGA GTKLE LKR
L12: LTFGA GTKLE LKR
L13: LTFGA GTKLE LKR
L14: LTFGA GTKLE LKR
L15: LTFGA GTKLE LKR
L16: LTFGA GTKLE LKR
L17: LTFGA GTKLE LKR
L18: LTFGA GTKLE LKR
L19: LTFGA GTKLE LKR
L20: LTFGA GTKLE LKR
L21: LTFGA GTKLE LKR
L22: LTFGA GTKLE LKR
L23: LTFGA GTKLE LKR
L24: LTFGA GTKLE LKR
L25: LTFGA GTKLE LKR
L26: LTFGA GTKLE LKR
L27: LTFGA GTKLE LKR
L28: LTFGA GTKLE LKR
L29: LTFGA GTKLE LKR
```

Black: Amino acids changed for human sequence.
Underlined: CDR regions
X: Variable amino acid according to either mouse or humanised sequences

SEQUENCE LISTING

```
<160> NUMBER OF SEQ ID NOS: 113

<210> SEQ ID NO 1
<211> LENGTH: 5
<212> TYPE: PRT
<213> ORGANISM: Artificial
<220> FEATURE:
<223> OTHER INFORMATION: CDR

<400> SEQUENCE: 1

Arg Tyr Trp Met Ser
1               5

<210> SEQ ID NO 2
<211> LENGTH: 17
<212> TYPE: PRT
<213> ORGANISM: Artificial
<220> FEATURE:
<223> OTHER INFORMATION: CDR
```

-continued

<400> SEQUENCE: 2

Glu Ile Asn Pro Asp Ser Ser Thr Ile Asn Tyr Ala Pro Ser Leu Lys
1               5                   10                  15

Asp

<210> SEQ ID NO 3
<211> LENGTH: 13
<212> TYPE: PRT
<213> ORGANISM: Artificial
<220> FEATURE:
<223> OTHER INFORMATION: CDR

<400> SEQUENCE: 3

Ser Leu Tyr Tyr Asp Tyr Gly Asp Ala Met Asp Tyr Trp
1               5                   10

<210> SEQ ID NO 4
<211> LENGTH: 11
<212> TYPE: PRT
<213> ORGANISM: Artificial
<220> FEATURE:
<223> OTHER INFORMATION: CDR

<400> SEQUENCE: 4

Lys Ala Ser Gln Ser Val Asp Ser Asn Val Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDR

<400> SEQUENCE: 5

Ser Ala Ser Leu Arg Phe Ser
1               5

<210> SEQ ID NO 6
<211> LENGTH: 11
<212> TYPE: PRT
<213> ORGANISM: Artificial
<220> FEATURE:
<223> OTHER INFORMATION: CDR

<400> SEQUENCE: 6

Gln Gln Tyr Asn Asn Tyr Pro Leu Thr Phe Gly
1               5                   10

<210> SEQ ID NO 7
<211> LENGTH: 120
<212> TYPE: PRT
<213> ORGANISM: Artificial
<220> FEATURE:
<223> OTHER INFORMATION: VH

<400> SEQUENCE: 7

Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
                20                  25                  30

Trp Met Ser Trp Val Arg Arg Ala Pro Gly Lys Gly Leu Glu Trp Ile
            35                  40                  45

Gly Glu Ile Asn Pro Asp Ser Ser Thr Ile Asn Tyr Ala Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Ser Leu Tyr Tyr Asp Tyr Gly Asp Ala Met Asp Tyr Trp Gly Gln
            100                 105                 110

Gly Thr Ser Val Thr Val Ser Ser
        115                 120

<210> SEQ ID NO 8
<211> LENGTH: 108
<212> TYPE: PRT
<213> ORGANISM: Artificial
<220> FEATURE:
<223> OTHER INFORMATION: VL

<400> SEQUENCE: 8

Asp Ile Val Met Thr Gln Ser Gln Arg Phe Met Thr Thr Ser Val Gly
1               5                   10                  15

Asp Arg Val Ser Val Thr Cys Lys Ala Ser Gln Ser Val Asp Ser Asn
            20                  25                  30

Val Ala Trp Tyr Gln Gln Lys Pro Arg Gln Ser Pro Lys Ala Leu Ile
        35                  40                  45

Phe Ser Ala Ser Leu Arg Phe Ser Gly Val Pro Ala Arg Phe Thr Gly
    50                  55                  60

Ser Gly Ser Gly Thr Asp Phe Thr Leu Thr Ile Ser Asn Leu Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 9
<211> LENGTH: 360
<212> TYPE: DNA
<213> ORGANISM: Artificial
<220> FEATURE:
<223> OTHER INFORMATION: VH

<400> SEQUENCE: 9
caggtgcagc tgcagcagtc tggaggtggc ctggtgcagc ctggaggatc cctgaaactc        60
tcctgtgcag cctcaggaat cgattttagt agatactgga tgagttgggt tcggcgggct       120
ccagggaaag gactagaatg gattggagaa attaatccag atagcagtac aataaactat       180
gcaccatctc taaggataa attcatcatc tccagagaca cgccaaaaa tacgttgtac         240 ctgcaaatga gcaaagtgag atctgaggac acagcccttt attactgtgc aagtctctac       300
tatgattacg gggatgctat ggactactgg ggtcaaggaa cctcagtcac cgtctcctca       360

<210> SEQ ID NO 10
<211> LENGTH: 324
<212> TYPE: DNA
<213> ORGANISM: Artificial
<220> FEATURE:
<223> OTHER INFORMATION: VL

<400> SEQUENCE: 10
gacattgtga tgactcagtc tcaaagattc atgaccacat cagtaggaga cagggtcagc        60

```
gtcacctgca aggccagtca gagtgtggat agtaatgtag cctggtatca acagaaacct    120
cggcaatctc ctaaagcact gattttctcg catccctcc ggttcagtgg agtccctgct    180
cgcttcacag gcagtggatc tgggacagat ttcactctca ccatcagcaa tctgcagtct    240
gaagacttgg cagagtattt ctgtcaacaa tataacaact atcctctcac gttcggtgct    300
gggaccaagc tggagctgaa acgt                                          324
```

<210> SEQ ID NO 11
<211> LENGTH: 285
<212> TYPE: PRT
<213> ORGANISM: Artificial
<220> FEATURE:
<223> OTHER INFORMATION: BCMA

<400> SEQUENCE: 11

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Val Pro Arg
    210                 215                 220

Gly Ser Met Ala Gly Gln Cys Ser Gln Asn Glu Tyr Phe Asp Ser Leu
225                 230                 235                 240

Leu His Ala Cys Ile Pro Cys Gln Leu Arg Cys Ser Ser Asn Thr Pro
                245                 250                 255

Pro Leu Thr Cys Gln Arg Tyr Cys Asn Ala Ser Val Thr Asn Ser Val
            260                 265                 270

Lys Gly Thr Asn Ala Leu Glu His His His His His
        275                 280                 285
```

<210> SEQ ID NO 12
<211> LENGTH: 53
<212> TYPE: PRT

<213> ORGANISM: Homo sapiens

<400> SEQUENCE: 12

Met Ala Gly Gln Cys Ser Gln Asn Glu Tyr Phe Asp Ser Leu Leu His
1               5                   10                  15

Ala Cys Ile Pro Cys Gln Leu Arg Cys Ser Ser Asn Thr Pro Pro Leu
            20                  25                  30

Thr Cys Gln Arg Tyr Cys Asn Ala Ser Val Thr Asn Ser Val Lys Gly
        35                  40                  45

Thr Asn Ala Leu Glu
    50

<210> SEQ ID NO 13
<211> LENGTH: 56
<212> TYPE: PRT
<213> ORGANISM: Homo sapiens

<400> SEQUENCE: 13

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Leu Glu
    50                  55

<210> SEQ ID NO 14
<211> LENGTH: 20
<212> TYPE: PRT
<213> ORGANISM: Homo sapiens

<400> SEQUENCE: 14

Tyr Phe Asp Ser Leu Leu His Ala Cys Ile Pro Cys Gln Leu Arg Cys
1               5                   10                  15

Ser Ser Asn Thr
            20

<210> SEQ ID NO 15
<211> LENGTH: 5
<212> TYPE: PRT
<213> ORGANISM: Artificial
<220> FEATURE:
<223> OTHER INFORMATION: Antibody sequence

<400> SEQUENCE: 15

Asp Tyr Trp Met Ser
1               5

<210> SEQ ID NO 16
<211> LENGTH: 17
<212> TYPE: PRT
<213> ORGANISM: Artificial
<220> FEATURE:
<223> OTHER INFORMATION: Antibody sequence

<400> SEQUENCE: 16

Glu Ile Asn Pro Asp Ser Ser Thr Ile Asn Tyr Ala Pro Ser Leu Lys
1               5                   10                  15

Gly

-continued

```
<210> SEQ ID NO 17
<211> LENGTH: 7
<212> TYPE: PRT
<213> ORGANISM: Artificial
<220> FEATURE:
<223> OTHER INFORMATION: Antibody sequence

<400> SEQUENCE: 17

Ser Asp Asp Leu Arg Phe Ser
1               5

<210> SEQ ID NO 18
<211> LENGTH: 120
<212> TYPE: PRT
<213> ORGANISM: Artificial
<220> FEATURE:
<223> OTHER INFORMATION: Antibody sequence

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Trp Met Ser Trp Val Arg Gln Ala Pro Gly Lys Gly Leu Glu Trp Val
            35                  40                  45

Gly Glu Ile Asn Pro Asp Ser Ser Thr Ile Asn Tyr Ala Pro Ser Leu
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
                100                 105                 110

Gly Thr Leu Val Thr Val Ser Ser
            115                 120

<210> SEQ ID NO 19
<211> LENGTH: 120
<212> TYPE: PRT
<213> ORGANISM: Artificial
<220> FEATURE:
<223> OTHER INFORMATION: Antibody sequence

<400> SEQUENCE: 19

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
                20                  25                  30

Trp Met Ser Trp Val Arg Gln Ala Pro Gly Lys Gly Leu Glu Trp Val
            35                  40                  45

Gly Glu Ile Asn Pro Asp Ser Ser Thr Ile Asn Tyr Ala Pro Ser Leu
        50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
                100                 105                 110

Gly Thr Leu Val Thr Val Ser Ser
            115                 120
```

```
<210> SEQ ID NO 20
<211> LENGTH: 120
<212> TYPE: PRT
<213> ORGANISM: Artificial
<220> FEATURE:
<223> OTHER INFORMATION: Antibody sequence

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 21
<211> LENGTH: 120
<212> TYPE: PRT
<213> ORGANISM: Artificial
<220> FEATURE:
<223> OTHER INFORMATION: Antibody sequence

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: Artificial
<220> FEATURE:
<223> OTHER INFORMATION: Antibody sequence

<400> SEQUENCE: 22
```

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Gln Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
            115                 120

<210> SEQ ID NO 23
<211> LENGTH: 120
<212> TYPE: PRT
<213> ORGANISM: Artificial
<220> FEATURE:
<223> OTHER INFORMATION: Antibody sequence

<400> SEQUENCE: 23

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
            115                 120

<210> SEQ ID NO 24
<211> LENGTH: 120
<212> TYPE: PRT
<213> ORGANISM: Artificial
<220> FEATURE:
<223> OTHER INFORMATION: Antibody sequence

<400> SEQUENCE: 24

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
            115                 120

<210> SEQ ID NO 25
<211> LENGTH: 120
<212> TYPE: PRT
<213> ORGANISM: Artificial
<220> FEATURE:
<223> OTHER INFORMATION: Antibody sequence

<400> SEQUENCE: 25

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
            115                 120

<210> SEQ ID NO 26
<211> LENGTH: 108
<212> TYPE: PRT
<213> ORGANISM: Artificial
<220> FEATURE:
<223> OTHER INFORMATION: Antibody sequence

<400> SEQUENCE: 26

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 27
<211> LENGTH: 108
<212> TYPE: PRT
<213> ORGANISM: Artificial
<220> FEATURE:
<223> OTHER INFORMATION: Antibody sequence

<400> SEQUENCE: 27

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 28
<211> LENGTH: 108
<212> TYPE: PRT
<213> ORGANISM: Artificial
<220> FEATURE:
<223> OTHER INFORMATION: Antibody sequence

<400> SEQUENCE: 28

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 29
<211> LENGTH: 108
<212> TYPE: PRT
<213> ORGANISM: Artificial
<220> FEATURE:
<223> OTHER INFORMATION: Antibody sequence

<400> SEQUENCE: 29

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

```
Tyr Ser Ala Ser Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105
```

<210> SEQ ID NO 30
<211> LENGTH: 108
<212> TYPE: PRT
<213> ORGANISM: Artificial
<220> FEATURE:
<223> OTHER INFORMATION: Antibody sequence

<400> SEQUENCE: 30

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Asp Asp Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105
```

<210> SEQ ID NO 31
<211> LENGTH: 108
<212> TYPE: PRT
<213> ORGANISM: Artificial
<220> FEATURE:
<223> OTHER INFORMATION: Antibody sequence

<400> SEQUENCE: 31

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Asp Asp Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105
```

<210> SEQ ID NO 32
<211> LENGTH: 108
<212> TYPE: PRT

<213> ORGANISM: Artificial
<220> FEATURE:
<223> OTHER INFORMATION: Antibody sequence

<400> SEQUENCE: 32

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 33
<211> LENGTH: 108
<212> TYPE: PRT
<213> ORGANISM: Artificial
<220> FEATURE:
<223> OTHER INFORMATION: Antibody sequence

<400> SEQUENCE: 33

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 34
<211> LENGTH: 108
<212> TYPE: PRT
<213> ORGANISM: Artificial
<220> FEATURE:
<223> OTHER INFORMATION: Antibody sequence

<400> SEQUENCE: 34

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Ala Ser Leu Arg Phe Ser Gly Val Pro Ala Arg Phe Ser Gly
    50                  55                  60

-continued

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 35
<211> LENGTH: 108
<212> TYPE: PRT
<213> ORGANISM: Artificial
<220> FEATURE:
<223> OTHER INFORMATION: Antibody sequence

<400> SEQUENCE: 35

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 36
<211> LENGTH: 108
<212> TYPE: PRT
<213> ORGANISM: Artificial
<220> FEATURE:
<223> OTHER INFORMATION: Antibody sequence

<400> SEQUENCE: 36

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 37
<211> LENGTH: 108
<212> TYPE: PRT
<213> ORGANISM: Artificial
<220> FEATURE:
<223> OTHER INFORMATION: Antibody sequence

<400> SEQUENCE: 37

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 38
<211> LENGTH: 108
<212> TYPE: PRT
<213> ORGANISM: Artificial
<220> FEATURE:
<223> OTHER INFORMATION: Antibody sequence

<400> SEQUENCE: 38

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 39
<211> LENGTH: 108
<212> TYPE: PRT
<213> ORGANISM: Artificial
<220> FEATURE:
<223> OTHER INFORMATION: Antibody sequence

<400> SEQUENCE: 39

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

```
Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 40
<211> LENGTH: 108
<212> TYPE: PRT
<213> ORGANISM: Artificial
<220> FEATURE:
<223> OTHER INFORMATION: Antibody sequence

<400> SEQUENCE: 40

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 41
<211> LENGTH: 108
<212> TYPE: PRT
<213> ORGANISM: Artificial
<220> FEATURE:
<223> OTHER INFORMATION: Antibody sequence

<400> SEQUENCE: 41

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 42
<211> LENGTH: 108
<212> TYPE: PRT
<213> ORGANISM: Artificial
<220> FEATURE:
<223> OTHER INFORMATION: Antibody sequence

<400> SEQUENCE: 42
```

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
                100                 105

<210> SEQ ID NO 43
<211> LENGTH: 108
<212> TYPE: PRT
<213> ORGANISM: Artificial
<220> FEATURE:
<223> OTHER INFORMATION: Antibody sequence

<400> SEQUENCE: 43

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
                100                 105

<210> SEQ ID NO 44
<211> LENGTH: 108
<212> TYPE: PRT
<213> ORGANISM: Artificial
<220> FEATURE:
<223> OTHER INFORMATION: Antibody sequence

<400> SEQUENCE: 44

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

```
Thr Phe Gly Ala Gly Thr Lys Leu Glu Leu Lys Arg
            100                 105

<210> SEQ ID NO 45
<211> LENGTH: 108
<212> TYPE: PRT
<213> ORGANISM: Artificial
<220> FEATURE:
<223> OTHER INFORMATION: Antibody sequence

<400> SEQUENCE: 45

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Ala Ser Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 46
<211> LENGTH: 108
<212> TYPE: PRT
<213> ORGANISM: Artificial
<220> FEATURE:
<223> OTHER INFORMATION: Antibody sequence

<400> SEQUENCE: 46

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Ala Ser Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 47
<211> LENGTH: 108
<212> TYPE: PRT
<213> ORGANISM: Artificial
<220> FEATURE:
<223> OTHER INFORMATION: Antibody sequence

<400> SEQUENCE: 47

Asp Ile Val Met Thr Gln Ser Pro Ala Thr Leu Ser Val Ser Val Gly
1               5                   10                  15
```

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 48
<211> LENGTH: 108
<212> TYPE: PRT
<213> ORGANISM: Artificial
<220> FEATURE:
<223> OTHER INFORMATION: Antibody sequence

<400> SEQUENCE: 48

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 49
<211> LENGTH: 108
<212> TYPE: PRT
<213> ORGANISM: Artificial
<220> FEATURE:
<223> OTHER INFORMATION: Antibody sequence

<400> SEQUENCE: 49

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

```
<210> SEQ ID NO 50
<211> LENGTH: 108
<212> TYPE: PRT
<213> ORGANISM: Artificial
<220> FEATURE:
<223> OTHER INFORMATION: Antibody sequence

<400> SEQUENCE: 50

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 51
<211> LENGTH: 108
<212> TYPE: PRT
<213> ORGANISM: Artificial
<220> FEATURE:
<223> OTHER INFORMATION: Antibody sequence

<400> SEQUENCE: 51

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 52
<211> LENGTH: 108
<212> TYPE: PRT
<213> ORGANISM: Artificial
<220> FEATURE:
<223> OTHER INFORMATION: Antibody sequence

<400> SEQUENCE: 52

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30
```

Val Ala Trp Tyr Gln Gln Lys Pro Gly Gln Ala Pro Lys Leu Leu Ile
         35                  40                  45

Phe Ser Ala Ser Leu Arg Phe Ser Gly Val Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Glu Tyr Tyr Cys Gln Gln Tyr Asn Asn Tyr Pro Leu
                 85                  90                  95

Thr Phe Gly Ala Gly Thr Lys Leu Glu Leu Lys Arg
                100                 105

<210> SEQ ID NO 53
<211> LENGTH: 108
<212> TYPE: PRT
<213> ORGANISM: Artificial
<220> FEATURE:
<223> OTHER INFORMATION: Antibody sequence

<400> SEQUENCE: 53

Asp Ile Val Met Thr Gln Ser Pro Ala Thr Leu Ser Val Ser Val Gly
 1               5                  10                  15

Asp Glu Val Thr Leu Thr Cys Lys Ala Ser Gln Ser Val Asp Ser Asn
                 20                  25                  30

Val Ala Trp Tyr Gln Gln Lys Pro Gly Gln Ser Pro Lys Ala Leu Ile
         35                  40                  45

Phe Ser Ala Ser Leu Arg Phe Ser Gly Val Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                 85                  90                  95

Thr Phe Gly Ala Gly Thr Lys Leu Glu Leu Lys Arg
                100                 105

<210> SEQ ID NO 54
<211> LENGTH: 108
<212> TYPE: PRT
<213> ORGANISM: Artificial
<220> FEATURE:
<223> OTHER INFORMATION: Antibody sequence

<400> SEQUENCE: 54

Asp Ile Val Met Thr Gln Ser Pro Ala Thr Leu Ser Val Ser Val Gly
 1               5                  10                  15

Asp Glu Val Thr Leu Thr Cys Lys Ala Ser Gln Ser Val Asp Ser Asn
                 20                  25                  30

Val Ala Trp Tyr Gln Gln Lys Pro Gly Gln Ser Pro Lys Ala Leu Ile
         35                  40                  45

Phe Ser Asp Asp Leu Arg Phe Ser Gly Val Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Glu Tyr Tyr Cys Gln Gln Tyr Asn Asn Tyr Pro Leu
                 85                  90                  95

Thr Phe Gly Ala Gly Thr Lys Leu Glu Leu Lys Arg
                100                 105

<210> SEQ ID NO 55

```
<211> LENGTH: 108
<212> TYPE: PRT
<213> ORGANISM: Artificial
<220> FEATURE:
<223> OTHER INFORMATION: Antibody sequence

<400> SEQUENCE: 55

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 56
<211> LENGTH: 108
<212> TYPE: PRT
<213> ORGANISM: Artificial
<220> FEATURE:
<223> OTHER INFORMATION: Antibody sequence

<400> SEQUENCE: 56

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 57
<211> LENGTH: 5
<212> TYPE: PRT
<213> ORGANISM: Artificial
<220> FEATURE:
<223> OTHER INFORMATION: Antibody sequence
<220> FEATURE:
<221> NAME/KEY: misc_feature
<222> LOCATION: (1)..(1)
<223> OTHER INFORMATION: Xaa can be any naturally occurring amino acid

<400> SEQUENCE: 57

Xaa Tyr Trp Met Ser
1               5

<210> SEQ ID NO 58
```

```
<211> LENGTH: 17
<212> TYPE: PRT
<213> ORGANISM: Artificial
<220> FEATURE:
<223> OTHER INFORMATION: Antibody sequence
<220> FEATURE:
<221> NAME/KEY: misc_feature
<222> LOCATION: (17)..(17)
<223> OTHER INFORMATION: Xaa can be any naturally occurring amino acid

<400> SEQUENCE: 58

Glu Ile Asn Pro Asp Ser Ser Thr Ile Asn Tyr Ala Pro Ser Leu Lys
1               5                   10                  15

Xaa

<210> SEQ ID NO 59
<211> LENGTH: 7
<212> TYPE: PRT
<213> ORGANISM: Artificial
<220> FEATURE:
<223> OTHER INFORMATION: Antibody sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 59

Ser Xaa Xaa Leu Arg Phe Ser
1               5

<210> SEQ ID NO 60
<211> LENGTH: 120
<212> TYPE: PRT
<213> ORGANISM: Artificial
<220> FEATURE:
<223> OTHER INFORMATION: Antibody sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: misc_feature
<222> LOCATION: (27)..(28)
<223> OTHER INFORMATION: Xaa can be any naturally occurring amino acid
<220> FEATURE:
<221> NAME/KEY: misc_feature
<222> LOCATION: (30)..(31)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (48)..(48)
<223> OTHER INFORMATION: Xaa can be any naturally occurring amino acid
<220> FEATURE:
<221> NAME/KEY: misc_feature
<222> LOCATION: (66)..(67)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
```

```
<222> LOCATION: (84)..(86)
<223> OTHER INFORMATION: Xaa can be any naturally occurring amino acid
<220> FEATURE:
<221> NAME/KEY: misc_feature
<222> LOCATION: (88)..(88)
<223> OTHER INFORMATION: Xaa can be any naturally occurring amino acid
<220> FEATURE:
<221> NAME/KEY: misc_feature
<222> LOCATION: (93)..(93)
<223> OTHER INFORMATION: Xaa can be any naturally occurring amino acid
<220> FEATURE:
<221> NAME/KEY: misc_feature
<222> LOCATION: (115)..(115)
<223> OTHER INFORMATION: Xaa can be any naturally occurring amino acid

<400> SEQUENCE: 60

Xaa Val Gln Leu Xaa Xaa Ser Gly Gly Gly Leu Val Gln Pro Gly Gly
  1               5                  10                  15

Ser Leu Xaa Leu Ser Cys Ala Ala Ser Gly Xaa Xaa Phe Xaa Xaa Tyr
             20                  25                  30

Trp Met Ser Trp Val Arg Xaa Ala Pro Gly Lys Gly Leu Glu Trp Xaa
         35                  40                  45

Gly Glu Ile Asn Pro Asp Ser Ser Thr Ile Asn Tyr Ala Pro Ser Leu
     50                  55                  60

Lys Xaa Xaa Phe Xaa Ile Ser Arg Asp Asn Ala Lys Asn Thr Leu Tyr
 65                  70                  75                  80

Leu Gln Met Xaa Xaa Xaa Arg Xaa Glu Asp Thr Ala Xaa Tyr Tyr Cys
                 85                  90                  95

Ala Ser Leu Tyr Tyr Asp Tyr Gly Asp Ala Met Asp Tyr Trp Gly Gln
            100                 105                 110

Gly Thr Xaa Val Thr Val Ser Ser
            115                 120

<210> SEQ ID NO 61
<211> LENGTH: 108
<212> TYPE: PRT
<213> ORGANISM: Artificial
<220> FEATURE:
<223> OTHER INFORMATION: Antibody sequence
<220> FEATURE:
<221> NAME/KEY: misc_feature
<222> LOCATION: (8)..(13)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (41)..(41)
<223> OTHER INFORMATION: Xaa can be any naturally occurring amino acid
<220> FEATURE:
<221> NAME/KEY: misc_feature
<222> LOCATION: (43)..(43)
<223> OTHER INFORMATION: Xaa can be any naturally occurring amino acid
<220> FEATURE:
<221> NAME/KEY: misc_feature
<222> LOCATION: (46)..(46)
<223> OTHER INFORMATION: Xaa can be any naturally occurring amino acid
<220> FEATURE:
<221> NAME/KEY: misc_feature
<222> LOCATION: (49)..(49)
<223> OTHER INFORMATION: Xaa can be any naturally occurring amino acid
<220> FEATURE:
<221> NAME/KEY: misc_feature
<222> LOCATION: (51)..(52)
```

<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid

<400> SEQUENCE: 61

Asp Ile Val Met Thr Gln Ser Xaa Xaa Xaa Xaa Xaa Ser Val Gly
1               5                   10                  15

Asp Xaa Val Xaa Xaa Thr Cys Lys Ala Ser Gln Ser Val Asp Ser Asn
            20                  25                  30

Val Ala Trp Tyr Gln Gln Lys Pro Xaa Gln Xaa Pro Lys Xaa Leu Ile
        35                  40                  45

Xaa Ser Xaa Xaa Leu Arg Phe Ser Gly Val Pro Ala Arg Phe Xaa Gly
    50                  55                  60

Ser Gly Ser Gly Thr Asp Phe Thr Leu Thr Ile Ser Xaa Leu Gln Ser
65                  70                  75                  80

Glu Asp Xaa Ala Xaa Tyr Xaa Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 62
<211> LENGTH: 106
<212> TYPE: PRT
<213> ORGANISM: Homo sapiens

<400> SEQUENCE: 62

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 63
<211> LENGTH: 330
<212> TYPE: PRT
<213> ORGANISM: Homo sapiens

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 64
<211> LENGTH: 330
<212> TYPE: PRT
<213> ORGANISM: Homo sapiens

<400> SEQUENCE: 64

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 65
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)..(2)
<223> OTHER INFORMATION: Xaa is any amino acid
<220> FEATURE:
<221> NAME/KEY: VARIANT
<222> LOCATION: (4)..(4)
<223> OTHER INFORMATION: Xaa is any amino acid

<400> SEQUENCE: 65

Xaa Xaa Trp Xaa Ser
1               5
```

```
<210> SEQ ID NO 66
<211> LENGTH: 16
<212> TYPE: PRT
<213> ORGANISM: Artificial Seqeunce
<220> FEATURE:
<223> OTHER INFORMATION: Synthetic peptide
<220> FEATURE:
<221> NAME/KEY: VARIANT
<222> LOCATION: (2)..(16)
<223> OTHER INFORMATION: Xaa is any amino acid

<400> SEQUENCE: 66

Glu Xaa Xaa Xaa Xaa Xaa Xaa Xaa Xaa Xaa Xaa Xaa Xaa Xaa Xaa Xaa
1               5                   10                  15

<210> SEQ ID NO 67
<211> LENGTH: 12
<212> TYPE: PRT
<213> ORGANISM: Artificial Seqeunce
<220> FEATURE:
<223> OTHER INFORMATION: synthetic peptide
<220> FEATURE:
<221> NAME/KEY: VARIANT
<222> LOCATION: (4)..(12)
<223> OTHER INFORMATION: Xaa is any amino acid

<400> SEQUENCE: 67

Leu Tyr Tyr Xaa Xaa Xaa Xaa Xaa Xaa Xaa Xaa Xaa
1               5                   10

<210> SEQ ID NO 68
<211> LENGTH: 12
<212> TYPE: PRT
<213> ORGANISM: Artificial Seqeunce
<220> FEATURE:
<223> OTHER INFORMATION: synthetic peptide
<220> FEATURE:
<221> NAME/KEY: VARIANT
<222> LOCATION: (1)..(7)
<223> OTHER INFORMATION: Xaa is any amino acid
<220> FEATURE:
<221> NAME/KEY: VARIANT
<222> LOCATION: (10)..(10)
<223> OTHER INFORMATION: Xaa is any amino acid
<220> FEATURE:
<221> NAME/KEY: VARIANT
<222> LOCATION: (12)..(12)
<223> OTHER INFORMATION: Xaa is any amino acid

<400> SEQUENCE: 68

Xaa Xaa Xaa Xaa Xaa Xaa Xaa Ser Asn Xaa Ala Xaa
1               5                   10

<210> SEQ ID NO 69
<211> LENGTH: 7
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (5)..(5)
<223> OTHER INFORMATION: Xaa is any amino acid
<220> FEATURE:
<221> NAME/KEY: VARIANT
<222> LOCATION: (7)..(7)
<223> OTHER INFORMATION: Xaa is any amino acid
```

```
<400> SEQUENCE: 69

Ser Xaa Ser Leu Xaa Phe Xaa
1               5

<210> SEQ ID NO 70
<211> LENGTH: 11
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (2)..(2)
<223> OTHER INFORMATION: Xaa is any amino acid
<220> FEATURE:
<221> NAME/KEY: VARIANT
<222> LOCATION: (4)..(5)
<223> OTHER INFORMATION: Xaa is any amino acid
<220> FEATURE:
<221> NAME/KEY: VARIANT
<222> LOCATION: (7)..(7)
<223> OTHER INFORMATION: Xaa is any amino acid
<220> FEATURE:
<221> NAME/KEY: VARIANT
<222> LOCATION: (9)..(11)
<223> OTHER INFORMATION: Xaa is any amino acid

<400> SEQUENCE: 70

Gln Xaa Tyr Xaa Xaa Tyr Xaa Leu Xaa Xaa Xaa
1               5                   10

<210> SEQ ID NO 71
<211> LENGTH: 120
<212> TYPE: PRT
<213> ORGANISM: Artificial Sequence
<220> FEATURE:
<223> OTHER INFORMATION: peptide
<220> FEATURE:
<221> NAME/KEY: VARIANT
<222> LOCATION: (1)..(1)
<223> OTHER INFORMATION: Xaa is Gln or Glu
<220> FEATURE:
<221> NAME/KEY: VARIANT
<222> LOCATION: (5)..(5)
<223> OTHER INFORMATION: Xaa is Gln or Val
<220> FEATURE:
<221> NAME/KEY: VARIANT
<222> LOCATION: (6)..(6)
<223> OTHER INFORMATION: Xaa is Gln or Glu
<220> FEATURE:
<221> NAME/KEY: VARIANT
<222> LOCATION: (19)..(19)
<223> OTHER INFORMATION: Xaa is Lys or Arg
<220> FEATURE:
<221> NAME/KEY: VARIANT
<222> LOCATION: (27)..(27)
<223> OTHER INFORMATION: Xaa is Ile or Phe
<220> FEATURE:
<221> NAME/KEY: VARIANT
<222> LOCATION: (28)..(28)
<223> OTHER INFORMATION: Xaa is Asp or Thr
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: VARIANT
<222> LOCATION: (31)..(31)
<223> OTHER INFORMATION: Xaa is Arg or Asp
<220> FEATURE:
<221> NAME/KEY: VARIANT
<222> LOCATION: (39)..(39)
<223> OTHER INFORMATION: Xaa is Arg or Gln
<220> FEATURE:
<221> NAME/KEY: VARIANT
```

```
<222> LOCATION: (48)..(48)
<223> OTHER INFORMATION: Xaa is Ile or Val
<220> FEATURE:
<221> NAME/KEY: VARIANT
<222> LOCATION: (66)..(66)
<223> OTHER INFORMATION: Xaa is Asp or Gly
<220> FEATURE:
<221> NAME/KEY: VARIANT
<222> LOCATION: (67)..(67)
<223> OTHER INFORMATION: Xaa is Lys or Arg
<220> FEATURE:
<221> NAME/KEY: VARIANT
<222> LOCATION: (69)..(69)
<223> OTHER INFORMATION: Xaa is Ile or Thr
<220> FEATURE:
<221> NAME/KEY: VARIANT
<222> LOCATION: (84)..(84)
<223> OTHER INFORMATION: Xaa is Ser or Asn
<220> FEATURE:
<221> NAME/KEY: VARIANT
<222> LOCATION: (85)..(85)
<223> OTHER INFORMATION: Xaa is Lys or Ser
<220> FEATURE:
<221> NAME/KEY: VARIANT
<222> LOCATION: (86)..(86)
<223> OTHER INFORMATION: Xaa is Val or Leu
<220> FEATURE:
<221> NAME/KEY: VARIANT
<222> LOCATION: (88)..(88)
<223> OTHER INFORMATION: Xaa is Ser or Ala
<220> FEATURE:
<221> NAME/KEY: VARIANT
<222> LOCATION: (93)..(93)
<223> OTHER INFORMATION: Xaa is Leu or Val
<220> FEATURE:
<221> NAME/KEY: VARIANT
<222> LOCATION: (115)..(115)
<223> OTHER INFORMATION: Xaa is Ser or Leu

<400> SEQUENCE: 71

Xaa Val Gln Leu Xaa Xaa Ser Gly Gly Gly Leu Val Gln Pro Gly Gly
1               5                   10                  15

Ser Leu Xaa Leu Ser Cys Ala Ala Ser Gly Xaa Xaa Phe Xaa Xaa Tyr
            20                  25                  30

Trp Met Ser Trp Val Arg Xaa Ala Pro Gly Lys Gly Leu Glu Trp Xaa
        35                  40                  45

Gly Glu Ile Asn Pro Asp Ser Ser Thr Ile Asn Tyr Ala Pro Ser Leu
    50                  55                  60

Lys Xaa Xaa Phe Xaa Ile Ser Arg Asp Asn Ala Lys Asn Thr Leu Tyr
65                  70                  75                  80

Leu Gln Met Xaa Xaa Xaa Arg Xaa Glu Asp Thr Ala Xaa Tyr Tyr Cys
                85                  90                  95

Ala Ser Leu Tyr Tyr Asp Tyr Gly Asp Ala Met Asp Tyr Trp Gly Gln
            100                 105                 110

Gly Thr Xaa Val Thr Val Ser Ser
        115                 120

<210> SEQ ID NO 72
<211> LENGTH: 120
<212> TYPE: PRT
<213> ORGANISM: Artificial Sequence
<220> FEATURE:
<223> OTHER INFORMATION: peptide

<400> SEQUENCE: 72

Gln Val Gln Leu Gln Gln Ser Gly Gly Gly Leu Val Gln Pro Gly Gly
1               5                   10                  15

Ser Leu Lys Leu Ser Cys Ala Ala Ser Gly Ile Asp Phe Ser Arg Tyr
```

```
                    20                  25                  30
Trp Met Ser Trp Val Arg Arg Ala Pro Gly Lys Gly Leu Glu Trp Ile
            35                  40                  45
Gly Glu Ile Asn Pro Asp Ser Ser Thr Ile Asn Tyr Ala Pro Ser Leu
        50                  55                  60
Lys Asp Lys Phe Ile Ile Ser Arg Asp Asn Ala Lys Asn Thr Leu Tyr
65                  70                  75                  80
Leu Gln Met Ser Lys Val Arg Ser Glu Asp Thr Ala Leu Tyr Tyr Cys
                85                  90                  95
Ala Ser Leu Tyr Tyr Asp Tyr Gly Asp Ala Met Asp Tyr Trp Gly Gln
                100                 105                 110
Gly Thr Ser Val Thr Val Ser Ser
            115                 120

<210> SEQ ID NO 73
<211> LENGTH: 120
<212> TYPE: PRT
<213> ORGANISM: Artificial Sequence
<220> FEATURE:
<223> OTHER INFORMATION: peptide

<400> SEQUENCE: 73

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Trp Met Ser Trp Val Arg Gln Ala Pro Gly Lys Gly Leu Glu Trp Val
            35                  40                  45
Gly Glu Ile Asn Pro Asp Ser Ser Thr Ile Asn Tyr Ala Pro Ser Leu
        50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Leu Tyr Tyr Asp Tyr Gly Asp Ala Met Asp Tyr Trp Gly Gln
                100                 105                 110
Gly Thr Leu Val Thr Val Ser Ser
            115                 120

<210> SEQ ID NO 74
<211> LENGTH: 120
<212> TYPE: PRT
<213> ORGANISM: Artificial sequence
<220> FEATURE:
<223> OTHER INFORMATION: peptide

<400> SEQUENCE: 74

Glu Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Trp Met Ser Trp Val Arg Gln Ala Pro Gly Lys Gly Leu Glu Trp Val
            35                  40                  45
Gly Glu Ile Asn Pro Asp Ser Ser Thr Ile Asn Tyr Ala Pro Ser Leu
        50                  55                  60
Lys Gly Arg Phe Thr Ile Ser Arg Asp Asn Ala Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 75
<211> LENGTH: 120
<212> TYPE: PRT
<213> ORGANISM: Artificial sequence
<220> FEATURE:
<223> OTHER INFORMATION: peptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ser Trp Val Arg Gln Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 76
<211> LENGTH: 120
<212> TYPE: PRT
<213> ORGANISM: Artificial sequence
<220> FEATURE:
<223> OTHER INFORMATION: peptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 77
```

<211> LENGTH: 120
<212> TYPE: PRT
<213> ORGANISM: Artificial Sequence
<220> FEATURE:
<223> OTHER INFORMATION: peptide

<400> SEQUENCE: 77

Glu Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Ser Asp Tyr
            20                  25                  30
Trp Met Ser Trp Val Arg Gln Ala Pro Gly Lys Gly Leu Glu Trp Val
        35                  40                  45
Gly Glu Ile Asn Pro Asp Ser Ser Thr Ile Asn Tyr Ala Pro Ser Leu
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Leu Tyr Tyr Asp Tyr Gly Asp Ala Met Asp Tyr Trp Gly Gln
            100                 105                 110
Gly Thr Leu Val Thr Val Ser Ser
        115                 120

<210> SEQ ID NO 78
<211> LENGTH: 120
<212> TYPE: PRT
<213> ORGANISM: Artificial sequence
<220> FEATURE:
<223> OTHER INFORMATION: peptide

<400> SEQUENCE: 78

Glu Val Gln Leu Val Gln Ser Gly Gly Gly Leu Val Gln Pro Gly Gly
1               5                   10                  15
Ser Leu Arg Leu Ser Cys Ala Ala Ser Gly Phe Thr Phe Asp Asp Tyr
            20                  25                  30
Trp Met Ser Trp Val Arg Arg Ala Pro Gly Lys Gly Leu Glu Trp Val
        35                  40                  45
Gly Glu Ile Asn Pro Asp Ser Ser Thr Ile Tyr Tyr Ala Pro Ser Leu
    50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Ser Leu Tyr Tyr Asp Tyr Gly Asp Ala Met Asp Tyr Trp Gly Gln
            100                 105                 110
Gly Thr Leu Val Thr Val Ser Ser
        115                 120

<210> SEQ ID NO 79
<211> LENGTH: 120
<212> TYPE: PRT
<213> ORGANISM: Artificial Seqeunce
<220> FEATURE:
<223> OTHER INFORMATION: peptide

<400> SEQUENCE: 79

Glu Val Gln Leu Val Glu Ser Gly Gly Gly Leu Val Gln Pro Gly Gly
1               5                   10                  15

-continued

```
Ser Leu Arg Leu Ser Cys Ala Ala Ser Gly Phe Thr Phe Ser Asp Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 80
<211> LENGTH: 120
<212> TYPE: PRT
<213> ORGANISM: Artificial seqeunce
<220> FEATURE:
<223> OTHER INFORMATION: peptide

<400> SEQUENCE: 80

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Trp Met Ser Trp Val Arg Arg Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Leu Tyr Tyr Asp Tyr Gly Asp Ala Met Asp Tyr Trp Gly Gln
            100                 105                 110

Gly Thr Leu Val Thr Val Ser Ser
        115                 120

<210> SEQ ID NO 81
<211> LENGTH: 108
<212> TYPE: PRT
<213> ORGANISM: Artificial seqeunce
<220> FEATURE:
<223> OTHER INFORMATION: peptide
<220> FEATURE:
<221> NAME/KEY: VARIANT
<222> LOCATION: (8)..(8)
<223> OTHER INFORMATION: Xaa is Gln or Pro
<220> FEATURE:
<221> NAME/KEY: VARIANT
<222> LOCATION: (9)..(9)
<223> OTHER INFORMATION: Xaa is Arg or Ala
<220> FEATURE:
<221> NAME/KEY: VARIANT
<222> LOCATION: (10)..(10)
<223> OTHER INFORMATION: Xaa is Phe or Thr
<220> FEATURE:
<221> NAME/KEY: VARIANT
<222> LOCATION: (11)..(11)
<223> OTHER INFORMATION: Xaa is Met or Leu
<220> FEATURE:
```

```
<221> NAME/KEY: VARIANT
<222> LOCATION: (12)..(12)
<223> OTHER INFORMATION: Xaa is Thr or Ser
<220> FEATURE:
<221> NAME/KEY: VARIANT
<222> LOCATION: (13)..(13)
<223> OTHER INFORMATION: Xaa is Thr or Val
<220> FEATURE:
<221> NAME/KEY: VARIANT
<222> LOCATION: (18)..(18)
<223> OTHER INFORMATION: Xaa is Arg pr Glu
<220> FEATURE:
<221> NAME/KEY: VARIANT
<222> LOCATION: (20)..(20)
<223> OTHER INFORMATION: Xaa is Ser or Thr
<220> FEATURE:
<221> NAME/KEY: VARIANT
<222> LOCATION: (21)..(21)
<223> OTHER INFORMATION: Xaa is Val or Leu
<220> FEATURE:
<221> NAME/KEY: VARIANT
<222> LOCATION: (41)..(41)
<223> OTHER INFORMATION: Xaa is Arg or Gly
<220> FEATURE:
<221> NAME/KEY: VARIANT
<222> LOCATION: (43)..(43)
<223> OTHER INFORMATION: Xaa is Ser or Ala
<220> FEATURE:
<221> NAME/KEY: VARIANT
<222> LOCATION: (46)..(46)
<223> OTHER INFORMATION: Xaa is Ala or Leu
<220> FEATURE:
<221> NAME/KEY: VARIANT
<222> LOCATION: (49)..(49)
<223> OTHER INFORMATION: Xaa is Phe or Tyr
<220> FEATURE:
<221> NAME/KEY: VARIANT
<222> LOCATION: (51)..(51)
<223> OTHER INFORMATION: Xaa is Ala or Asp
<220> FEATURE:
<221> NAME/KEY: VARIANT
<222> LOCATION: (52)..(52)
<223> OTHER INFORMATION: Xaa is Ser or Asp
<220> FEATURE:
<221> NAME/KEY: VARIANT
<222> LOCATION: (63)..(63)
<223> OTHER INFORMATION: Xaa is Thr or Ser
<220> FEATURE:
<221> NAME/KEY: VARIANT
<222> LOCATION: (77)..(77)
<223> OTHER INFORMATION: Xaa is Asn or Ser
<220> FEATURE:
<221> NAME/KEY: VARIANT
<222> LOCATION: (83)..(83)
<223> OTHER INFORMATION: Xaa is Leu or Phe
<220> FEATURE:
<221> NAME/KEY: VARIANT
<222> LOCATION: (85)..(85)
<223> OTHER INFORMATION: Xaa is Glu or Val
<220> FEATURE:
<221> NAME/KEY: VARIANT
<222> LOCATION: (87)..(87)
<223> OTHER INFORMATION: Xaa is Phe or Tyr

<400> SEQUENCE: 81

Asp Ile Val Met Thr Gln Ser Xaa Xaa Xaa Xaa Xaa Ser Val Gly
1               5                   10                  15

Asp Xaa Val Xaa Xaa Thr Cys Lys Ala Ser Gln Ser Val Asp Ser Asn
            20                  25                  30

Val Ala Trp Tyr Gln Gln Lys Pro Xaa Gln Xaa Pro Lys Xaa Leu Ile
                35                  40                  45

Xaa Ser Xaa Xaa Leu Arg Phe Ser Gly Val Pro Ala Arg Phe Xaa Gly
    50                  55                  60

Ser Gly Ser Gly Thr Asp Phe Thr Leu Thr Ile Ser Xaa Leu Gln Ser
```

```
                65                  70                  75                  80
Glu Asp Xaa Ala Xaa Tyr Xaa Cys Gln Gln Tyr Asn Asn Tyr Pro Leu
                    85                  90                  95

Thr Phe Gly Ala Gly Thr Lys Leu Glu Leu Lys Arg
                100                 105

<210> SEQ ID NO 82
<211> LENGTH: 108
<212> TYPE: PRT
<213> ORGANISM: Artificial sequence
<220> FEATURE:
<223> OTHER INFORMATION: peptide

<400> SEQUENCE: 82

Asp Ile Val Met Thr Gln Ser Gln Arg Phe Met Thr Thr Ser Val Gly
1               5                   10                  15

Asp Arg Val Ser Val Thr Cys Lys Ala Ser Gln Ser Val Asp Ser Asn
                20                  25                  30

Val Ala Trp Tyr Gln Gln Lys Pro Arg Gln Ser Pro Lys Ala Leu Ile
            35                  40                  45

Phe Ser Ala Ser Leu Arg Phe Ser Gly Val Pro Ala Arg Phe Thr Gly
        50                  55                  60

Ser Gly Ser Gly Thr Asp Phe Thr Leu Thr Ile Ser Asn Leu Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg
                100                 105

<210> SEQ ID NO 83
<211> LENGTH: 108
<212> TYPE: PRT
<213> ORGANISM: Artificial sequence
<220> FEATURE:
<223> OTHER INFORMATION: peptide

<400> SEQUENCE: 83

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ala Pro Lys Leu Leu Ile
            35                  40                  45

Tyr Ser Asp Asp Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
                100                 105

<210> SEQ ID NO 84
<211> LENGTH: 108
<212> TYPE: PRT
<213> ORGANISM: Artificial sequence
<220> FEATURE:
<223> OTHER INFORMATION: peptide

<400> SEQUENCE: 84
```

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ser Pro Lys Leu Leu Ile
            35                  40                  45

Tyr Ser Asp Asp Leu Arg Phe Ser Gly Val Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
                100                 105
```

<210> SEQ ID NO 85
<211> LENGTH: 108
<212> TYPE: PRT
<213> ORGANISM: Artificial sequence
<220> FEATURE:
<223> OTHER INFORMATION: peptide

<400> SEQUENCE: 85

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ala Pro Lys Ala Leu Ile
            35                  40                  45

Tyr Ser Asp Asp Leu Arg Phe Ser Gly Val Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
                100                 105
```

<210> SEQ ID NO 86
<211> LENGTH: 108
<212> TYPE: PRT
<213> ORGANISM: Artificial sequence
<220> FEATURE:
<223> OTHER INFORMATION: peptide

<400> SEQUENCE: 86

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ala Pro Lys Leu Leu Ile
            35                  40                  45

Tyr Ser Ala Ser Leu Arg Phe Ser Gly Val Pro Ala Arg Phe Ser Gly
50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
```

```
            85                  90                  95
Thr Phe Gly Ala Gly Thr Lys Leu Glu Leu Lys Arg
            100                 105

<210> SEQ ID NO 87
<211> LENGTH: 108
<212> TYPE: PRT
<213> ORGANISM: Artificial sequence
<220> FEATURE:
<223> OTHER INFORMATION: peptide

<400> SEQUENCE: 87

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 88
<211> LENGTH: 108
<212> TYPE: PRT
<213> ORGANISM: Artificial Sequence
<220> FEATURE:
<223> OTHER INFORMATION: peptide

<400> SEQUENCE: 88

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 89
<211> LENGTH: 108
<212> TYPE: PRT
<213> ORGANISM: Artificial sequence
<220> FEATURE:
<223> OTHER INFORMATION: peptide

<400> SEQUENCE: 89

Asp Ile Val Met Thr Gln Ser Pro Ala Thr Leu Ser Val Ser Val Gly
1               5                   10                  15
```

```
Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105
```

<210> SEQ ID NO 90
<211> LENGTH: 108
<212> TYPE: PRT
<213> ORGANISM: Artificial sequence
<220> FEATURE:
<223> OTHER INFORMATION: peptide

<400> SEQUENCE: 90

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105
```

<210> SEQ ID NO 91
<211> LENGTH: 108
<212> TYPE: PRT
<213> ORGANISM: Artificial sequence
<220> FEATURE:
<223> OTHER INFORMATION: peptide

<400> SEQUENCE: 91

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
```

100                 105

<210> SEQ ID NO 92
<211> LENGTH: 108
<212> TYPE: PRT
<213> ORGANISM: Artificial sequence
<220> FEATURE:
<223> OTHER INFORMATION: peptide

<400> SEQUENCE: 92

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 93
<211> LENGTH: 108
<212> TYPE: PRT
<213> ORGANISM: Artificial sequence
<220> FEATURE:
<223> OTHER INFORMATION: peptide

<400> SEQUENCE: 93

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 94
<211> LENGTH: 108
<212> TYPE: PRT
<213> ORGANISM: Artificial sequence
<220> FEATURE:
<223> OTHER INFORMATION: peptide

<400> SEQUENCE: 94

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 95
<211> LENGTH: 108
<212> TYPE: PRT
<213> ORGANISM: Artificial sequence
<220> FEATURE:
<223> OTHER INFORMATION: peptide

<400> SEQUENCE: 95

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 96
<211> LENGTH: 108
<212> TYPE: PRT
<213> ORGANISM: Artificial sequence
<220> FEATURE:
<223> OTHER INFORMATION: peptide

<400> SEQUENCE: 96

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Leu Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

```
<210> SEQ ID NO 97
<211> LENGTH: 108
<212> TYPE: PRT
<213> ORGANISM: Artificial sequence
<220> FEATURE:
<223> OTHER INFORMATION: peptide

<400> SEQUENCE: 97

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 98
<211> LENGTH: 108
<212> TYPE: PRT
<213> ORGANISM: Artificial sequence
<220> FEATURE:
<223> OTHER INFORMATION: peptide

<400> SEQUENCE: 98

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Tyr Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 99
<211> LENGTH: 108
<212> TYPE: PRT
<213> ORGANISM: Artificial sequence
<220> FEATURE:
<223> OTHER INFORMATION: peptide

<400> SEQUENCE: 99

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45
```

```
Phe Ser Asp Asp Leu Arg Phe Ser Gly Val Pro Ala Arg Phe Ser Gly
            50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 100
<211> LENGTH: 108
<212> TYPE: PRT
<213> ORGANISM: Artificial sequence
<220> FEATURE:
<223> OTHER INFORMATION: peptide

<400> SEQUENCE: 100

Asp Ile Val Met Thr Gln Ser Pro Ala Thr Leu Ser Val Ser Val Gly
 1               5                  10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ser Pro Lys Leu Leu Ile
            35                  40                  45

Phe Ser Asp Asp Leu Arg Phe Ser Gly Val Pro Ala Arg Phe Ser Gly
            50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 101
<211> LENGTH: 108
<212> TYPE: PRT
<213> ORGANISM: Artificial sequence
<220> FEATURE:
<223> OTHER INFORMATION: peptide

<400> SEQUENCE: 101

Asp Ile Val Met Thr Gln Ser Pro Ala Thr Leu Ser Val Ser Val Gly
 1               5                  10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ser Pro Lys Ala Leu Ile
            35                  40                  45

Phe Ser Asp Asp Leu Arg Phe Ser Gly Val Pro Ala Arg Phe Ser Gly
            50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 102
<211> LENGTH: 108
<212> TYPE: PRT
```

<213> ORGANISM: Artificial sequence
<220> FEATURE:
<223> OTHER INFORMATION: peptide

<400> SEQUENCE: 102

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 103
<211> LENGTH: 108
<212> TYPE: PRT
<213> ORGANISM: Artificial sequence
<220> FEATURE:
<223> OTHER INFORMATION: peptide

<400> SEQUENCE: 103

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 104
<211> LENGTH: 108
<212> TYPE: PRT
<213> ORGANISM: Artificial sequence
<220> FEATURE:
<223> OTHER INFORMATION: peptide

<400> SEQUENCE: 104

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ser Pro Lys Ala Leu Ile
        35                  40                  45

Phe Ser Asp Asp Leu Arg Phe Ser Gly Val Pro Ala Arg Phe Ser Gly
    50                  55                  60

-continued

```
Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                 85                  90                  95

Thr Phe Gly Ala Gly Thr Lys Leu Glu Leu Lys Arg
            100                 105

<210> SEQ ID NO 105
<211> LENGTH: 108
<212> TYPE: PRT
<213> ORGANISM: Artificial sequence
<220> FEATURE:
<223> OTHER INFORMATION: peptide

<400> SEQUENCE: 105

Asp Ile Val Met Thr Gln Ser Pro Ala Thr Leu Ser Val Ser Val Gly
 1               5                  10                  15

Asp Glu Val Thr Leu Thr Cys Lys Ala Ser Gln Ser Val Asp Ser Asn
                 20                  25                  30

Val Ala Trp Tyr Gln Gln Lys Pro Gly Gln Ser Pro Lys Leu Leu Ile
             35                  40                  45

Phe Ser Ala Ser Leu Arg Phe Ser Gly Val Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Val Tyr Tyr Cys Gln Gln Tyr Asn Asn Tyr Pro Leu
                 85                  90                  95

Thr Phe Gly Ala Gly Thr Lys Leu Glu Leu Lys Arg
            100                 105

<210> SEQ ID NO 106
<211> LENGTH: 108
<212> TYPE: PRT
<213> ORGANISM: Artificial sequence
<220> FEATURE:
<223> OTHER INFORMATION: peptide

<400> SEQUENCE: 106

Asp Ile Val Met Thr Gln Ser Pro Ala Thr Leu Ser Val Ser Val Gly
 1               5                  10                  15

Asp Glu Val Thr Leu Thr Cys Lys Ala Ser Gln Ser Val Asp Ser Asn
                 20                  25                  30

Val Ala Trp Tyr Gln Gln Lys Pro Gly Gln Ser Pro Lys Leu Leu Ile
             35                  40                  45

Phe Ser Asp Asp Leu Arg Phe Ser Gly Val Pro Ala Arg Phe Ser Gly
 50                  55                  60

Ser Gly Ser Gly Thr Asp Phe Thr Leu Thr Ile Ser Ser Leu Gln Ser
 65                  70                  75                  80

Glu Asp Phe Ala Glu Tyr Tyr Cys Gln Gln Tyr Asn Asn Tyr Pro Leu
                 85                  90                  95

Thr Phe Gly Ala Gly Thr Lys Leu Glu Leu Lys Arg
            100                 105

<210> SEQ ID NO 107
<211> LENGTH: 108
<212> TYPE: PRT
<213> ORGANISM: Artificial sequence
<220> FEATURE:
<223> OTHER INFORMATION: peptide
```

<400> SEQUENCE: 107

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 108
<211> LENGTH: 108
<212> TYPE: PRT
<213> ORGANISM: Artificial sequence
<220> FEATURE:
<223> OTHER INFORMATION: peptide

<400> SEQUENCE: 108

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Ala Leu Ile
        35                  40                  45

Phe Ser Asp Asp Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 109
<211> LENGTH: 108
<212> TYPE: PRT
<213> ORGANISM: Artificial sequence
<220> FEATURE:
<223> OTHER INFORMATION: peptide

<400> SEQUENCE: 109

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
            20                  25                  30

Val Ala Trp Tyr Gln Gln Lys Pro Gly Gln Ala Pro Lys Leu Leu Ile
        35                  40                  45

Phe Ser Ala Ser Leu Arg Phe Ser Gly Val Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 110
<211> LENGTH: 108
<212> TYPE: PRT
<213> ORGANISM: Artificial sequence
<220> FEATURE:
<223> OTHER INFORMATION: peptide

<400> SEQUENCE: 110

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ser Pro Lys Ala Leu Ile
            35                  40                  45

Phe Ser Ala Ser Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 111
<211> LENGTH: 108
<212> TYPE: PRT
<213> ORGANISM: Artificial sequence
<220> FEATURE:
<223> OTHER INFORMATION: peptide

<400> SEQUENCE: 111

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ser Pro Lys Ala Leu Ile
            35                  40                  45

Phe Ser Asp Asp Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
            100                 105

<210> SEQ ID NO 112
<211> LENGTH: 108
<212> TYPE: PRT
<213> ORGANISM: Artificial sequence
<220> FEATURE:
<223> OTHER INFORMATION: peptide

<400> SEQUENCE: 112

```
Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ser Pro Lys Leu Leu Ile
            35                  40                  45

Phe Ser Ala Ser Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
                100                 105

<210> SEQ ID NO 113
<211> LENGTH: 108
<212> TYPE: PRT
<213> ORGANISM: Artificial sequence
<220> FEATURE:
<223> OTHER INFORMATION: peptide

<400> SEQUENCE: 113

Asp Ile Val Met Thr Gln Ser Pro Ala Thr Leu Ser Val Ser Val Gly
1               5                   10                  15

Asp Glu Val Thr Leu Thr Cys Lys Ala Ser Gln Ser Val Asp Ser Asn
                20                  25                  30

Val Ala Trp Tyr Gln Gln Lys Pro Gly Gln Ala Pro Lys Ala Leu Ile
            35                  40                  45

Phe Ser Ala Ser Leu Arg Phe Ser Gly Val Pro Ala Arg Phe Ser Gly
        50                  55                  60

Ser Gly Ser Gly Thr Asp Phe Thr Leu Thr Ile Ser Ser Leu Gln Ser
65                  70                  75                  80

Glu Asp Phe Ala Glu Tyr Tyr Cys Gln Gln Tyr Asn Asn Tyr Pro Leu
                85                  90                  95

Thr Phe Gly Ala Gly Thr Lys Leu Glu Leu Lys Arg
                100                 105
```

ANTIBODY THAT BINDS CD269 (BCMA) SUITABLE FOR USE IN THE TREATMENT OF PLASMA CELL DISEASES SUCH AS MULTIPLE MYELOMA AND AUTOIMMUNE DISEASES

The invention relates to antibodies or antibody fragments that bind CD269 (BCMA), thereby disrupting the interaction between CD269 and its native ligands (BAFF and APRIL), and their use in the treatment of plasma cell-mediated diseases such as multiple myeloma and autoimmune diseases.

REFERENCE TO SEQUENCE LISTING

The present application is filed along with a Sequence Listing in electronic format. The Sequence Listing is provided as a file entitled 33105764_1.TXT, created Jul. 8, 2020, which is approximately 110 KB in size. The information in the electronic format of the Sequence Listing is incorporated herein by reference in its entirety.

BACKGROUND OF THE INVENTION

The B cell maturation antigen (BCMA) is member 17 of the tumor necrosis factor receptor superfamily (TNFRSF). Its native ligands are the B cell activating factor (BAFF; also called BLyS or TALL-1, TNFSF13B) and a proliferation-inducing ligand (APRIL, TNFSF13, CD256) (Mackay et al. (2003) Annu Rev Immunol 21:231-264) which are ultimately involved (through interaction with further ligands) in regulating various aspects of humoral immunity, B cell development, and homeostasis. The affinity for BAFF lies in the low micromolar range whereas APRIL binds nearly 100 fold tighter to BCMA (Bossen et al. (2006) Semin Immunol 18:263-275). Expression of BCMA is restricted to the B cell lineage where it is predominantly expressed on plasma blasts and plasma cells but is absent from naive B cells, germinal center B cells and memory B cells (Darce et al. (2007) J Immunol 179:7276-7286; Benson et al. (2008) J Immunol 180:3655-3659; Good et al. (2009) J Immunol 182:890-901).

BCMA expression is important for the survival of long-lived, sessile plasma cells in the bone marrow (O'Connor et al. (2004) J Exp Med 199:91-98). Consequently, BCMA-deficient mice show reduced plasma cell numbers in the bone marrow whereas the level of plasma cells in the spleen in unaffected (Peperzak et al. (2013) Nat Immunol [Epub 2013 Feb. 3, 10.1038/ni.2527]). The differentiation of mature B cells into plasma cells is normal in BCMA knockout mice (Schiemann et al. (2001) Science 293:2111-2114; Xu et al. (2001) Mol Cell Biol 21:4067-4074). The binding of BAFF or APRIL to BCMA triggers NF-κB activation (Hatzoglou et al. (2000) J Immunol 165:1322-1330), which induces upregulation of anti-apoptotic Bcl-2 members such as Bcl-xL or Bcl-2 and Mcl-1 (Peperzak et al. (2013) Nat Immunol [Epub 2013 Feb. 3, 10.1038/ni.2527]).

BCMA is also highly expressed on malignant plasma cells, for example in multiple myeloma, (MM), which is a B cell non-Hodgkin lymphoma of the bone marrow, and plasma cell leukemia (PCL), which is more aggressive than MM and constitutes around 4% of all cases of plasma cell disorders. In addition to MM and PCL, BCMA has also been detected on Hodgkin and Reed-Sternberg cells in patients suffering from Hodgkin's lymphoma (Chiu et al. (2007) Blood 109:729-739). Similar to its function on plasma cells, ligand binding to BCMA has been shown to modulate the growth and survival of multiple myeloma cells expressing BCMA (Novak et al. (2004) Blood 103:689-694). Signaling of BAFF and APRIL via BCMA are considered as pro-survival factors for malignant plasma cells; hence, the depletion of BCMA-positive tumour cells and/or the disruption of ligand-receptor interaction should improve the therapeutic outcome for multiple myeloma and autoantibody-dependent autoimmune diseases.

There are presently various approaches available for the treatment of multiple myeloma (Raab et al. (2009) Lancet 374:324-339). Chemotherapy leads in most subjects only to partial control of multiple myeloma; only rarely does chemotherapy lead to complete remission. Combination approaches are therefore often applied, commonly involving an additional administration of corticosteroids, such as dexamethasone or prednisone. Corticosteroids are however plagued by side effects, such as reduced bone density. Stem cell transplantation has also been proposed, using one's own stem cells (autologous) or using cells from a close relative or matched unrelated donor (allogeneic). In multiple myeloma, most transplants performed are of the autologous kind. Such transplants, although not curative, have been shown to prolong life in selected patients (Suzuki (2013) Jpn J Clin Oncol 43:116-124). Alternatively thalidomide and derivatives thereof have recently been applied in treatment but are also associated with sub-optimal success rates and high costs. More recently, the proteasome inhibitor bortezomib (PS-341) has been approved for the treatment of relapsed and refractory MM and was used in numerous clinical trials alone or in combination with established drugs resulting in an encouraging clinical outcome (Richardson et al. (2003) New Engl J Med 348:2609-2617; Kapoor et al. (2012) Semin Hematol 49:228-242). Therapeutic approaches are often combined. The costs for such combined treatments are correspondingly high and success rates still leave significant room for improvement. The combination of treatment options is also not ideal due to an accumulation of side effects if multiple medicaments are used simultaneously. Novel approaches for the treatment of plasma cell diseases, in particular multiple myeloma, are required.

The ability to specifically target plasma cells is also of great benefit for the treatment of autoimmune diseases. Conventional therapy for autoimmune conditions such as systemic lupus erythematosus (SLE) and rheumatic arthritis (RA), in which autoreactive antibodies are crucial to disease pathology, depend on the severity of the symptoms and the circumstances of the patient (Scott et al. (2010) Lancet 376:1094-1108, D'Cruz et al. (2007) Lancet 369, 587-596). In general, mild forms of disease are first treated with nonsteroidal anti-inflammatory drugs (NSAID) or disease-modifying anti-rheumatic drugs (DMARD). More severe forms of SLE, involving organ dysfunction due to active disease, usually are treated with steroids in conjunction with strong immunosuppressive agents such as cyclophosphamide, a cytotoxic agent that targets cycling cells. Only recently Belimumab, an antibody targeting the cytokine BAFF, which is found at elevated levels in serum of patients with autoimmune diseases, received approval by the Food and Drug Administration (FDA) for its use in SLE. However, only newly formed B cells rely on BAFF for survival in humans, whereas memory B cells and plasma cells are less susceptible to selective BAFF inhibition (Jacobi et al. (2010) Arthritis Rheum 62:201-210). For rheumatoid arthritis, TNF inhibitors were the first licensed biological agents, followed by abatacept, rituximab, and tocilizumab and others: they suppress key inflammatory pathways involved in joint inflammation and destruction, which, however, comes at the price of an elevated infection risk due to relative immunosuppression (Chan et al. (2010) Nat Rev Immunol 10:301-316, Keyser (2011) Curr Rheumatol Rev 7:77-87). Despite the approval of these biologicals, patients suffering from RA and SLE often show a persistence of autoimmune markers, which is most likely related to the presence of long-lived, sessile plasma cells in bone marrow that resist e.g. CD20-mediated ablation by rituximab and high dosage glucocorticoid and cyclophosphamid therapy. Current strategies in SLE include a "reset" of the immune system by immunoablation and autologous stem cell transplantation though the risk for transplant-related mortality remains a serious concern (Farge et al. (2010) Haematologica 95:284-292). The use of proteasome inhibitors such as Bortezomib might be an alternative strategy for plasma cell depletion: owing to the high rate of protein synthesis and the limited proteolytic capacity, plasma cells are hypersensitive to proteasome inhibitors. Bortezomib has recently been approved for the treatment of relapsed multiple myeloma and a recent study in mice with lupus-like disease showed that bortezomib depletes plasma cells and protects mice with lupus-like disease from nephritis (Neubert et al. (2008) Nat Med 14:748-755). However, proteasome inhibitors do not specifically act on plasma cells and the incidence of adverse effects such as peripheral neuropathy is high (Arastu-Kapur et al. (2011) Clin Cancer Res 17:2734-2743).

Therapeutic antibodies can act through several mechanisms upon binding to their target. The binding itself can trigger signal transduction, which can lead to programmed cell death (Chavez-Galan et al. (2009) Cell Mol Immunol 6:15-25). It can also block the interaction of a receptor with its ligand by either binding to the receptor or the ligand. This interruption can cause apoptosis if signals important for survival are affected (Chiu et al. (2007) Blood 109:729-739). With regard to cell-depletion there are two major effector mechanisms known. The first is the complement-dependent cytotoxicity (CDC) towards the target cell. There are three different pathways known. However, in the case of antibodies the important pathway for CDC is the classical pathway which is initiated through the binding of C1q to the constant region of IgG or IgM (Wang and Weiner (2008) Expert Opin Biol Ther 8:759-768).

The second mechanism is called antibody-dependent cellular cytotoxicity (ADCC). This effector function is characterized by the recruitment of immune cells which express Fc-receptors for the respective isotype of the antibody. ADCC is largely mediated by activating Fc-gamma receptors (FcγR) which are able to bind to IgG molecules either alone or as immune complexes. Mice exhibit three (FcγRI, FcγRIII and FcγRIV) and humans five (FcγRI, FcγRIIA, FcγRIIC, FcγRIIIA and FcγRIIIB) activating Fcγ-receptors. These receptors are expressed on innate immune cells like granulocytes, monocytes, macrophages, dendritic cells and natural killer cells and therefore link the innate with the adaptive immune system. Depending on the cell type there are several modes of action of FcgR-bearing cells upon recognition of an antibody-marked target cell. Granulocytes generally release vasoactive and cytotoxic substances or chemoattractants but are also capable of phagocytosis. Monocytes and macrophages respond with phagocytosis, oxidative burst, cytotoxicity or the release of pro-inflammatory cytokines whereas Natural killer cells release granzymes and perforin and can also trigger cell death through the interaction with FAS on the target cell and their Fas ligand (Nimmerjahn and Ravetch (2008) Nat Rev Immunol 8:34-47; Wang and Weiner (2008) Expert Opin Biol Ther 8:759-768; Chavez-Galan et al. (2009) Cell Mol Immunol 6:15-25).

Antibodies which bind CD269 (BCMA) and their use in the treatment of various B-cell related medical disorders are described in the art. Ryan et al (Molecular Cancer Therapeutics, 2007 6(11), 3009) describe an anti-BCMA antibody obtained via vaccination in rats using a peptide of amino acids 5 to 54 of the BCMA protein. The antibody described therein binds BCMA, blocks APRIL-dependent NF-KB activation and induces ADCC. No details are provided on the specific epitope of the antibody.

WO 2012/163805 describes BCMA binding proteins, such as chimeric and humanised antibodies, their use to block BAFF and/or APRIL interaction with BCMA and their potential use in treating plasma cell malignancies such as multiple myeloma. The antibody disclosed therein was obtained via vaccination in mouse using a recombinant peptide of amino acids 4 to 53 of the BCMA protein. WO 2010/104949 also discloses various antibodies that bind preferably the extracellular domain of BCMA and their use in treating B cell mediated medical conditions and disorders. No details are provided on the specific epitope of the antibodies.

WO 2002/066516 discloses bivalent antibodies that bind both BCMA and TACI and their potential use in the treatment of autoimmune diseases and B cell cancers. An undefined extracellular domain of BCMA is used to generate the anti-BCMA portion of the antibodies described therein. WO 2012/066058 discloses bivalent antibodies that bind both BCMA and CD3 and their potential use in the treatment of B cell related medical disorders. Details regarding the binding properties and specific epitopes of the antibodies are not provided in either disclosure.

WO 2012/143498 discloses methods for the stratification of multiple myeloma patients involving the use of anti-BCMA antibodies. Preferred antibodies are those known as "Vicky-1" (IgG1 subtype from GeneTex) and "Mab 193" (IgG2a subtype from R&D Systems). Details regarding the binding properties and specific epitopes of the antibodies are not provided.

SUMMARY OF THE INVENTION

In light of the prior art the technical problem underlying the invention was the provision of an agent suitable for treating diseases associated with pathogenic plasma cells, such as multiple myeloma and autoimmune diseases. This problem is solved by the features of the independent claims. Preferred embodiments of the present invention are provided by the dependent claims.

Therefore, an object of the invention is to provide an isolated antibody or antibody fragment that binds CD269 (BCMA), in particular an epitope of the extracellular domain of CD269 (BCMA).

Preferred Embodiments Regarding the Antibody Epitope

The invention therefore relates to an isolated antibody or antibody fragment that binds CD269 (BCMA), wherein the antibody binds an epitope comprising one or more amino acids of residues 13 to 32 (amino acids 13 to 32 are shown in SEQ ID No. 14) of CD269 (BCMA).

The amino acid sequence of residues 13 to 32 are shown in SEQ ID No. 14. The N-terminus sequence of CD269 is provided in SEQ ID No. 13. The extracellular domain of CD269 is provided as SEQ ID No. 12.

An antigen comprising the extracellular domain of CD269 according to SEQ ID No. 12 was used in vaccination in order to generate the binding specificity of the antibody of the present invention. Use of the entire CD269 protein, or fragments thereof comprising either a membrane-bound or intracellular domain, as an antigen during antibody generation could produce antibodies that bind concealed or intracellular domains of CD269, thereby rendering such agents unsuitable or disadvantageous for therapeutic application. The antibodies of the present invention are therefore defined by their binding to the extracellular portion of CD269. The specific epitope within the extracellular domain also represents a preferred novel and unexpected characterising feature of the invention.

Fab fragments prepared from one embodiment of the invention were crystallized in complex with the purified BCMA extracellular domain and the complex structure solved. The structural analysis has revealed detailed information of the epitope of the antibody of the present invention and its biological relevance. The binding of an epitope comprising one or more amino acids of residues 13 to 32 of CD269 (BCMA) of the extracellular domain by the antibody of the present invention is an advantageous property, as this region shows a significant overlap with the binding sites of BAFF and APRIL, the two natural ligands of CD269. No anti-CD269 antibody described in art to date has shown such comprehensive overlap with the BAFF and APRIL binding sites.

In one embodiment the isolated antibody or antibody fragment of the present invention is characterised in that the antibody binds an epitope comprising one or more of amino acids 13, 15, 16, 17, 18, 19, 20, 22, 23, 26, 27 or 32 of CD269 (BCMA). In another embodiment the isolated antibody or antibody fragment of the present invention is characterised in that the antibody binds an epitope consisting of amino acids 13, 15, 16, 17, 18, 19, 20, 22, 23, 26, 27 and 32 of CD269 (BCMA). These residues represent the amino acids that interact directly with the antibody of the present invention, as identified by the crystal structure data provided herein. The numbering of these residues has been carried out with respect to SEQ ID No. 13, which provides the N-terminal sequence of CD269.

In one embodiment of the invention the isolated antibody or antibody fragment is characterised in that the antibody binding to CD269 (BCMA) disrupts the BAFF-CD269 and/or APRIL-CD269 interaction.

The binding of the antibodies of the present invention, for example J22.9-xi, to the extracellular domain of CD269 disrupts the BAFF-CD269 interaction. Due to the fact that the binding sites of APRIL and BAFF are positioned at similar sites to the antibody epitope, the binding of J22.9-xi to CD269 will also block the APRIL-CD269 interaction. BAFF/APRIL-CD269 interactions are thought to trigger anti-apoptotic and growth signals in the cell, respectively (Mackay, Schneider et al. (2003) Annu Rev Immunol 21:231-264; Bossen and Schneider (2006) Semin Immunol 18:263-275).

Comparison of the specific epitope of the antibody of the present invention with the binding sites of APRIL and BAFF, for which crystal structures have been solved and their interaction sites mapped, reveals a comprehensive overlap in the binding sites of the natural ligands and the antibody as described herein. This represents a beneficial and unexpected aspect of the invention and enables a reliable and effective disruption of BAFF-CD269 and/or APRIL-CD269 interactions.

The invention therefore relates to an isolated antibody or antibody fragment as described herein, wherein the antibody disrupts APRIL-CD269 interaction by binding an epitope comprising one or more amino acids of residues 13, 15, 17, 18, 19, 22, 26, 27, 30, 31, 32, 33, 34, 35 of CD269 (BCMA), in particular amino aids 13, 15, 17, 18, 19, 22, 26, 27, 32. These amino acids correspond to the binding site of APRIL on CD269, and the overlapping residues of CD269 that bind both the antibody as described herein and APRIL, respectively.

The invention therefore relates in another embodiment to an isolated antibody or antibody fragment as described herein, wherein the antibody disrupts BAFF-CD269 interaction by binding an epitope comprising one or more amino acids of residues 13, 15, 16, 17, 18, 19, 22, 25, 26, 27, 29, 30, 31, 32, 34, 35 of CD269 (BCMA), in particular amino acids 13, 15, 16, 17, 18, 19, 22, 26, 27, 32. These amino acids correspond to the binding site of BAFF on CD269, and the overlapping residues of CD269 that bind both the antibody as described herein and BAFF, respectively.

Although antibodies that bind CD269 have been described in the art that also potentially disrupt APRIL- or BAFF-interactions with CD269, no relevant disclosure is provided relating to the specific epitope of such antibodies. It cannot be assumed that the previously described antibodies also bind an epitope with such a comprehensive overlap as the antibodies of the present invention. Even if APRIL- or BAFF-interactions with CD269 have been shown to be disrupted, this could potentially occur due to binding a considerably different epitope and subsequent steric hindrance of APRIL or BAFF docking. The degree of disruption of APRIL- or BAFF-interactions with CD269 caused by the antibodies of the prior has not been documented previously.

The antibodies of the present invention enable an effective and reliable disruption, which potentially represents an improved technical effect in comparison to those antibodies described in the art. An in vitro blocking assay can be performed for determination and comparison of BAFF and/or APRIL disruption, for example with the extracellular domain of human BCMA and recombinant BAFF or APRIL.

In a preferred embodiment the epitope specificity, in combination with the high affinity shown by the antibodies described herein, represents a novel and unexpected technical effect. In essence, the exceptionally high affinity of J22.9 in combination with the overlap of the BAFF and APRIL binding sites, provides not only "disruption" or "blocking" of the binding of the natural ligands; but rather the ultra-high affinity of the antibody of the invention ensures that the native ligands are essentially excluded completely or almost completely from binding their BCMA target when the antibody is present.

As disclosed in the examples below, the affinity of the antibody as described herein is surprisingly high and comparatively better than similar approaches attempted in the prior art. A Kd in the pM range (as shown below) is commonly accepted as an outstanding affinity not to be expected in common practice.

In another aspect the antibody or antibody fragment of the invention binds CD269 with high affinity, for example when measured by surface plasmon resonance, such as Biacore, the antibody binds to human CD269 with an affinity of 20 nM or less or an affinity of 15 nM or less or an affinity of 5 nM or less or an affinity of 1000 pM or less or an affinity of 500 pM or less or an affinity of 100 pM or less, or 800 pM or less or for example about 54 pM. In a further embodiment the antibody binds to human CD269 when measured by surface plasmon resonance, such as Biacore, of between about 1 pM and about 500 pM or between about 10 pM and about 200 pM, or between about 20 pM and about 100 pM. In one embodiment of the present invention the antibody binds CD269 with an affinity of around 50 pM.

Preferred Embodiments Regarding Antibody Sequence and Structure

In one embodiment of the invention the isolated antibody or antibody fragment is characterised in that it is a chimeric, humanised, partially humanised, bi-specific or a single chain antibody, or combination thereof.

The antibodies disclosed in the examples of the present invention relate primarily to a chimeric or partially humanised antibody, comprising a human constant domains and VH and VL domains with CD269-specificity derived from mouse. The invention relates however to further humanised sequences, especially of the preferred VL and VH binding regions, which maintain the appropriate ligand affinities as described herein.

In one embodiment the antibody or fragment thereof is characterised in that the antibody is a chimeric antibody comprising VL and VH domains obtained from a mouse antibody, wherein said VL and VH domains comprise sequences capable of binding an epitope of the extracellular domain of CD269 (BCMA) as described herein, and the VL and VH domains are fused to human CL and CH domains, respectively.

In one embodiment the antibody or fragment thereof is characterised in that the VL and VH domains are fused to the human Ig kappa and IgG1 constant domains, respectively.

It was entirely surprising that the particular sequences provided herein, preferably the CDR regions of the VL and VH regions involved in binding, exhibit the specific and strong binding as demonstrated in the experimental examples. The majority of antibodies with CD269-binding properties known in the art exhibit inferior binding characteristics; being less specific and/or showing weaker interactions with the antigen epitope.

Preferred Embodiments Regarding the VH Domain

In one embodiment the antibody or antibody fragment of the present invention comprises a VH domain, wherein said VH domain comprises at least one CDR region with at least 80%, preferably 90%, sequence identity to CDR xH1 (SEQ ID No. 57; $X_8$YWMS), CDR xH2 (SEQ ID No. 58; EINPDSSTINYAPSLKX$_{11}$) and/or CDR H3 (SEQ ID No. 3; SLYYDYGDAMDYW), wherein $X_8$ is R or D and $X_{11}$ is D or G, and wherein said antibody or fragment thereof specifically binds an epitope of the extracellular domain of CD269 (BCMA) as described herein. The general sequence formulae provided herein, and in particular the sequence variants determined by the variable residues $X_8$ and $X_{11}$, relate to a unitary representation of chimeric, mouse and/or humanised sequences of the invention, in particular of the mouse chimeric antibody described herein.

In one embodiment the antibody or antibody fragment of the present invention comprises a VH domain, wherein said VH domain comprises at least one CDR region with at least 80%, preferably 90%, sequence identity to CDR H1 (SEQ ID No. 1; RYWMS), CDR H2 (SEQ ID No. 2; EINPDSSTINYAPSLKD) and/or CDR H3 (SEQ ID No. 3; SLYYDYGDAMDYW), wherein said antibody or fragment thereof specifically binds an epitope of the extracellular domain of CD269 (BCMA) as described herein.

In a preferred embodiment the antibody or antibody fragment of the invention is characterised in that at least residues W3 and S5 of a CDR H1, residue E1 of a CDR H2 and residues L2, Y3 and Y4 of a CDR H3 are not modified. These residues correspond to residues W33, S35, E50, L99, Y100 and Y101 of the VH sequences of J22.9-xi. These residues of the heavy chain CDR regions are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequences listed, preferably exhibit no modification of sequence at the sites of interaction with the epitope and maintain the desired binding specificity, are therefore encompassed in the present invention.

In one embodiment the antibody or antibody fragment of the present invention comprises a VH domain, wherein said VH domain comprises CDR regions of CDR H1 (SEQ ID No. 1; RYWMS), CDR H2 (SEQ ID No. 2; EINPDSSTINYAPSLKD) and CDR H3 (SEQ ID No. 3; SLYYDYGDAMDYW).

In one embodiment the antibody or antibody fragment of the present invention comprises a VH domain, wherein said VH domain comprises a sequence with at least 80%, preferably 90%, sequence identity to SEQ ID No. 60 ($X_1$VQLX$_2$X$_3$SGGGLVQPGGSLX$_4$LSCAASGX$_5$X$_6$FX$_7$X$_8$YVVMSWVRX$_9$APGKGLEWX$_{10}$GEINPDSSTINYAPSLKX$_{11}$X$_{12}$FX$_{13}$ISRDNAKNTLYLQMX$_{14}$X$_{15}$X$_{16}$R-X$_{17}$EDTAX$_{18}$YYCASLYYDYGDAMDYWGQGTX$_{19}$V-TVSS), wherein X1: Q, E; X2: Q, V; X3: Q, E; X4: K, R; X5: I, F; X6: D, T; X7: S, D; X8: R, D; X9: R, Q; X10: I, V; X11: D, G; X12: K, R; X13: I, T; X14: S, N; X15: K, S; X16: V, L; X17: S, A; X18: L, V; X19: S, L, and wherein said antibody or fragment thereof specifically binds an epitope of the extracellular domain of CD269 (BCMA) as described herein. The general sequence formula provided, and in particular the sequence variants determined by the variable residues X1 to X19 of the VH sequence of SEQ ID No. 60, relates to a unitary representation of chimeric, mouse and/or humanised sequences of the invention, in particular of the mouse chimeric antibody described herein.

In one embodiment the antibody or antibody fragment of the present invention comprises a VH domain, wherein said VH domain comprises a sequence with at least 80%, preferably 90%, sequence identity to SEQ ID No. 7 (QVQLQQSGGGLVQPGGSLKLSCAASGIDFSRYWMSWVRRAPGKGLEWIGEINPDSSTINYAPSLKDKFIISRDNAKNTLYLQMSKVRSEDTALYYCASLYYDYGDAMDY WGQGTSVTVSS), wherein said antibody or fragment thereof specifically binds an epitope of the extracellular domain of CD269 (BCMA) according to any one of the preceding claims.

In a preferred embodiment the antibody or antibody fragment of the invention is characterised in that at least residues W33, S35, W47, E50, L99, Y100, Y101 and A106 of the VH sequence of SEQ ID No. 60 or 7 are not modified. These residues of the heavy chain are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequence listed, preferably exhibit no modification of sequence at the sites of interaction with the epitope and maintain the desired binding specificity, are therefore encompassed in the present invention.

In a preferred embodiment the isolated antibody or antibody fragment comprises a VH domain according to SEQ ID No. 7.

Preferred Embodiments Regarding the VL Domain

In one embodiment the antibody or antibody fragment of the present invention comprises an VL domain, wherein said VL domain comprises at least one CDR region with at least 80%, preferably 90%, sequence identity to CDR L1 (SEQ ID No. 4; KASQSVDSNVA), CDR xL2 (SEQ ID No. 59; SX$_{14}$X$_{15}$LRFS) and/or CDR L3 (SEQ ID No. 6; QQYN-NYPLTFG), wherein X$_{14}$ is A or D and X$_{15}$ is S or D, and wherein said antibody or fragment thereof specifically binds an epitope of the extracellular domain of CD269 (BCMA) as described herein. The general sequence formula provided, and in particular the sequence variants determined by the variable residues X$_{14}$ and X$_{15}$, relate to a unitary representation of chimeric, mouse and/or humanised sequences of the invention, in particular of the mouse chimeric antibody described herein.

In one embodiment the antibody or antibody fragment of the present invention comprises a VL domain, wherein said VL domain comprises at least one CDR region with at least 80%, preferably 90%, sequence identity to CDR L1 (SEQ ID No. 4; KASQSVDSNVA), CDR L2 (SEQ ID No. 5; SASLRFS) and/or CDR L3 (SEQ ID No. 6; QQYNNY-PLTFG), wherein said antibody or fragment thereof specifically binds an epitope of the extracellular domain of CD269 (BCMA) as described herein.

In a preferred embodiment the antibody or antibody fragment of the invention is characterised in that at least residues S8, N9, A11 of a CDR L1, residues S1, S3, L4, F6 of a CDR L2 and residues Q1, Y3, Y6, L8 of a CDR L3 are not modified. These residues correspond to residues S31, N32, A34, S50, S52, L53, F55, Q89, Y91, Y94 and L96 of the VL sequences of J22.9-xi. These residues of the light chain CDR regions are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequences listed, preferably exhibit no modification of sequence at the sites of interaction with the epitope and maintain the desired binding specificity, are therefore encompassed in the present invention.

In one embodiment the antibody or antibody fragment of the present invention comprises a VL domain, wherein said VL domain comprises CDR regions of CDR L1 (SEQ ID No. 4; KASQSVDSNVA), CDR L2 (SEQ ID No. 5; SASLRFS) and CDR L3 (SEQ ID No. 6; QQYNNY-PLTFG).

In one embodiment the antibody or antibody fragment of the present invention comprises a VL domain, wherein said VL domain comprises a sequence with at least 80%, preferably 90%, sequence identity to SEQ ID No. 61 (DIVMTQSX$_1$X$_2$X$_3$X$_4$X$_5$X$_6$SVGDX$_7$VX$_8$X$_9$TCKASQ-SVDSNVAWYQQKPX$_{10}$QX$_{11}$PKX$_{12}$LIX$_{13}$SX$_{14}$X$_{15}$LR-FSGVPARFX$_{16}$GSGSGTDFTLTISX$_{17}$LQSEDX$_{18}$AX$_{19}$-YX$_{20}$CQQYNNYPLTFGAGTKLELKR), wherein X1: Q, P; X2: R, A; X3: F, T; X4: M, L; X5: T, S; X6: T, V; X7: R, E; X8: S, T; X9: V, L; X10: R, G; X11: S, A; X12: A, L; X13: F, Y; X14: A, D; X15: S, D; X16: T, S; X17: N, S; X18: L, F; X19: E, V; X20: F, Y, and wherein said antibody or fragment thereof specifically binds an epitope of the extracellular domain of CD269 (BCMA) as described herein. The general sequence formula provided, and in particular the sequence variants determined by the variable residues X1 to X20 of the VL sequence of SEQ ID No. 61, relates to a unitary representation of chimeric, mouse and/or humanised sequences of the invention, in particular of the mouse chimeric antibody described herein.

In one embodiment the antibody or antibody fragment of the present invention comprises a VL domain, wherein said VL domain comprises a sequence with at least 80%, preferably 90%, sequence identity to SEQ ID No. 8 (DIVMTQSQRFMTTSVGDRVSVTCKASQSVDSN-VAWYQQKPRQSPKALIFSASLRF
SGVPARFTGSGSGTDFTLTISNLQSEDLAEYFCQQYN-NYPLTFGAGTKLELKR), wherein said antibody or fragment thereof specifically binds an epitope of the extracellular domain of CD269 (BCMA) according to any one of the preceding claims.

In a preferred embodiment the antibody or antibody fragment of the invention is characterised in that at least residues S31, N32, A34, Y36, F49, S50, S52, L53, F55, G66, S67, Q89, Y91, Y94 and L96 of SEQ ID No. 61 or 8 are not modified. These residues of the light chain are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequence listed, preferably exhibit no modification of sequence at the sites of interaction with the epitope and maintain the desired binding specificity, are therefore encompassed in the present invention.

In one embodiment the antibody or antibody fragment of the present invention comprises a VL domain according to SEQ ID No. 8.

In one embodiment the antibody or antibody fragment of the present invention comprises a VH domain according to SEQ ID No. 7 and a VL domain according to SEQ ID No. 8.

Preferred Embodiments Regarding Humanised Antibody Variants

The antibodies disclosed in the examples of the present invention relate to a chimeric or partially humanised antibody, comprising human constant domains and VH and VL domains with CD269-specificity derived from mouse. The invention relates however to further humanised sequences, especially of the preferred VL and VH binding regions, which maintain the appropriate ligand affinities as described herein. The invention therefore relates to an isolated antibody or antibody fragment as described herein that is a chimeric, humanised, partially humanised, bi-specific or a single chain antibody, or combination thereof.

As disclosed in detail herein, the sequence of the preferred embodiments of the invention according to J22.9-xi was humanised in order to provide a more compatible reagent for administration in human subjects. Various humanised sequence variants of J22.9-xi have been generated and tested for their binding affinity and specificity to CD269 (BCMA). The initial results from binding assays demonstrate that the humanised sequences maintain the desired binding properties of the chimeric reagent J22.9-xi.

Preferred Embodiments Regarding the Humanised hVH Domain

In one embodiment the antibody or antibody fragment of the present invention comprises a humanised or partially humanised VH domain, wherein said VH domain comprises at least one CDR region with at least 80%, preferably 90%, sequence identity to CDR hH1 (SEQ ID No. 15; DYWMS), CDR hH2 (SEQ ID No. 16; EINPDSSTINYAPSLKG) and/or CDR hH3 (SEQ ID No. 3; SLYYDYGDAMDYW), wherein said antibody or fragment thereof specifically binds an epitope of the extracellular domain of CD269 (BCMA) as described herein.

In a preferred embodiment the antibody or antibody fragment of the invention is characterised in that at least residues W3 and S5 of CDR hH1, residue E1 of CDR hH2 and residues S1, L2 and Y3 of CDR hH3 are not modified. These residues correspond to residues W33, S35, E50, L99, Y100 and Y101 of the VH sequence of a humanised form of J22.9-xi. These residues of the heavy chain CDR regions are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequences listed, preferably exhibit no modification of sequence at the sites of interaction with the epitope and maintain the desired binding specificity, are therefore encompassed in the present invention.

In one embodiment the antibody or antibody fragment of the present invention comprises a humanised or partially humanised VH domain, wherein said VH domain comprises CDR regions of CDR hH1 (SEQ ID No. 15; DYWMS), CDR hH2 (SEQ ID No. 16; EINPDSSTINYAPSLKG) and CDR hH3 (SEQ ID No. 3; SLYYDYGDAMDYW).

In one embodiment the antibody or antibody fragment of the present invention comprises a humanised or partially humanised VH domain, wherein said VH domain comprises a sequence with at least 80%, preferably 90%, sequence identity to a sequence according to SEQ ID No. 18 to 25, wherein said antibody or fragment thereof specifically binds an epitope of the extracellular domain of CD269 (BCMA) as described herein.

In a preferred embodiment the antibody or antibody fragment of the invention is characterised in that at least residues W33, S35, W47, E50, L99, Y100 and Y101 of the sequences according to SEQ ID No. 18 to 25 are not modified. These residues of the heavy chain are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequence listed, preferably exhibit no modification of sequence at the sites of interaction with the epitope and maintain the desired binding specificity, are therefore encompassed in the present invention.

In one embodiment the antibody or antibody fragment of the present invention comprises a humanised or partially humanised VH domain according to a sequence of one of SEQ ID No. 18 to 25.

Preferred Embodiments Regarding the Humanised hVL Domain

In one embodiment the antibody or antibody fragment of the present invention comprises a humanised or partially humanised VL domain, wherein said VL domain comprises at least one CDR region (preferably all 3) with at least 80%, preferably 90%, sequence identity to CDR hL1 (SEQ ID No. 4; KASQSVDSNVA), CDR hL2 (SEQ ID No. 17; SDDLRFS) and/or CDR hL3 (SEQ ID No. 6; QQYNNYPLTFG), wherein said antibody or fragment thereof specifically binds an epitope of the extracellular domain of CD269 (BCMA) as described herein.

In a preferred embodiment the antibody or antibody fragment of the invention is characterised in that at least residues S8, N9, A11 of CDR hL1, residues S1, L4, F6 of CDR hL2 and residues Q1, Y3, Y6, L8 of CDR hL3 are not modified. These residues correspond to residues S31, N32, A34, S50, L53, F55, Q89, Y91, Y94 and L96 of a humanised form of the VL sequence of J22.9-xi. These residues of the light chain CDR regions are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequences listed, preferably exhibit no modification of sequence at the sites of interaction with the epitope and maintain the desired binding specificity, are therefore encompassed in the present invention.

In one embodiment the antibody or antibody fragment of the present invention comprises a humanised or partially humanised VL domain, wherein said VL domain comprises CDR regions of CDR hL1 (SEQ ID No. 4; KASQSVDSNVA), CDR hL2 (SEQ ID No. 17; SDDLRFS) and CDR hL3 (SEQ ID No. 6; QQYNNYPLTFG).

In one embodiment the antibody or antibody fragment of the present invention comprises a humanised or partially humanised VL domain, wherein said VL domain comprises a sequence with at least 80%, preferably 90%, sequence identity to a sequence according to SEQ ID No. 26 to 56, wherein said antibody or fragment thereof specifically binds an epitope of the extracellular domain of CD269 (BCMA) as described herein.

In a preferred embodiment the antibody or antibody fragment of the invention is characterised in that at least residues S31, N32, A34, Y36, F49, S50, L53, F55, G66, S67, Q89, Y91, Y94 and L96 of the sequences according to SEQ ID No. 26 to 56 are not modified. These residues of the light chain are directly involved in interactions with the epitope and therefore should be maintained in the antibody sequence. The modification of amino acids outside these particular residues may be carried out according to routine measures known to those skilled in the art. Sequence variants, which show at least 80% sequence identity to the specific sequence listed, preferably exhibit no modification of sequence at the sites of interaction with the epitope and maintain the desired binding specificity, are therefore encompassed in the present invention.

In one embodiment the antibody or antibody fragment of the present invention comprises a humanised or partially humanised VL domain according to a sequence of one of SEQ ID No. 26 to 56.

Further Preferred Embodiments of the Invention

In further embodiments the antibody or antibody fragment as described herein is characterised in that modifications to the amino acid sequences according to SEQ ID No. 1 to 8 and 15 to 61 are present, which are conservative substitutions.

In further embodiments the antibody or antibody fragment as described herein is characterised in that modifications to the amino acid sequences according to SEQ ID No. 1 to 8 and 15 to 61 are present, which are alanine substitutions.

The invention therefore relates to sequence variants of the CDR regions as provided herein, for example for CDR H1 (xxWxS; SEQ ID NO: 65), CDR H2 (Exxxxxxxxxxxxxxx; SEQ ID NO: 66), CDR H3 (LYYxxxxxxxxx; SEQ ID NO: 67), CDR L1 (xxxxxxxSNxAx; SEQ ID NO: 68), CDR L2 (SxSLxFx; SEQ ID NO: 69) and/or CDR L3 (QxYxxYxLxxx; SEQ ID NO: 70), wherein X is any given amino acid, preferably a conserved substitution or an alanine substitution.

In one embodiment the invention relates to an antibody or antibody fragment comprising an amino acid sequence defined by one or more of the amino acids that directly interact with the CD269 target and/or one or more amino acids that interact via water interactions (see Tables 1 to 6). The large number of water interactions involved in the binding of the antibody as described herein to the epitope represents an unusual and surprising aspect of the binding. In particular the high affinity of the antibody directed to the particular epitope described herein, in combination with the large number of water interactions involved in the binding surface between the antibody and epitope, represents a surprising and unexpected aspect of the invention.

The invention therefore relates to an antibody or antibody fragment comprising an amino acid sequence as described herein, for example sequences according to SEQ ID No. 1 to 8 or 15 to 61, wherein the sequence is characterised by the presence of the specific amino acid residues that are involved in the interaction surface with the target epitope via a water bridge according to table 6, selected from the group comprising Ser31, Ser31, Asn32, Tyr36, Ser50, Ser52, Gly66, Gln89, Tyr91 and/or Tyr94 of the light chain, and/or Trp33, Ser35, Trp47, Glu50, Leu99 and/or Tyr101 of the heavy chain.

The antibody of the invention could be further characterised by the amino acids residues of the epitope involved in the interaction via water bridges with the antibody as described herein. The relevant features are provided in Table 6. The invention is therefore, for example in one embodiment, characterised in that residue Ser31 of the light chain interacts with Thr32 of CD269 via a water molecule. Such a description of the binding properties of the antibody of the present invention is intended for each interaction as provided in Table 6.

Furthermore, sequence variants of the antibodies described herein are encompassed in the present invention, in which one or more residues involved in a "water bridging" interaction is modified in order to "substitute" a direct side-chain interaction into the sequence at the expense of a water "bridge". For example, a mutation or change could be made in the amino acid sequence displacing the water from the interaction interface but not substantially affecting the affinity of the interaction.

The invention therefore relates to an antibody or antibody fragment comprising an amino acid sequence as described herein, for example sequences according to SEQ ID No. 1 to 8 or 15 to 61, wherein the sequence is characterised by sequence variation of those amino acid residues that are involved in the interaction surface with the target epitope via a water bridge according to table 6, selected from the group comprising Ser31, Ser31, Asn32, Tyr36, Ser50, Ser52, Gly66, Gln89, Tyr91 and/or Tyr94 of the light chain, and/or Trp33, Ser35, Trp47, Glu50, Leu99 and/or Tyr101 of the heavy chain. Variation at these positions could relate to any given amino acid substitution, preferably an amino acid substitution that would effectively displace the water from the interaction but maintain similar binding properties with respect to epitope affinity and specificity.

In another embodiment of the invention, the CDR sequences of the antibody of the present invention may be modified, so that other amino acids than those specified in tables 1 and 2 are modified. Maintenance of the amino acids responsible for direct binding may lead to the binding specificity as described herein. Antibody variants, in which amino acids are modified, which do not directly interact with the target epitope, are also included in the scope of the invention.

One embodiment of the invention therefore relates to modified sequences of SEQ ID No. 1 to 3, whereby the respective sequence exhibits no sequence change at positions Trp33, Glu50, Leu99, Tyr100, Tyr101 and/or Ala106.

One embodiment of the invention therefore relates to modified sequences of SEQ ID No. 4 to 6, whereby the respective sequence exhibits no sequence change at positions Ser31, Asn32, Ala34, Tyr36, Phe49, Ser50, Ser52, Leu53, Ser67, Phe55, Gln89, Tyr91, Tyr94 and/or Leu96.

The modified sequences of the CDRs as described may in some embodiments exhibit an 80% or more sequence identity to SEQ ID No. 1 to 6, although when the binding residues are maintained, an 80% sequence identity, across the sequence of the CDR or the entire sequence of the heavy and/or light chains themselves, is not necessarily required for maintenance of function.

In one embodiment of the invention the isolated antibody or antibody fragment is characterised in that the antibody is glycosylated, preferably comprising an N-linked oligosaccharide chain, preferably at Asn297 of the heavy chain.

Glycosylation of the antibody refers to the attachment of carbohydrates or glycans to the antibody. N-linked glycans are attached to the nitrogen of asparagine or arginine sidechains. The carbohydrate chains attached to the target proteins serve various functions. For instance, some proteins do not fold correctly unless they are glycosylated first. Also, polysaccharides linked at the amide nitrogen of asparagine in the protein can confer stability on some secreted glycoproteins. Glycosylation in this case is not a strict requirement for proper folding, but unglycosylated protein can be degraded more quickly.

As is demonstrated in the examples of the present invention, the deglycosylation of the antibody disclosed therein leads to a reduction in therapeutic effect in comparison to glycosylated forms of the antibody. It was surprising, that the glycosylation would play a significant role in maintaining activity of the antibody. The glycosylation therefore represents a preferred embodiment of the invention associated with unexpected technical advantages.

As demonstrated in the examples herein, although the overall tumor load of animals treated with J22.9-xi-N-glycan (deglycosylated) was not significantly different from animals receiving the isotype control antibody, the lifespan of these mice was substantially increased compared to the isoAb-treated group. Since J22.9-xi-N-glycan was shown to be unable to induce ADCC or CDC, this result indicates that alone the binding of J22.9-xi to BCMA hinders tumor growth. It may be reasonably considered that this is due to blocking of the interaction between the receptor and its native ligands (APRIL and BAFF). This aspect of the invention and the antibodies described herein represents a surprising technical effect, which could not have been derived from the antibodies of the prior art. The J22.9-xi-N-glycan (deglycosylated) can be considered a control sample in the experiments described which enables the binding of the antibody to its target epitope, without the downstream effects of ADCC or CDC, to be assessed for potentially therapeutic effect. The antibodies of the invention, preferably with glycosylation, therefore demonstrate such an effective epitope binding that enables the prevention (or significant disruption) of binding by the natural ligands to lead to cell toxicity. This characteristic of the antibodies described herein has not been described for similar antibodies described in the art.

Use and Functional Aspects of the Invention

The antibodies of the present invention have been shown to bind the epitopes described herein, block interaction of the natural ligands of this epitope, in addition to inducing CDC and ADCC.

Antibody-Dependent Cell-Mediated Cytotoxicity (ADCC) is one factor induced by the antibody of the present invention that generates the desired therapeutic effect. ADCC is a mechanism of cell-mediated immune defence, whereby an effector cell of the immune system actively lyses a target cell, whose membrane-surface antigens have been bound by specific antibodies. After binding of CD269-expressing cells by the antibodies of the present invention ADCC may be induced. Classical ADCC is mediated by natural killer (NK) cells; macrophages, neutrophils and eosinophils can also mediate ADCC. ADCC is part of the adaptive immune response due to its dependence on a prior antibody response. Experiments in mice may indicate that ADCC is an important mechanism of action of therapeutic antibodies as described herein.

A preferred embodiment of the invention relates to the isolated antibody or antibody fragment as described herein for use as a medicament in the treatment of a medical disorder associated with the presence of pathogenic B cells.

In one embodiment of the invention the medical disorder is a CD269-associated disorder, preferably associated with pathogenic B cells, which is preferably a disease of plasma cells and/or memory B cells.

A disease of plasma cells may be a cancer of plasma cells, for example multiple myeloma, plasmacytoma, Waldenström macroglobulinemia or plasma cell leukemia. A disease of plasma cells may be a cancer of B lymphocytes, such as Hodgkin's disease.

In one embodiment of the invention the medical disorder is an autoimmune disease associated with autoreactive plasma cells and/or autoreactive memory B cells, such as an inflammatory autoimmune disease, for example systemic lupus erythematosus or rheumatic arthritis.

The invention therefore also encompasses a method of treatment for the medical disorders as disclosed herein, preferably comprising the administration of a therapeutically effective amount of antibody to a subject in need of such treatment.

A further aspect of the invention relates to an antibody-drug conjugate (ADC) comprising the antibody or antibody fragment as described herein. Anti-CD269 Antibody-Drug Conjugates "anti-CD269 ADC" can be described as an anti-CD269 antibody or fragment thereof conjugated to a therapeutic agent. In certain embodiments, the ADC comprises an anti-CD269 antibody (e.g., J22.9-xi or derivative or fragment thereof, including, for example, a chimeric or humanized form thereof).

The ADCs or ADC derivatives as described herein produce clinically beneficial effects on CD269-expressing cells when administered to a subject with a CD269-expressing medical condition, such as cancer or autoimmune disorder. In one embodiment, the anti-CD269 antibody or derivative thereof is conjugated to a cytotoxic agent, such that the resulting ADC or ADC derivative exerts a cytotoxic effect on a CD269-expressing cancer cell, preferably when taken up or internalized by the cell.

The anti-CD269 ADC or ADC derivative is preferably internalized and accumulates within a CD269-expressing cell, where the ADC or ADC derivative exerts a therapeutic effect (e.g., a cytotoxic effect). Particularly suitable moieties for conjugation to antibodies or antibody derivatives are chemotherapeutic agents, prodrug converting enzymes, radioactive isotopes or compounds, or toxins. For example, an anti-CD269 antibody or derivative thereof can be conjugated to a cytotoxic agent such as a chemotherapeutic agent, or a toxin (e.g., a cytostatic or cytocidal agent).

Another aspect of the invention relates to a preferably isolated nucleic acid molecule selected from the group consisting of:
  a) a nucleic acid molecule comprising a nucleotide sequence
     which encodes an isolated antibody or antibody fragment according to any one of the preceding claims,
     which encodes an amino acid sequence selected from the group consisting of those sequences according to SEQ ID 1 to 8 or 15 to 61,
     comprising a sequence or sequence fragment of VH2 (SEQ ID No. 9),
     comprising a sequence or sequence fragment of VL2 (SEQ ID No. 10);
  b) a nucleic acid molecule which is complementary to a nucleotide sequence in accordance with a);
  c) a nucleic acid molecule comprising a nucleotide sequence having sufficient sequence identity to be functionally analogous/equivalent to a nucleotide sequence according to a) or b), comprising preferably a sequence identity to a nucleotide sequence according to a) or b) of at least 80%, preferably 90%, more preferably 95%;
  d) a nucleic acid molecule which, as a consequence of the genetic code, is degenerated into a nucleotide sequence according to a) through c); and
  e) a nucleic acid molecule according to a nucleotide sequence of a) through d) which is modified by deletions, additions, substitutions, translocations, inversions and/or insertions and functionally analogous/equivalent to a nucleotide sequence according to a) through d).

A further aspect of the invention relates to a host cell, such as a bacterial cell or mammalian cell, preferably a hybridoma cell or cell line, capable of producing an antibody or antibody fragment as described herein, and/or comprising a nucleic acid molecule as described herein.

A further aspect of the invention relates to a pharmaceutical composition comprising the isolated antibody or antibody fragment as described herein, a nucleic acid molecule as described herein or a host cell as described herein, together with a pharmaceutically acceptable carrier.

An additional and surprising aspect of the invention is an improved stability of the antibody as disclosed herein. The antibody can readily be stored for extended periods under appropriate conditions without any loss of binding affinity. Appropriate tests have been carried out regarding maintenance of activity after storage at either −80 or 4 deg C., which demonstrate unexpectedly good stability of the antibody and maintenance of activity after storage at both aforementioned temperatures (FIG. 3, c).

The production of the antibody of the invention was inherently difficult and not achievable by straightforward routine methods. As is shown in FIG. 7, hybridoma J22.9 lost the capacity to produce/secrete the anti-BCMA antibody over time (FIG. 7). Due to this, the variable regions of the heavy and light chains were amplified using PCR and subsequently cloned at the 5' end of the human constant IgG1 and K light chain genes, respectively. Through co-transfection of 293-6E cells with these two plasmids, the chimeric J22.9-xi antibody was eventually produced. Routine methods were therefore not able to be applied without modification. Production of the antibody as described herein therefore represents a technical feat of significant effort and difficulty, in itself showing inventive effort.

A further advantage of the antibodies as described herein the effective systemic depletion of myeloma cells as demonstrated in the examples. Antibodies previously disclosed in the prior art have not been demonstrated to exhibit the desired anti-plasma cell effect in a systemic manner Studies carried out on the antibodies of the prior art disclose only sub-cutaneous injection with myeloma cells and subsequent treatment of the isolated cell mass. The present invention provides an antibody capable of systemic depletion of cancerous multiple myeloma cells after their i.v. injection, as demonstrated in the examples. The effective depletion of targeted cells represents a technical effect that has not previously been demonstrated in the prior art in addition to a beneficial property of the antibodies of the present invention.

BRIEF DESCRIPTION OF THE DRAWINGS

The invention is demonstrated by way of the examples and figures disclosed herein. The figures provided herein represent particular embodiments of the invention and are not intended to limit the scope of the invention. The figures are to be considered as providing a further description of possible and potentially preferred embodiments that enhance the technical support of one or more non-limiting embodiments.

FIG. 8: Summary of the sequences of the chimeric antibody according to J22.9-xi.

FIG. 9: Summary of the sequences of the humanised sequences of J22.9-xi. (Black: Amino acids changed for human sequence, Underlined: CDR regions).

Figure 1:
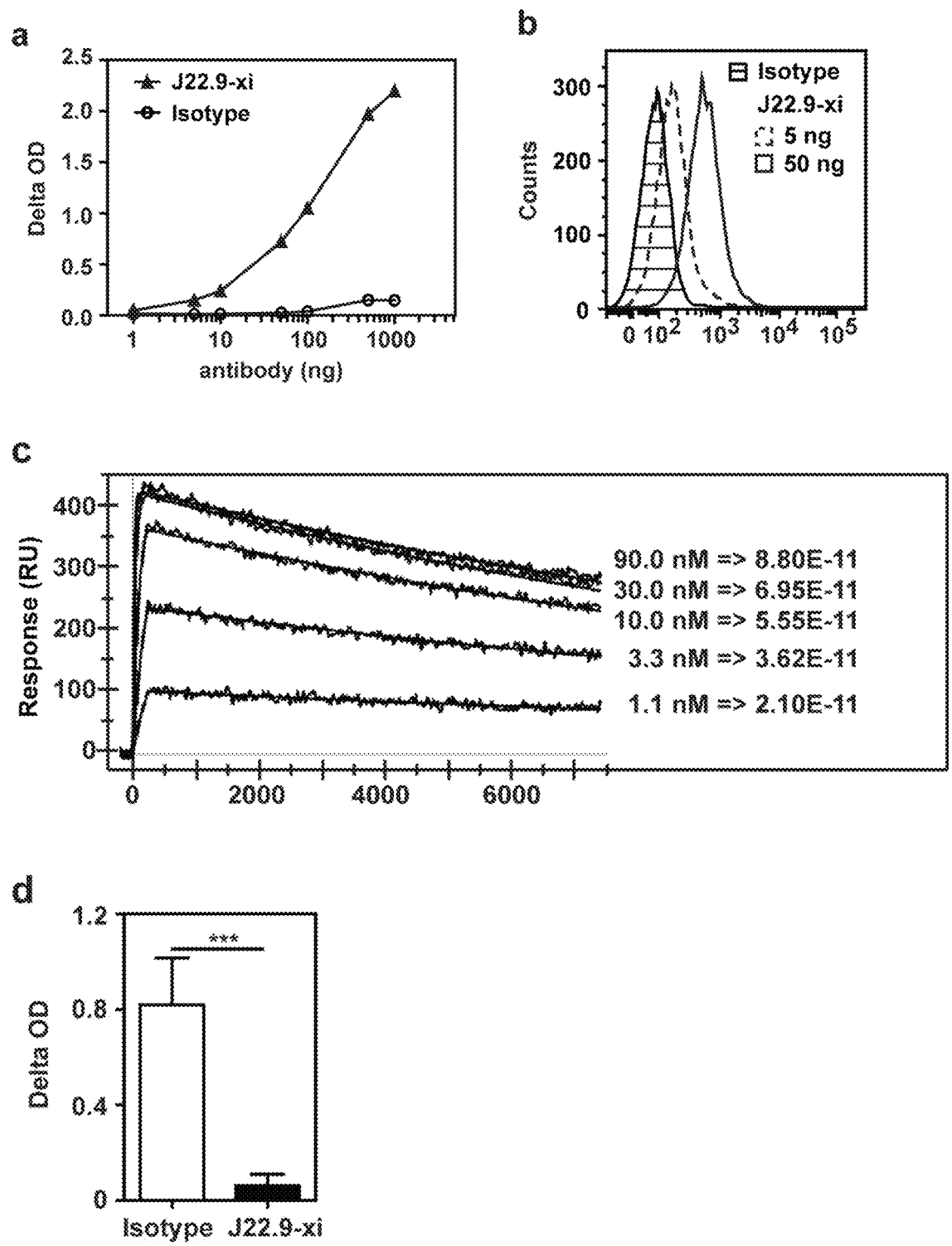
FIG. 1: In vitro characterization of J22.9-xi. Concentration dependent binding of J22.9-xi to BCMA in (a) ELISA and (b) by flow cytometry using CD269-positive MM.1S cells. (c) Binding affinity of J22.9-xi to BCMA was determined from surface plasmon resonance measurements with the indicated concentrations of BCMA. (d) J22.9-xi blocks the interaction between BAFF and BCMA adsorbed onto microtiter plates.

Heavy chain sequences: HX (SEQ ID NO: 71), HM (SEQ ID NO: 72), H0 (SEQ ID NO: 73), H1 (SEQ ID NO: 74), H2 (SEQ ID NO: 75), H3 (SEQ ID NO: 76), H4 (SEQ ID NO: 77), H5 (SEQ ID NO: 78), H6 (SEQ ID NO: 79) and H7 (SEQ ID NO: 80).

Light chain sequences: LX (SEQ ID NO: 81), LM (SEQ ID NO: 82), L0 (SEQ ID NO: 83), L1 (SEQ ID NO: 84), L2

(SEQ ID NO: 85), L3 (SEQ ID NO: 86), L4 (SEQ ID NO: 87), L5 (SEQ ID NO: 88), L6 (SEQ ID NO: 89), L7 (SEQ ID NO: 90), L8 (SEQ ID NO: 91), L9 (SEQ ID NO: 92), L10 (SEQ ID NO: 93), L11 (SEQ ID NO: 94), L12 (SEQ ID NO: 95), L13 (SEQ ID NO: 96), L14 (SEQ ID NO: 97), L15 (SEQ ID NO: 98), L16 (SEQ ID NO: 99), L17 (SEQ ID NO: 100), L18 (SEQ ID NO: 101), L19 (SEQ ID NO: 102), L20 (SEQ ID NO: 103, L21 (SEQ ID NO: 104), L22 (SEQ ID NO: 105), L23 (SEQ ID NO: 106), L24 (SEQ ID NO: 107), L25 (SEQ ID NO: 108), L26 (SEQ ID NO: 109), L27 (SEQ ID NO: 110), L28 (SEQ ID NO: 111), L29 (SEQ ID NO: 112) and L30 (SEQ ID NO: 113).

DETAILED DESCRIPTION OF THE INVENTION

As used herein, an "antibody" generally refers to a protein consisting of one or more polypeptides substantially encoded by immunoglobulin genes or fragments of immunoglobulin genes. Where the term "antibody" is used, the term "antibody fragment" may also be considered to be referred to. The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. The basic immunoglobulin (antibody) structural unit is known to comprise a tetramer or dimer. Each tetramer is composed of two identical pairs of polypeptide chains, each pair having one "light" (L) (about 25 kD) and one "heavy" (H) chain (about 50-70 kD). The N-terminus of each chain defines a variable region of about 100 to 110 or more amino acids, primarily responsible for antigen recognition. The terms "variable light chain" and "variable heavy chain" refer to these variable regions of the light and heavy chains respectively. Optionally, the antibody or the immunological portion of the antibody, can be chemically conjugated to, or expressed as, a fusion protein with other proteins.

The antibodies of the invention are intended to bind against mammalian, in particular human, protein targets. The use of protein names may correspond to either mouse or human versions of a protein.

"Specific binding" is to be understood as via one skilled in the art, whereby the skilled person is clearly aware of various experimental procedures that can be used to test binding and binding specificity. Some cross-reaction or background binding may be inevitable in many protein-protein interactions; this is not to detract from the "specificity" of the binding between antibody and epitope. The term "directed against" is also applicable when considering the term "specificity" in understanding the interaction between antibody and epitope.

Antibodies of the invention include, but are not limited to polyclonal, monoclonal, bispecific, human, humanized or chimeric antibodies, single variable fragments (ssFv), single domain antibodies (such as VHH fragments from nanobodies), single chain fragments (scFv), Fab fragments, F(ab')$_2$ fragments, fragments produced by a Fab expression library, anti-idiotypic antibodies and epitope-binding fragments or combinations thereof of any of the above, provided that they retain the original binding properties. Also mini-antibodies and multivalent antibodies such as diabodies, triabodies, tetravalent antibodies and peptabodies can be used in a method of the invention. The immunoglobulin molecules of the invention can be of any class (i.e. IgG, IgE, IgM, IgD and IgA) or subclass of immunoglobulin molecules. Thus, the term antibody, as used herein, also includes antibodies and antibody fragments either produced by the modification of whole antibodies or synthesized de novo using recombinant DNA methodologies.

Humanized antibody comprising one or more CDRs of antibodies of the invention or one or more CDRs derived from said antibodies can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

The term humanized antibody means that at least a portion of the framework regions of an immunoglobulin is derived from or adjusted to human immunoglobulin sequences. The humanised, chimeric or partially humanised versions of the mouse monoclonal antibodies can, for example, be made by means of recombinant DNA technology, departing from the mouse and/or human genomic DNA sequences coding for H and L chains or from cDNA clones coding for H and L chains. Humanized forms of mouse antibodies can be generated by linking the CDR regions of non-human antibodies to human constant regions by recombinant DNA techniques (Queen et al., 1989; WO 90/07861). Alternatively the monoclonal antibodies used in the method of the invention may be human monoclonal antibodies. Human antibodies can be obtained, for example, using phage-display methods (WO 91/17271; WO 92/01047).

As used herein, humanized antibodies refer also to forms of non-human (e.g. murine, camel, llama, shark) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity.

As used herein, human or humanised antibody means an antibody having an amino acid sequence corresponding to that of an antibody produced by a human and/or has been made using any of the techniques for making human antibodies known in the art or disclosed herein. Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using amyloid fibrillar and/or non-fibrillar polypeptides or fragments thereof as an affinity reagent. Monoclonal antibodies can be obtained from serum according to the technique described in WO 99/60846.

The affinity reagent, antibody or fragment thereof according to the invention may be PEGylated, whereby PEGylation refers to covalent attachment of polyethylene glycol (PEG) polymer chains to the inventive antibody. PEGylation may be routinely achieved by incubation of a reactive derivative of PEG with the target molecule. PEGylation to the antibody can potentially mask the agent from the host's immune system, leading to reduced immunogenicity and antigenicity or increase the hydrodynamic size of the agent which may prolong its circulatory time by reducing renal clearance.

A variable region of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948). As used herein, a CDR may refer to CDRs defined by either approach or by a combination of both approaches.

In some embodiments, the invention provides an antibody, which comprises at least one CDR, at least two, at least three, or more CDRs that are substantially identical to at least one CDR, at least two, at least three, or more CDRs of the antibody of the invention. Other embodiments include antibodies which have at least two, three, four, five, or six CDR(s) that are substantially identical to at least two, three, four, five or six CDRs of the antibodies of the invention or derived from the antibodies of the invention. In some embodiments, the at least one, two, three, four, five, or six CDR(s) are at least about 85%, 86%, 87%, 88%, 89%, 90%, 95%, 96%, 97%, 98%, or 99% identical to at least one, two or three CDRs of the antibody of the invention. It is understood that, for purposes of this invention, binding specificity and/or overall activity is generally retained, although the extent of activity may vary compared to said antibody (may be greater or lesser).

The half life and cytotoxic potential of an antibody are dependent primarily on the interaction of the Fc-domain with different Fc-gamma-receptors. In the case of the antibody half life, the neonatal Fc receptor (FcRn) plays a major role. This receptor is expressed on several cell types and tissues such as monocytes and vascular endothelia cells that are able to take up serum proteins into their recycling endosomes. In the endosomes, the pH is decreased to approximately 6 and under these conditions the antibodies are able to bind to FcRn. This interaction protects the antibodies from degradation until they are again released into the blood where the physiological pH disrupts the binding to the receptor (Roopenian and Akilesh (2007) Nat Rev Immunol 7:715-725). The higher the affinity of the antibody to the FcRn at pH 6, the greater the half life of that antibody. Fc-fragment mutations known to stabilize this interaction are summarised in Presta (2008, Curr Opin Immunol 20:460-470).

The antibody-dependent cellular cytotoxicity (ADCC) can also be improved by strengthening the binding of the Fc-domain to activating Fc-gamma receptors (FcγR). This can also be achieved through mutations in the Fc-gamma domain as summarized in Presta (2008, Curr Opin Immunol 20:460-470).

Another way to change the ADCC is manipulation of the sugar moiety present on each IgG at Asn297. Defucolylation and removal of sialic acid from the end of the sugar molecules are known to increase the cytotoxic potential of an antibody (Anthony and Ravetch (2010) J Clin Immunol 30 Suppl 1:S9-14).

Sequence variants of the claimed nucleic acids, proteins and antibodies, for example defined by the claimed % sequence identity, that maintain the said properties of the invention are also included in the scope of the invention. Such variants, which show alternative sequences, but maintain essentially the same binding properties, such as target specificity, as the specific sequences provided are known as functional analogues, or as functionally analogous. Sequence identity relates to the percentage of identical nucleotides or amino acids when carrying out a sequence alignment.

It will be appreciated by those of ordinary skill in the art that, as a result of the degeneracy of the genetic code, there are many nucleotide sequences that encode a polypeptide as described herein. Some of these polynucleotides bear minimal homology or sequence identity to the nucleotide sequence of any native gene. Nonetheless, polynucleotides that vary due to differences in codon usage are specifically contemplated by the present invention. Deletions, substitutions and other changes in sequence that fall under the described sequence identity are also encompassed in the invention.

Protein modifications, which may occur through substitutions, are also included within the scope of the invention. Substitutions as defined herein are modifications made to the amino acid sequence of the protein, whereby one or more amino acids are replaced with the same number of (different) amino acids, producing a protein which contains a different amino acid sequence than the primary protein, preferably without significantly altering the function of the protein. Like additions, substitutions may be natural or artificial. It is well known in the art that amino acid substitutions may be made without significantly altering the protein's function. This is particularly true when the modification relates to a "conservative" amino acid substitution, which is the substitution of one amino acid for another of similar properties. Such "conserved" amino acids can be natural or synthetic amino acids which because of size, charge, polarity and conformation can be substituted without significantly affecting the structure and function of the protein. Frequently, many amino acids may be substituted by conservative amino acids without deleteriously affecting the protein's function.

In general, the non-polar amino acids Gly, Ala, Val, Ile and Leu; the non-polar aromatic amino acids Phe, Trp and Tyr; the neutral polar amino acids Ser, Thr, Cys, Gln, Asn and Met; the positively charged amino acids Lys, Arg and His; the negatively charged amino acids Asp and Glu, represent groups of conservative amino acids. This list is not exhaustive. For example, it is well known that Ala, Gly, Ser and sometimes Cys can substitute for each other even though they belong to different groups.

Substitution variants have at least one amino acid residue in the antibody molecule removed and a different residue inserted in its place. The sites of greatest interest for substitutional mutagenesis include the hypervariable regions, but FR alterations are also contemplated. If such substitutions result in a change in biological activity, then more substantial changes, denominated "exemplary substitutions"

in Table 1, or as further described below in reference to amino acid classes, may be introduced and the products screened.

Potential Amino Acid Substitutions:

| Original residue | Preferred conservative substitutions | Examples of exemplary substitutions |
|---|---|---|
| Ala (A) | Val | Val; Leu; Ile |
| Asg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn, Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain.

Conservative amino acid substitutions are not limited to naturally occurring amino acids, but also include synthetic amino acids. Commonly used synthetic amino acids are omega amino acids of various chain lengths and cyclohexyl alanine which are neutral non-polar analogs; citrulline and methionine sulfoxide which are neutral non-polar analogs, phenylglycine which is an aromatic neutral analog; cysteic acid which is a negatively charged analog and ornithine which is a positively charged amino acid analog. Like the naturally occurring amino acids, this list is not exhaustive, but merely exemplary of the substitutions that are well known in the art.

The antibodies of the present invention may be produced by transfection of a host cell with an expression vector comprising the coding sequence for the antibody of the invention. An expression vector or recombinant plasmid is produced by placing these coding sequences for the antibody in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antibody light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antibody may reside on a single vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antibody of the invention. The antibody which includes the association of both the recombinant heavy chain and/or light chain is screened from culture by appropriate assay, such as ELISA or RIA. Similar conventional techniques may be employed to construct other antibodies.

Suitable vectors for the cloning and subcloning steps employed in the methods and construction of the compositions of this invention may be selected by one of skill in the art. For example, the conventional pUC series of cloning vectors may be used. One vector, pUC19, is commercially available. The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antibodies of the present invention. Host cells useful for the cloning and other manipulations of these cloning vectors are also conventional.

Suitable host cells or cell lines for the expression of the antibodies of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other prokaryotic or eukaryotic cell lines may be employed. The selection of suitable mammalian host cells and methods for transformation, culture, amplification, screening and product production and purification are known in the art.

In accordance with the present invention there is provided a method of producing an anti-CD269-antibody of the present invention which binds to and neutralises the activity of human CD269 which method comprises the steps of; providing a first vector encoding a heavy chain of the antibody; providing a second vector encoding a light chain of the antibody; transforming a mammalian host cell (e.g. CHO) with said first and second vectors; culturing the host cell of step (c) under conditions conducive to the secretion of the antibody from said host cell into said culture media; recovering the secreted antibody of step (d). Once expressed, the antibody can be assessed for the desired binding properties using methods as described herein.

The invention encompasses immunoconjugates (interchangeably referred to as "antibody-drug conjugates" or "ADCs") comprising an antibody according to the invention as herein described including, but not limited to, an antibody conjugated to one or more cytotoxic agents, such as a chemotherapeutic agent, a drug, a growth inhibitory agent, a toxin (e.g., a protein toxin, an enzymatically active toxin of bacterial, fungal, plant, or animal origin, or fragments thereof), or a radioactive isotope (i.e., a radioconjugate). Techniques for conjugating therapeutic agents to proteins, and in particular to antibodies, such as for the Anti-CD269 Antibody-Drug Conjugates of the present invention, are well-known. (See, e.g., Arnon et al., "Monoclonal Antibodies For Immunotargeting Of Drugs In Cancer Therapy," in Monoclonal Antibodies And Cancer Therapy (Reisfeld et al. eds., Alan R. Liss, Inc., 1985); Hellstrom et al., "Antibodies For Drug Delivery," in Controlled Drug Delivery (Robinson et al. eds., Marcel Dekker, Inc., 2nd ed. 1987); Thorpe, "Antibody Carriers Of Cytotoxic Agents In Cancer Therapy: A Review," in Monoclonal Antibodies '84: Biological And Clinical Applications (Pinchera et al. eds., 1985); "Analysis, Results, and Future Prospective of the Therapeutic Use of Radiolabeled Antibody In Cancer Therapy," in Monoclonal Antibodies For Cancer Detection And Therapy (Baldwin et al. eds., Academic Press, 1995); and Thorpe et al., 1982, Immunol. Rev. 62:119-58. See also, e.g., PCT publication WO 89/12624.)

Typically, the ADC or ADC derivative comprises a linker region between the therapeutic agent and the anti-CD269 antibody or derivative thereof. As noted supra, in typical embodiments, the linker is cleavable under intracellular conditions, such that cleavage of the linker releases the therapeutic agent from the antibody in the intracellular environment. For example, in some embodiments, the linker is cleavable by a cleaving agent that is present in the intracellular environment (e.g., within a lysosome or endosome or caveolae). The linker can be, e.g., a peptidyl linker that is cleaved by an intracellular peptidase or protease enzyme, including, but not limited to, a lysosomal or endosomal protease. In other embodiments, the cleavable linker is pH-sensitive, i.e., sensitive to hydrolysis at certain pH values. Typically, the pH-sensitive linker is hydrolyzable under acidic conditions. In yet other embodiments, the linker is cleavable under reducing conditions (e.g., a disulfide linker). A variety of disulfide linkers are known in the art (See for example Wawrzynczak et al., In Immunoconjugates: Antibody Conjugates in Radioimagery and Therapy of Cancer (C. W. Vogel ed., Oxford U. Press, 1987. See also U.S. Pat. No. 4,880,935.)

Typically, the linker is not substantially sensitive to the extracellular environment. In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the ADC or ADC derivate as described herein). In yet other embodiments, the linker promotes cellular internalization when conjugated to both the therapeutic agent and the anti-CD269 antibody or derivative thereof (i.e., in the milieu of the ADC or ADC derivative as described herein). A variety of linkers that can be used with the present compositions and methods are described in WO 2004010957 entitled "Drug Conjugates and Their Use for Treating Cancer, An Autoimmune Disease or an Infectious Disease" filed Jul. 31, 2003, and U.S. Provisional Application No. 60/400,403, entitled "Drug Conjugates and their use for treating cancer, an autoimmune disease or an infectious disease", filed Jul. 31, 2002 (the disclosure of which is incorporated by reference herein).

In certain embodiments, an immunoconjugate comprises an antibody as described herein, including but not limited to, an antibody and a chemotherapeutic agent or other toxin. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies.

Antibodies or fragments thereof of the present invention may also be conjugated to one or more toxins, including, but not limited to, a calicheamicin, maytansinoids, dolastatins, aurostatins, a trichothecene, and CC1065, and the derivatives of these toxins that have toxin activity. Suitable cytotoxic agents include, but are not limited to, an auristatin including dovaline-valine-dolaisoleunine-dolaproine-phenylalanine (MMAF) and monomethyl auristatin E (MMAE) as well as ester forms of MMAE, a DNA minor groove binding agent, a DNA minor groove alkylating agent, an enediyne, a lexitropsin, a duocarmycin, a taxane, including paclitaxel and docetaxel, a puromycin, a dolastatin, a maytansinoid, and a vinca alkaloid. Specific cytotoxic agents include topotecan, morpholino-doxorubicin, rhizoxin, cyanomorpholino-doxorubicin, dolastatin-10, echinomycin, combretatstatin, chalicheamicin, maytansine, DM-1, DM-4, netropsin. Other suitable cytotoxic agents include antitubulin agents, such as an auristatin, a vinca alkaloid, a podophyllotoxin, a taxane, a baccatin derivative, a cryptophysin, a maytansinoid, a combretastatin, or a dolastatin. Antitubulin agent include dimethylvaline-valine-dolaisoleuine-dolaproine-phenylalanine-p-phenylenediamine (AFP), MMAF, MMAE, auristatin E, vincristine, vinblastine, vindesine, vinorelbine, VP-16, camptothecin, paclitaxel, docetaxel, epothilone A, epothilone B, nocodazole, colchicines, colcimid, estramustine, cemadotin, discodermolide, maytansine, DM-1, DM-4 or eleutherobin.

In some embodiments, the immunoconjugate comprises an antibody conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al. (2001) Antimicrob. Agents and Chemother. 45(12):3580-3584) and have anticancer (U.S. Pat. No. 5,663,149) and antifungal activity (Pettit et al. (1998) Antimicrob. Agents Chemother. 42:2961-2965). The dolastatin or auristatin (which are pentapeptide derivatives of dolastatins) drug moiety may be attached to the antibody through the N (amino) terminus or the C (carboxyl) terminus of the peptidic drug moiety (WO 02/088172). Exemplary auristatin embodiments include the N-terminus linked monomethylauristatin drug moieties DE and DF, disclosed in "Monomethylvaline Compounds Capable of Conjugation to Ligands," U.S. Pat. No. 7,498, 298. As used herein, the abbreviation "MMAE" refers to monomethyl auristatin E. As used herein the abbreviation "MMAF" refers to dovaline-valine-dolaisoleuine-dolaproine-phenylalanine. Typically, peptide-based drug moieties can be prepared by forming a peptide bond between two or more amino acids and/or peptide fragments. Such peptide bonds can be prepared, for example, according to the liquid phase synthesis method (see E. Schroder and K. Lubke, "The Peptides," volume 1, pp 76-136, 1965, Academic Press) that is well known in the field of peptide chemistry.

Maytansinoids may be used as an active agent coupled to the antibody or fragment thereof according to the invention. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Highly cytotoxic maytansinoid drugs drugs can be prepared from ansamitocin precursors produced by fermentation of microorganisms such as Actinosynnema. Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources.

Selected examples of the calicheamicin family of antibiotics may be used as an active agent coupled to the antibody or fragment thereof according to the invention. The calicheamicin family of antibiotics is capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other antitumor agents that can be conjugated to the antibodies include BCNU, streptozoicin, vincristine and 5-fluorouracil, the family of agents known collectively LL-E33288 complex described in U.S. Pat. Nos. 5,053,394, 5,770,710, as well as esperamicins (U.S. Pat. No. 5,877,296). The present invention further contemplates an immunoconjugate formed between an antibody and a compound with nucleolytic activity (e.g., a ribonuclease or a DNA endonuclease such as a deoxyribonuclease; DNase). For selective destruction of the tumor, the antibody may comprise a highly radioactive atom.

A pharmaceutically acceptable carrier in the sense of the present invention may be any non-toxic material that does not significantly interfere in a detrimental sense with the effectiveness of the biological activity of the antibodies of the present invention. Evidently, the characteristics of the carrier will depend on the route of administration. Such a composition may contain, in addition to the active substance and carrier, diluents, fillers, salts, buffers, stabilizers, solubilizers, and other materials well known in the art. Formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

The medicament, otherwise known as a pharmaceutical composition, containing the active ingredient (antibody or antibody fragment) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated. The present invention also refers to a pharmaceutical composition for topical application, oral ingestion, inhalation, or cutaneous, subcutaneous, or intravenous injection. A skilled person is aware of the carriers and additives required for particular application forms.

When a therapeutically effective amount of the active substance (antibody or antibody fragment) of the invention is administered by intravenous, cutaneous or subcutaneous injection, the active substance may be in the form of a pyrogen-free, parenterally acceptable aqueous solution.

The invention also relates to administration of a therapeutically relevant amount of antibody as described herein in the treatment of a subject who has the medical disorders as disclosed herein. As used herein, the term "therapeutically effective amount" means the total amount of each active component of the pharmaceutical composition or method that is sufficient to show a meaningful patient benefit. The amount of active substance in the pharmaceutical composition of the present invention will depend upon the nature and severity of the condition being treated, and on the nature of prior treatments which the patient has undergone. Larger doses may be administered until the optimal therapeutic effect is obtained for the patient, and at that point the dosage is not increased further.

The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to the active substance, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The dose of the antibody administered evidently depends on numerous factors well-known in the art such as, e.g., the chemical nature and pharmaceutical formulation of the antibody, and of body weight, body surface, age and sex of the patient, as well as the time and route of administration. For an adult, the dose may exemplarily be between 0.001 µg and 1 g per day, preferably between 0.1 µg and 100 mg per day, more preferably between 1 µg and 100 mg per day, even more preferably between 5 µg and 10 mg per day. In a continuous infusion, the dose may exemplarily be between 0.01 µg and 100 mg, preferably between 1 µg and 10 mg per kilogram body mass per minute.

In another aspect of the present invention there is provided an antibody according to the invention as herein described for use in the treatment of a B-cell mediated or plasma cell mediated disease or antibody mediated disease or disorder selected from Multiple Myeloma (MM), chronic lymphocytic leukemia (CLL), Non-secretory multiple myeloma, Smoldering multiple myeloma, Monoclonal gammopathy of undetermined significance (MGUS), Solitary plasmacytoma (Bone, Extramedullar), Lymphoplasmacytic lymphoma (LPL), Waldenstrom's Macroglobulinemia, Plasma cell leukemia, Primary Amyloidosis (AL), Heavy chain disease, Systemic lupus erythematosus (SLE), POEMS syndrome/osteosclerotic myeloma, Type I and II cryoglobulinemia, Light chain deposition disease, Goodpasture's syndrome, Idiopathic thrombocytopenic purpura (ITP), Acute glomerulonephritis, Pemphigus and Pemphigoid disorders, and Epidermolysis bullosa acquisita; or any Non-Hodgkin's Lymphoma B-cell leukemia or Hodgkin's lymphoma (HL) with BCMA expression or any diseases in which patients develop neutralising antibodies to recombinant protein replacement therapy wherein said method comprises the step of administering to said patient a therapeutically effective amount of the antibody as described herein.

B-cell disorders can be divided into defects of B-cell development/immunoglobulin production (immunodeficiencies) and excessive/uncontrolled proliferation (lymphomas, leukemias). As used herein, B-cell disorder refers to both types of diseases, and methods are provided for treating B-cell disorders with an antibody.

In one aspect of the present invention the disease is Multiple Myeloma.

Use of the antibody as described herein in the manufacture of a medicament for the treatment of diseases and disorders as described herein is also provided.

For example in one aspect of the invention there is provided the use of the antibody as described herein for use in the treatment or prophylaxis of diseases and disorders responsive to modulation (such as inhibiting or blocking) of the interaction between BCMA and the ligands BAFF and APRIL.

In one embodiment of the invention the isolated antibody or antibody fragment is intended for use in the treatment of B lymphocyte cancers, such as Hodgkin's lymphoma.

In one embodiment of the invention the isolated antibody or antibody fragment is intended for use in the treatment of an autoimmune disease, such as a medical disorder associated with inflammation, preferably autoimmune disease with an inflammatory component, whereby the autoimmune disease is selected from Takayasu Arteritis, Giant-cell arteritis, familial Mediterranean fever, Kawasaki disease, Polyarteritis nodosa, cutanous Polyarteritis nodosa, Hepatitis-associated arteritis, Behcet's syndrome, Wegener's granulomatosis, Churg-Strauss syndrome, microscopic polyangiitis, Vasculitis of connective tissue diseases, Hennoch-Schönlein purpura, Cryoglobulinemic vasculitis, Cutaneous leukocytoclastic angiitis, Tropical aortitis, Sarcoidosis, Cogan's syndrome, Wiskott-Aldrich Syndrome, Lepromatous arteritis, Primary angiitis of the CNS, Thromboangiitis obliterans, Paraneoplastic ateritis, Urticaria, Dego's disease, Myelodysplastic syndrome, Eythema elevatum diutinum, Hyperimmunoglobulin D, Allergic Rhinitis, Asthma bronchiale, chronic obstructive pulmonary disease, periodontitis, Rheumatoid Arthritis, atherosclerosis, Amyloidosis, Morbus Chron, Colitis ulcerosa, Autoimmune Myositis, Diabetes mellitus, Multiple sclerosis, Guillain-Barre Syndrome, histiocytosis, Osteoarthritis, atopic dermatitis, periodontitis, chronic rhinosinusitis, Psoriasis, psoriatic arthritis, Microscopic colitis, Pulmonary fibrosis, glomerulonephritis, Whipple's disease, Still's disease, erythema nodosum, otitis, cryoglobulinemia, Sjogren's syndrome, Lupus erythematosus, aplastic anemia, Osteomyelofibrosis, chronic inflammatory demyelinating polyneuropathy, Kimura's disease, systemic sclerosis, chronic periaortitis, chronic prostatitis, idiopathic pulmonary fibrosis, chronic granulomatous disease, Idiopathic achalasia, bleomycin-induced lung inflammation, cytarabine-induced lung inflammation, Autoimmunthrombocytopenia, Autoimmunneutropenia, Autoimmunhemolytic anemia, Autoimmunlymphocytopenia, Chagas' disease, chronic autoimmune thyroiditis, autoimmune hepatitis, Hashimoto's Thyroiditis, atropic thyroiditis, Graves disease, Autoimmune polyglandular syndrome, Autoimmune Addison Syndrome, Pemphigus vulgaris, Pemphigus foliaceus, Dermatitis herpetiformis, Autoimmune alopecia, Vitiligo, Antiphospholipid syndrome, Myasthenia gravis, Stiff-man syndrome, Goodpasture's syndrome, Sympathetic ophthalmia, Folliculitis, Sharp syndrome and/or Evans syndrome, in particular hay fever, periodontitis, atherosclerosis, rheumatoid arthritis, preferably rheumatoid arthritis or multiple sclerosis.

Preferred Sequences of the Invention Pertaining to the Chimeric Antibody Sequence:

| SEQ ID No. | Sequence | Description |
|---|---|---|
| SEQ ID No. 1 | RYWMS | CDR H1 |
| SEQ ID No. 2 | EINPDSSTINYAPSLKD | CDR H2 |
| SEQ ID No. 3 | SLYYDYGDAMDYW | CDR H3 |
| SEQ ID No. 4 | KASQSVDSNVA | CDR L1 |
| SEQ ID No. 5 | SASLRFS | CDR L2 |
| SEQ ID No. 6 | QQYNNYPLTFG | CDR L3 |
| SEQ ID No. 7 | QVQLQQSGGGLVQPGGSLKLSCAAS GIDFSRYWMSWVRRAPGKGLEWIGE INPDSSTINYAPSLKDKFIISRDNA KNTLYLQMSKVRSEDTALYYCASLY YDYGDAMDYWGQGTSVTVSS | VH mouse |
| SEQ ID No. 8 | DIVMTQSQRFMTTSVGDRVSVTCKA SQSVDSNVAWYQQKPRQSPKALIFS ASLRFSGVPARFTGSGSGTDFTLTI SNLQSEDLAEYFCQQYNNYPLTFGA GTKLELKR | VL mouse |
| SEQ ID No. 9 | CAGGTGCAGCTGCAGCAGTCTGGAG GTGGCCTGGTGCAGCCTGGAGGATC CCTGAAACTCTCCTGTGCAGCCTCA GGAATCGATTTTAGTAGATACTGGA TGAGTTGGGTTCGGCGGGCTCCAGG GAAAGGACTAGAATGGATTGGAGAA ATTAATCCAGATAGCAGTACAATAA ACTATGCACCATCTCTAAAGGATAA ATTCATCATCTCCAGAGACAACGCC AAAAATACGTTGTACCTGCAAATGA GCAAAGTGAGATCTGAGGACACAGC CCTTTATTACTGTGCAAGTCTCTAC TATGATTACGGGGATGCTATGGACT ACTGGGGTCAAGGAACCTCAGTCAC CGTCTCCTCA | VH nucleotide |
| SEQ ID No. 10 | GACATTGTGATGACTCAGTCTCAAA GATTCATGACCACATCAGTAGGAGA CAGGGTCAGCGTCACCTGCAAGGCC AGTCAGAGTGTGGATAGTAATGTAG CCTGGTATCAACAGAAACCTCGGCA ATCTCCTAAAGCACTGATTTTCTCG GCATCCCTCCGGTTCAGTGGAGTCC CTGCTCGCTTCACAGGCAGTGGATC TGGGACAGATTTCACTCTCACCATC AGCAATCTGCAGTCTGAAGACTTGG | VL2 nucleotide |

Preferred Sequences of the Invention Pertaining to CD269 (BCMA):

| SEQ ID No. | Sequence | Description |
| --- | --- | --- |
| | CAGAGTATTTCTGTCAACAATATAA | |
| | CAACTATCCTCTCACGTTCGGTGCT | |
| | GGGACCAAGCTGGAGCTGAAACGT | |
| SEQ ID No. 11 | MSPILGYWKIKGLVQPTRLLL EYLEEKYEEHLYERDEGDKWR NKKFELGLEFPNLPYYIDGDV KLTQSMAIIRYIADKHNMLGG CPKERAEISMLEGAVLDIRYG VSRIAYSKDFETLKVDFLSKL PEMLKMFEDRLCHKTYLNGDH VTHPDFMLYDALDVVLYMDPM CLDAFPKLVCFKKRIEAIPQI DKYLKSSKYIAWPLQGWQATF GGGDHPPKSDLVPRGSMAGQC SQNEYFDSLLHACIPCQLRCS SNTPPLTCQRYCNASVTNSVK GTNALEHHHHHH | GST-BCMA-His |
| SEQ ID No. 12 | MAGQCSQNEYFDSLLHACIPC QLRCSSNTPPLTCQRYCNASV TNSVKGTNALE | BCMA extracellular domain |
| SEQ ID No. 13 | MLQMAGQCSQNEYFDSLLHAC IPCQLRCSSNTPPLTCQRYCN ASVTNSVKGTNALE | BCMA N-terminus sequence |
| SEQ ID No. 14 | YFDSLLHACIPCQLRCSSNT | BCMA antibody epitope-amino acids 13 to 32 of BCMA |

Preferred Sequences of the Invention Pertaining to the Humanised Antibody Sequence:

| SEQ ID No. | Sequence | Description |
| --- | --- | --- |
| SEQ ID No. 15 | DYWMS | CDR hH1 |
| SEQ ID No. 16 | EINPDSSTINYAPSLKG | CDR hH2 |
| SEQ ID No. 3 | LYYDYGDAMDYWG | CDR (h)H3 |
| SEQ ID No. 4 | KASQSVDSNVA | CDR (h)L1 |
| SEQ ID No. 17 | SDDLRFS | CDR hL2 |
| SEQ ID No. 6 | QQYNNYPLTFG | CDR (h)L3 |
| SEQ ID No. 18 | EVQLVESGGGLVQPGGSLRLSC AASGFTFDDYWMSWVRQAPGKG LEWVGEINPDSSTINYAPSLKG RFTISRDNAKNTLYLQMNSLRA EDTAVYYCASLYYDYGDAMDYW GQGTLVTVSS | hVH-0 |
| SEQ ID No. 19 | EVQLVQSGGGLVQPGGSLRLSC AASGFTFDDYWMSWVRQAPGKG LEWVGEINPDSSTINYAPSLKG RFTISRDNAKNTLYLQMNSLRA EDTAVYYCASLYYDYGDAMDYW GQGTLVTVSS | hVH-1 |
| SEQ ID No. 20 | EVQLVESGGGLVQPGGSLRLSC AASGFTFSRYWMSWVRQAPGKG LEWVGEINPDSSTINYAPSLKG RFTISRDNAKNTLYLQMNSLRA EDTAVYYCASLYYDYGDAMDYW GQGTLVTVSS | hVH-2 |
| SEQ ID No. 21 | EVQLVESGGGLVQPGGSLRLSC AASGFTFDDYWMSWVRRAPGKG LEWVGEINPDSSTINYAPSLKG RFTISRDNAKNTLYLQMNSLRA EDTAVYYCASLYYDYGDAMDYW GQGTLVTVSS | hVH-3 |
| SEQ ID No. 22 | EVQLVQSGGGLVQPGGSLRLSC AASGFTFSRYWMSWVRQAPGKG LEWVGEINPDSSTINYAPSLKG RFTISRDNAKNTLYLQMNSLRA EDTAVYYCASLYYDYGDAMDYW GQGTLVTVSS | hVH-4 |
| SEQ ID No. 23 | EVQLVQSGGGLVQPGGSLRLSC AASGFTFDDYWMSWVRRAPGKG LEWVGEINPDSSTINYAPSLKG RFTISRDNAKNTLYLQMNSLRA EDTAVYYCASLYYDYGDAMDYW GQGTLVTVSS | hVH-5 |
| SEQ ID No. 24 | EVQLVESGGGLVQPGGSLRLSC AASGFTFSRYWMSWVRRAPGKG LEWVGEINPDSSTINYAPSLKG RFTISRDNAKNTLYLQMNSLRA EDTAVYYCASLYYDYGDAMDYW GQGTLVTVSS | hVH-6 |
| SEQ ID No. 25 | EVQLVQSGGGLVQPGGSLRLSC AASGFTFSRYWMSWVRRAPGKG LEWVGEINPDSSTINYAPSLKG RFTISRDNAKNTLYLQMNSLRA EDTAVYYCASLYYDYGDAMDYW GQGTLVTVSS | hVH-7 |
| SEQ ID No. 26 | DIVMTQSPATLSVSVGDEVTLT CKASQSVDSNVAWYQQKPGQAP KLLIYSDDLRFSGVPARFSGSG SGTDFTLTISSLQSEDFAVYYC QQYNNYPLTFGAGTKLELKR | hVL-0 |
| SEQ ID No. 27 | DIVMTQSPATLSVSVGDEVTLT CKASQSVDSNVAWYQQKPGQSP KLLIYSDDLRFSGVPARFSGSG SGTDFTLTISSLQSEDFAVYYC QQYNNYPLTFGAGTKLELKR | hVL-1 |
| SEQ ID No. 28 | DIVMTQSPATLSVSVGDEVTLT CKASQSVDSNVAWYQQKPGQAP KALIYSDDLRFSGVPARFSGSG SGTDFTLTISSLQSEDFAVYYC QQYNNYPLTFGAGTKLELKR | hVL-2 |
| SEQ ID No. 29 | DIVMTQSPATLSVSVGDEVTLT CKASQSVDSNVAWYQQKPGQAP KLLIYSASLRFSGVPARFSGSG SGTDFTLTISSLQSEDFAVYYC QQYNNYPLTFGAGTKLELKR | hVL-3 |

| SEQ ID No. | Sequence | Description |
|---|---|---|
| SEQ ID No. 30 | DIVMTQSPATLSVSVGDEVTLT CKASQSVDSNVAWYQQKPGQAP KLLIYSDDLRFSGVPARFSGSG SGTDFTLTISSLQSEDFAEYYC QQYNNYPLTFGAGTKLELKR | hVL-4 |
| SEQ ID No. 31 | DIVMTQSPATLSVSVGDEVTLT CKASQSVDSNVAWYQQKPGQSP KALIYSDDLRFSGVPARFSGSG SGTDFTLTISSLQSEDFAVYYC QQYNNYPLTFGAGTKLELKR | hVL-5 |
| SEQ ID No. 32 | DIVMTQSPATLSVSVGDEVTLT CKASQSVDSNVAWYQQKPGQSP KLLIYSASLRFSGVPARFSGSG SGTDFTLTISSLQSEDFAVYYC QQYNNYPLTFGAGTKLELKR | hVL-6 |
| SEQ ID No. 33 | DIVMTQSPATLSVSVGDEVTLT CKASQSVDSNVAWYQQKPGQSP KLLIYSDDLRFSGVPARFSGSG SGTDFTLTISSLQSEDFAEYYC QQYNNYPLTFGAGTKLELKR | hVL-7 |
| SEQ ID No. 34 | DIVMTQSPATLSVSVGDEVTLT CKASQSVDSNVAWYQQKPGQAP KALIYSASLRFSGVPARFSGSG SGTDFTLTISSLQSEDFAEYYC QQYNNYPLTFGAGTKLELKR | hVL-8 |
| SEQ ID No. 35 | DIVMTQSPATLSVSVGDEVTLT CKASQSVDSNVAWYQQKPGQAP KALIYSDDLRFSGVPARFSGSG SGTDFTLTISSLQSEDFAEYYC QQYNNYPLTFGAGTKLELKR | hVL-9 |
| SEQ ID No. 36 | DIVMTQSPATLSVSVGDEVTLT CKASQSVDSNVAWYQQKPGQAP KLLIYSASLRFSGVPARFSGSG SGTDFTLTISSLQSEDFAEYYC QQYNNYPLTFGAGTKLELKR | hVL-10 |
| SEQ ID No. 37 | DIVMTQSPATLSVSVGDEVTLT CKASQSVDSNVAWYQQKPGQSP KALIYSASLRFSGVPARFSGSG SGTDFTLTISSLQSEDFAVYYC QQYNNYPLTFGAGTKLELKR | hVL-11 |
| SEQ ID No. 38 | DIVMTQSPATLSVSVGDEVTLT CKASQSVDSNVAWYQQKPGQAP KALIYSDDLRFSGVPARFSGSG SGTDFTLTISSLQSEDFAEYYC QQYNNYPLTFGAGTKLELKR | hVL-12 |
| SEQ ID No. 39 | DIVMTQSPATLSVSVGDEVTLT CKASQSVDSNVAWYQQKPGQSP KLLIYSASLRFSGVPARFSGSG SGTDFTLTISSLQSEDFAEYYC QQYNNYPLTFGAGTKLELKR | hVL-13 |
| SEQ ID No. 40 | DIVMTQSPATLSVSVGDEVTLT CKASQSVDSNVAWYQQKPGQAP KALIYSASLRFSGVPARFSGSG SGTDFTLTISSLQSEDFAEYYC QQYNNYPLTFGAGTKLELKR | hVL-14 |
| SEQ ID No. 41 | DIVMTQSPATLSVSVGDEVTLT CKASQSVDSNVAWYQQKPGQSP KALIYSASLRFSGVPARFSGSG SGTDFTLTISSLQSEDFAEYYC QQYNNYPLTFGAGTKLELKR | hVL-15 |
| SEQ ID No. 42 | DIVMTQSPATLSVSVGDEVTLT CKASQSVDSNVAWYQQKPGQAP KLLIFSDDLRFSGVPARFSGSG SGTDFTLTISSLQSEDFAVYYC QQYNNYPLTFGAGTKLELKR | hVL-16 |
| SEQ ID No. 43 | DIVMTQSPATLSVSVGDEVTLT CKASQSVDSNVAWYQQKPGQSP KLLIFSDDLRFSGVPARFSGSG SGTDFTLTISSLQSEDFAVYYC QQYNNYPLTFGAGTKLELKR | hVL-17 |
| SEQ ID No. 44 | DIVMTQSPATLSVSVGDEVTLT CKASQSVDSNVAWYQQKPGQSP KALIFSDDLRFSGVPARFSGSG SGTDFTLTISSLQSEDFAVYYC QQYNNYPLTFGAGTKLELKR | hVL-18 |
| SEQ ID No. 45 | DIVMTQSPATLSVSVGDEVTLT CKASQSVDSNVAWYQQKPGQSP KALIFSASLRFSGVPARFSGSG SGTDFTLTISSLQSEDFAVYYC QQYNNYPLTFGAGTKLELKR | hVL-19 |
| SEQ ID No. 46 | DIVMTQSPATLSVSVGDEVTLT CKASQSVDSNVAWYQQKPGQSP KALIFSASLRFSGVPARFSGSG SGTDFTLTISSLQSEDFAEYYC QQYNNYPLTFGAGTKLELKR | hVL-20 |
| SEQ ID No. 47 | DIVMTQSPATLSVSVGDEVTLT CKASQSVDSNVAWYQQKPGQSP KALIFSDDLRFSGVPARFSGSG SGTDFTLTISSLQSEDFAEYYC QQYNNYPLTFGAGTKLELKR | hVL-21 |
| SEQ ID No. 48 | DIVMTQSPATLSVSVGDEVTLT CKASQSVDSNVAWYQQKPGQSP KLLIFSASLRFSGVPARFSGSG SGTDFTLTISSLQSEDFAVYYC QQYNNYPLTFGAGTKLELKR | hVL-22 |
| SEQ ID No. 49 | DIVMTQSPATLSVSVGDEVTLT CKASQSVDSNVAWYQQKPGQSP KLLIFSDDLRFSGVPARFSGSG SGTDFTLTISSLQSEDFAEYYC QQYNNYPLTFGAGTKLELKR | hVL-23 |
| SEQ ID No. 50 | DIVMTQSPATLSVSVGDEVTLT CKASQSVDSNVAWYQQKPGQAP KALIFSASLRFSGVPARFSGSG SGTDFTLTISSLQSEDFAVYYC QQYNNYPLTFGAGTKLELKR | hVL-24 |
| SEQ ID No. 51 | DIVMTQSPATLSVSVGDEVTLT CKASQSVDSNVAWYQQKPGQAP KALIFSDDLRFSGVPARFSGSG SGTDFTLTISSLQSEDFAEYYC QQYNNYPLTFGAGTKLELKR | hVL-25 |
| SEQ ID No. 52 | DIVMTQSPATLSVSVGDEVTLT CKASQSVDSNVAWYQQKPGQAP KLLIFSASLRFSGVPARFSGSG SGTDFTLTISSLQSEDFAEYYC QQYNNYPLTFGAGTKLELKR | hVL-26 |
| SEQ ID No. 53 | DIVMTQSPATLSVSVGDEVTLT CKASQSVDSNVAWYQQKPGQSP KALIFSASLRFSGVPARFSGSG SGTDFTLTISSLQSEDFAVYYC QQYNNYPLTFGAGTKLELKR | hVL-27 |
| SEQ ID No. 54 | DIVMTQSPATLSVSVGDEVTLT CKASQSVDSNVAWYQQKPGQSP KALIFSDDLRFSGVPARFSGSG SGTDFTLTISSLQSEDFAEYYC QQYNNYPLTFGAGTKLELKR | hVL-28 |

| SEQ ID No. | Sequence | Description |
|---|---|---|
| SEQ ID No. 55 | DIVMTQSPATLSVSVGDEVTLT CKASQSVDSNVAWYQQKPGQSP KLLIFSASLRFSGVPARFSGSG SGTDFTLTISSLQSEDFAEYYC QQYNNYPLTFGAGTKLELKR | hVL-29 |
| SEQ ID No. 56 | DIVMTQSPATLSVSVGDEVTLT CKASQSVDSNVAWYQQKPGQAP KALIFSASLRFSGVPARFSGSG SGTDFTLTISSLQSEDFAEYYC QQYNNYPLTFGAGTKLELKR | hVL-30 |

Preferred Sequences of the Invention Pertaining to Unitary General Formulae for the Chimeric, Mouse and/or Humanised Sequences:

| SEQ ID No. 57 | XYWMS | CDR xH1 |
|---|---|---|
| SEQ ID No. 58 | EINPDSSTINYAPSLKX | CDR xH2 |
| SEQ ID No. 59 | SXXLRFS | CDR xL2 |
| SEQ ID No. 60 | XVQLXXSGGGLVQPGGSLXLSCA ASGXXFXXYWMSWVRXAPGKGLE WXGEINPDSSTINYAPSLKXXFX ISRDNAKNTLYLQMXXXRXEDTA XYYCASLYYDYGDAMDYWGQGTX VTVSS | xVH-General sequence formula for mouse and humanised VH sequences |
| | $X_1$VQLX$_2$X$_3$SGGGLVQPGGSLX$_4$LS CAASGX$_5$X$_6$FX$_7$X$_8$YWMSWVRX$_9$AP GKGLEWX$_{10}$GEINPDSSTINYAPS LKX$_{11}$X$_{12}$FX$_{13}$ISRDNAKNTLYLQM X$_{14}$X$_{15}$X$_{16}$RX$_{17}$EDTAX$_{18}$YYCASLY YDYGDAMDYWGQGTX$_{19}$VTVSS | xVH with numbered X residues |
| SEQ ID No. 61 | DIVMTQSXXXXXXXSVGDXVXXTC KASQSVDSNVAWYQQKPXQXPKXL IXSXXLRFSGVPARFXGSGSGTDF TLTISXLQSEDXAXYXCQQYNNYP LTFGAGTKLELKR | xVL-General sequence formula for mouse and humanised VL sequences |
| | DIVMTQSX$_1$X$_2$X$_3$X$_4$X$_5$X$_6$SVGDX$_7$V X$_8$X$_9$TCKASQSVDSNVAWYQQKPX$_{10}$ QX$_{11}$PKX$_{12}$LIX$_{13}$SX$_{14}$X$_{15}$LRFSGVP ARFX$_{16}$GSGSGTDFTLTISX$_{17}$LQSE DX$_{18}$AX$_{19}$YX$_{20}$CQQYNNYPLIFGAGT KLELKR | xVL with numbered X residues |

Preferred Sequences of the Invention Pertaining to Human Constant Domains:

| SEQ ID No. 62 | TVAAPSVFIFPPSDEQLKS GTASVVCLLNNFYPREAKV QWKVDNALQSGNSQESVTE QDSKDSTYSLSSTLTLSKA DYEKHKVYACEVTHQGLSS PVTKSFNRGEC | Ig Kappa human: Used in J22.9-xi (http://www.uniprot.org/uniprot/P01834) |
|---|---|---|
| SEQ ID No. 63 | ASTKGPSVFPLAPSSKSTS GGTAALGCLVKDYFPEPVT VSWNSGALTSGVHTFPAVL QSSGLYSLSSVVTVPSSSL GTQTYICNVNHKPSNTKVD KKVEPKSCDKTHTCPPCPA PELLGGPSVFLFPPKPKDT LMISRTPEVTCVVVDVSHE DPEVKFNWYVDGVEVHNAK TKPREEQYNSTYRVVSVLT VLHQDWLNGKEYKCKVSNK ALPAPIEKTISKAKGQPRE PQVYTLPPSRDELTKNQVS LTCLVKGFYPSDIAVEWES NGQPENNYKTTPPVLDSDG SFFLYSKLTVDKSRWQQGN VFSCSVMHEALHNHYTQKS LSLSPGK | Ig Gamma-1 human: (http://www.uniprot.org/uniprot/P01857) |
| SEQ ID No. 64 | ASTKGPSVFPLAPSSKSTS GGTAALGCLVKDYFPEPVT VSWNSGALTSGVHTFPAVL QSSGLYSLSSVVTVPSSSL GTQTYICNVNHKPSNTKVD KRVEPKSCDKTHTCPPCPA PELLGGPSVFLFPPKPKDT LMISRTPEVTCVVVDVSHE DPEVKFNWYVDGVEVHNAK TKPREEQYNSTYRVVSVLT VLHQDWLNGKEYKCKVSNK ALPAPIEKTISKAKGQPRE PQVYTLPPSREEMTKNQVS LTCLVKGFYPSDIAVEWES NGQPENNYKTTPPVLDSDG SFFLYSKLTVDKSRWQQGN VFSCSVMHEALHNHYTQKS LSLSPGK | Ig Gamma-1 human: Used in J22.9-xi |

EXAMPLES

The invention is demonstrated by way of the examples disclosed herein. The examples provided herein represent only particular embodiments of the invention and are not intended to limit the scope of the invention. The examples are to be considered as providing a further description of possible and potentially preferred embodiments that enhance the technical support of one or more non-limiting embodiments.

Binding and Blocking Characteristics of the J22.9-xi and BCMA Interaction

The novel chimeric antibody (J22.9-xi) binds to the extracellular domain of human CD269 (BCMA, TNFRSF17). This was initially ascertained by ELISA and flow cytometry on the human multiple myeloma cell line MM.1S (FIG. 1, (a) and (b)). The affinity of J22.9-xi to BCMA was determined using surface plasmon resonance (SPR). The mean Kd is 54 pM as shown in FIG. 1, c.

BCMA is known to trigger signals important for the survival of multiple myeloma and plasma cells in vivo through interaction with its ligands BAFF and/or APRIL (Mackay F et al. (2003) Annu Rev Immunol 21:231-264). An in vitro blocking assay was therefore performed with the extracellular domain of human BCMA and recombinant BAFF. The binding of J22.9-xi to BCMA clearly blocks the interaction between the receptor and its ligand BAFF. Using the isotype control antibody instead of J22.9-xi, recombinant BAFF binding to BCMA is unaffected (FIG. 1, d).

Figure 2:
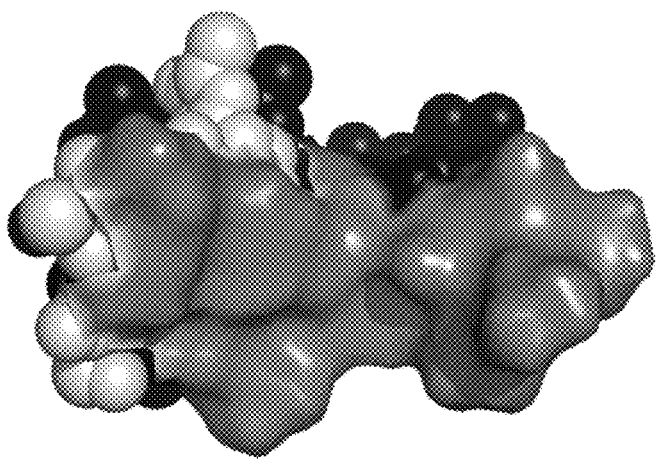
FIG. 2: The structure of CD269 (BCMA) and the J22.9-xi Fab:CD269 complex. (a) CD269 (BCMA) recognition surface. Three views of the extracellular domain of CD269 (BCMA) showing the binding epitope residues for BAFF/APRIL and J22.9-xi. At top, a view directly on the binding face of CD269 (BCMA): the light grey shading indicates all residues comprising the binding epitope of BAFF and APRIL as identified from their crystal structures, black residues (shown as spheres) do not contact either BAFF, APRIL or J22.9-xi; the subset of epitope residues involved in J22.9-xi binding are shown in surface representation; remaining light grey residues shown as spheres are part of both the BAFF and APRIL epitopes but make no direct contacts to J22.9-xi. The middle and lower panels show the same representation as in the top panel but rotated 90° toward and away from the viewer, respectively. (b) Two views of the J22.9-xi Fab:CD269 complex. J22.9-xi is shown in surface representation with the heavy chain coloured light grey and the light chain in dark grey. CD269 (BCMA) is shown in ribbon representation bound to the J22.9-xi antigen pocket. At left, full view of the Fab:CD269 complex; at right, the complex tilted toward the viewer to show the binding pocket.
Figure 2:
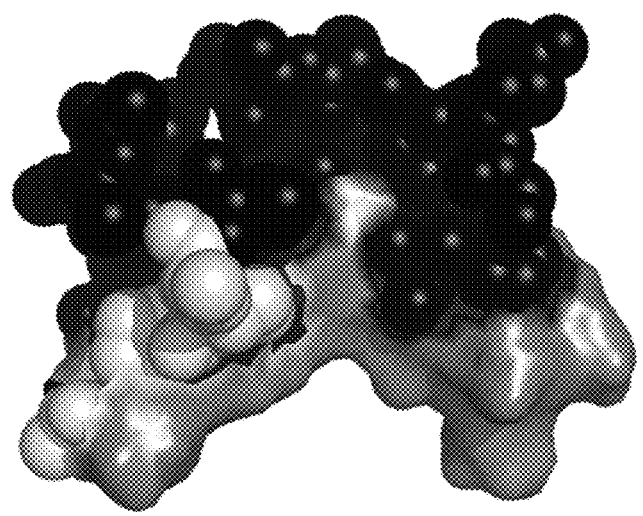
Figure 2:
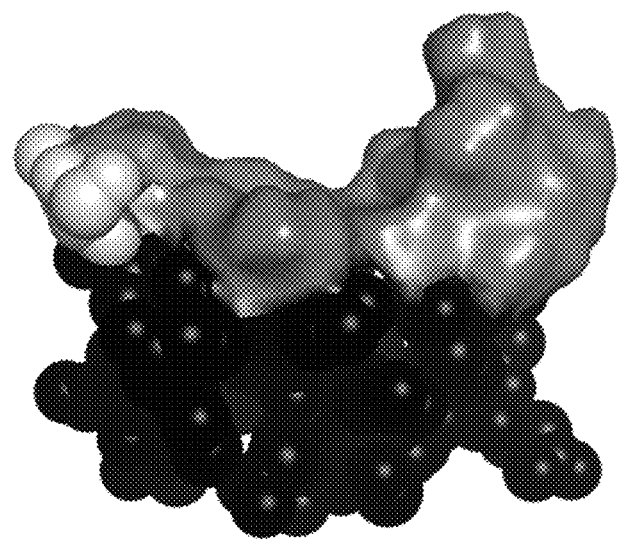
Figure 2:
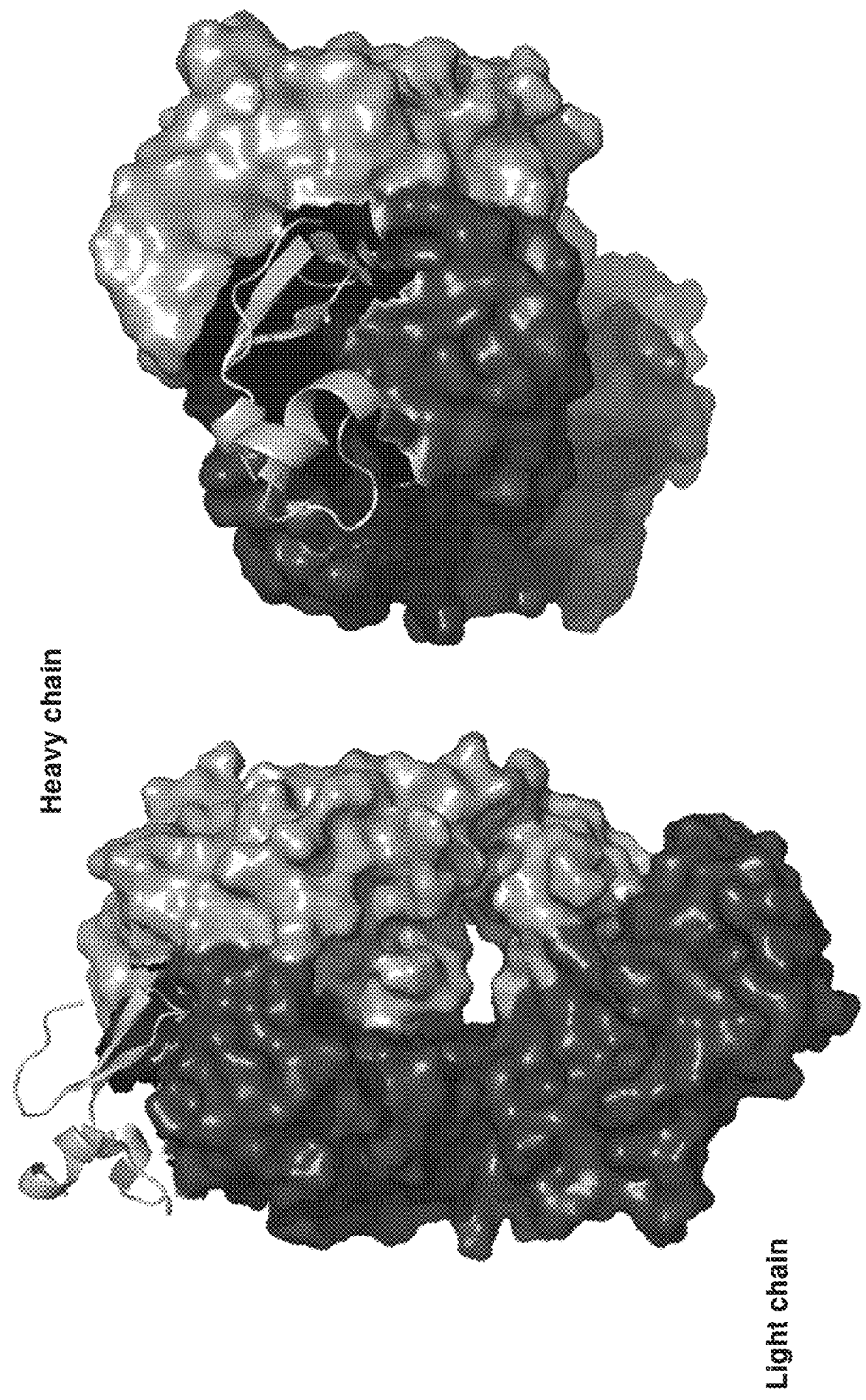

The Crystal Structure of the J22.9-xi-Fab-BCMA-complex Reveals an Extensive Binding Interface with BCMA Fab fragments prepared from J22.9-xi were crystallized in complex with the purified 46 amino acid residue BCMA extracellular domain and the complex structure solved to 1.9 angstroms resolution. High quality electron density is observable for residues 6 to 41 of BCMA and shows an extensive interaction with J22.9-xi, primarily with the light chain of the antibody (FIG. 2, B). This interface, which buries 740.4 square angstroms and involves one third of the BCMA residues, covers 12 of 16 residues of the identical epitope observed in the crystal structures of BMCA complexes with APRIL and sTALL1 (also known as BAH-), including the conserved DxL motif (Gordon N C, et al. (2003), BAFF/BlysS receptor 3 comprises a minimal TNF receptor-like module that encodes a highly focused ligand-binding site. Biochemistry 42(20): 5977-83, and Patel D R, et al. (2004), Engineering an APRIL-specific B Cell Maturation Antigen. JBC 279(16): 16727-35), providing clear rationalization of the blocking effect seen in the in vitro assays with BAFF (FIG. 2, A). The interaction with J22.9-xi additionally comprises a direct side chain contact with Ala20 and Pro23 in BCMA, residues not part of the binding epitope covered by BAFF and APRIL, and several water-mediated hydrogen bonds. The overall conformation of BCMA in all three structures is very similar, with a C-alpha rmsd of 1.4 angstroms between the J22.9-xi and APRIL complexes and 1.5 angstroms between the J22.9-xi and sTALL1 complexes; the respective C-alpha rmsds for the J22.9-xi BCMA binding epitope (residues 13-30) are 0.98 and 0.88 angstroms. Although recognizing the same BCMA epitope having the DxL motif at its core, the binding site of J22.9-xi is very different from those of sTALL1 and APRIL, as is the collection of interactions comprising the interface. As can be seen in FIG. 2, B and Table 1 and 2, 19 amino acids from J22.9-xi (6 from the heavy chain (Table 1), 13 from the light chain (Table 2)) form direct linkages to 12 residues from the extracellular domain of CD269.

TABLE 1

Amino acid interaction list between heavy chain of J22.9-xi and BCMA. These interaction lists were generated using the software PDBsum (Laskowski R A (2009)).

| Heavy chain | | CD269 |
|---|---|---|
| Trp33 | > | His19 |
| Glu50 | > | His19 |
| Leu99 | > | Leu17 |
|  | > | Leu18 |
| Tyr100 |  | Leu18 |
| Tyr101 |  | Ala20 |
|  | > | Ile22 |
|  | > | Pro23 |
| Ala106 | > | Leu18 |

TABLE 2

Amino acid interaction list between light chain of J22.9-xi and BCMA. These interaction lists were generated using the software PDBsum (Laskowski R A (2009)).

| Light chain | | CD269 |
|---|---|---|
| Ser31 | > | Arg27 |
|  |  | Thr32 |
| Ala34 | > | Leu17 |
| Tyr36 | > | Leu17 |
| Phe49 | > | Leu18 |
|  |  | Asp15 |
| Ser50 | > | Tyr13 |
|  |  | Asp15 |
|  |  | Arg27 |
| Ser52 | > | Arg27 |
| Ser67 | > | Thr32 |
| Leu53 | > | Tyr13 |
|  |  | Leu26 |
|  |  | Arg27 |
| Phe55 | > | Leu18 |
| Gln89 | > | Leu17 |
| Tyr91 | > | Asp15 |
|  |  | Ser16 |
|  |  | Leu17 |

TABLE 2-continued

Amino acid interaction list between light chain of J22.9-xi and BCMA. These interaction lists were generated using the software PDBsum (Laskowski R A (2009)).

| Light chain | | CD269 |
|---|---|---|
| Tyr94 | > | His19 |
| Leu96 | > | Leu17 |

TABLE 3

Interaction list of the residues involved in CD269:APRIL und CD269:BAFF binding (residues NOT directly contacted by J22.9 are underlined). These interaction lists were generated using the software PDBsum (Laskowski R A (2009)).

| | CD269 |
|---|---|
| APRIL | |
| Asp121 | Leu35 |
| Asp123 | Pro33 |
|  | Pro34 |
|  | Leu35 |
| Asp164 | Asn31 |
| Thr166 | Arg27 |
|  | Ser30 |
| Phe167 | Tyr13 |
|  | Leu18 |
|  | Ile22 |
|  | Leu26 |
|  | Arg27 |
|  | Asn31 |
| Thr168 | Leu18 |
|  | Leu26 |
| Met169 | Leu17 |
| Gly170 | Leu17 |
|  | His19 |
| Gln171 | Leu17 |
| Arg186 | Leu17 |
|  | Leu18 |
|  | His19 |
| Cys187 | Leu17 |
| Ile188 | Asp15 |
|  | Leu17 |
|  | Leu18 |
| Asp196 | Leu26 |
| Arg197 | Leu26 |
| Tyr199 | Leu18 |
| Pro221 | Leu17 |
|  | His19 |
| Arg222 | Asp15 |
|  | Leu17 |
|  | Arg27 |
| Asn224 | Thr32 |
| Lys226 | Asn31 |
| His232 | His19 |
| BAFF | |
| Tyr22 | Ser16 |
| Asp62 | Asn31 |
| Lys63 | Ser30 |
|  | Asn31 |
| Thr64 | Arg27 |
|  | Ser30 |
|  | Asn31 |
| Tyr65 | Tyr13 |
|  | Asp15 |
|  | Leu18 |
|  | Ile22 |
| Ala66 | Leu17 |
| Met67 | Leu17 |
| Gly68 | Leu17 |
| Arg90 | Leu17 |
|  | His19 |
| Cys91 | Leu17 |
| Ile92 | Leu17 |

TABLE 3-continued

Interaction list of the residues involved in CD269:APRIL und CD269:BAFF binding (residues NOT directly contacted by J22.9 are underlined). These interaction lists were generated using the software PDBsum (Laskowski R A (2009)).

|  | CD269 |
|---|---|
| Glu97 | Leu18 |
|  | Ser29 |
|  | Ser30 |
|  | Asn31 |
| Leu99 | Ile22 |
|  | Leu26 |
| Asn101 | Leu18 |
| Pro123 | Ser16 |
|  | Leu17 |
| Arg124 | Tyr13 |
|  | Asp15 |
|  | Leu17 |
|  | Arg27 |
| Glu125 | Arg27 |
|  | Thr25 |
|  | Pro34 |
|  | Leu35 |
| Asn126 | Thr32 |
| Asp132 | His19 |

TABLE 4

Residues of the CD269 target bound by direct contacts of J22.9, APRIL and/or BAFF. Residues of the CD269 target directly contacted only by J22.9 are underlined (20, 23). Residues of the CD269 target NOT directly contacted by J22.9 are in bold type (30, 31, 33, 34, 35 for APRIL; 25, 29, 30, 31, 34, 35 for BAFF).

J22.9: 13, 15, 16, 17, 18, 19, 20, 22, 23, 26, 27, 32
APRIL: 13, 15, 17, 18, 19, 22, 26, 27, 30, 31, 32, 33, 34, 35
BAFF: 13, 15, 16, 17, 18, 19, 22, 25, 26, 27, 29, 30, 31, 32, 34, 35

TABLE 5

Data collection and refinement statistics (molecular replacement) for the crystal structure data:

|  | J22.9-xi:BCMA |
|---|---|
| Data collection |  |
| Space group | $P2_12_12_1$ |
| Cell dimensions |  |
| a, b, c (Å) | 72.801, 110.139, 137.279 |
| α, β, γ (°) | 90, 90, 90 |
| Resolution (Å) | 1.78 (2.09) * |
| $R_{sym}$ | 16.2 (69.9) |
| I/σI | 12.8 (3.04) |
| Completeness (%) | 99.9 (99.4) |
| Redundancy | 6.7 (6.7) |
| Refinement |  |
| Resolution (Å) | 1.89 |
| No. reflections | 87918 |
| $R_{work}/R_{free}$ | 0.182/0.216 |
| Molecules per asymmetric unit | 2 heavy chains (H, A), 2 light chains (L, B), 2 BCMA (F, K) |
| No. atoms |  |
| Protein | 7160 |
| Ligand/ion | 2 BisTris/3 $Cu^{2+}$ |
| Water | 726 |
| β-factors |  |
| Protein | 22.14 |
| Ligand/ion | 37.1/35.9 |
| Water | 27.2 |

TABLE 5-continued

Data collection and refinement statistics (molecular replacement) for the crystal structure data:

|  | J22.9-xi:BCMA |
|---|---|
| R.m.s. deviations |  |
| Bond lengths (Å) | 0.013 |
| Bond angles (°) | 1.16 |

* Values in parentheses are for highest-resolution shell.

TABLE 6

J22.9 Water interactions (J22.9-xi:H2O:CD269). The data in table 6 was generated using the software LigPlot (Wallace and Laskowski, European Bioinformatics Institute).

|  | $H_2O$# | CD269 |
|---|---|---|
| Light Chain |  |  |
| Ser31 (sc) | 285 | Thr32 (sc, mc) |
|  | 285, 286 | Arg27 (sc) |
|  | 285, 286 | Ser30 (sc) |
| Ser31 (mc) | 283, 284 | Arg27 (sc) |
| Asn32 (sc) | 105 | Asp15 (sc) |
|  | 105, 284 | Arg27 (sc) |
|  | 56 | Ser16 (sc) |
| Tyr36 | 66, 93, 450 | Leu17 (mc) |
| Ser50 (sc) | 105 | Asp15 (sc) |
| Ser52 (sc) | 286 | Ser30 (sc) |
|  | 286 | Arg27 (sc) |
|  | 286, 285 | Thr32 (sc, mc) |
| Gly66 (mc) | 287 | Thr32 (sc) |
|  | 285, 286 | Arg27 (sc) |
|  | 285, 286 | Ser30 (sc) |
| Gln89 (sc) | 66, 93, 450 | Leu17 (mc) |
| Tyr91 (mc) | 282 | Ser16 (sc) |
|  | 282, 281 | Ser16 (mc) |
| Tyr94 (sc) | 281 | Ser16 (mc) |
|  | 281, 282 | Ser16 (sc) |
| Heavy Chain |  |  |
| Trp33 (mc) | 42, 280 | Leu17 (mc) |
|  | 183, 279, 26 | Leu18 (mc) |
| Ser35 (sc) | 42, 66, 93, 280, 450 | Leu17 (mc) |
| Trp47 (sc) | 93, 450 | Leu17 (mc) |
| Glu50 (sc) | 281 | Ser16 (mc) |
|  | 281, 282 | Ser16 (sc) |
|  | 450 | Leu17 (mc) |
|  | 450, 280 | Leu17 (mc) |
| Leu99 (mc) | 280 | Leu17 (mc) |
| Tyr101 (mc) | 26 | Leu18 (mc) |

(sc = side chain H-bond; mc = main chain H-bond)

Strong Cytotoxic Efficacy of J22.9-xi is Strongly Decreased After Deglycosylation A luciferase-based cytotoxicity assay was established using the luciferase transduced MM.1S-Luc cell line. In this assay, bioluminescence is only detected from living cells since luciferase released by dead cells is unable to function due to the lack of ATP in the medium. PBMCs from healthy donors were isolated and mixed with MM.1S-Luc cells in a ratio of 20 to 1. After 4 hours the bioluminescence was measured.

Figure 3:
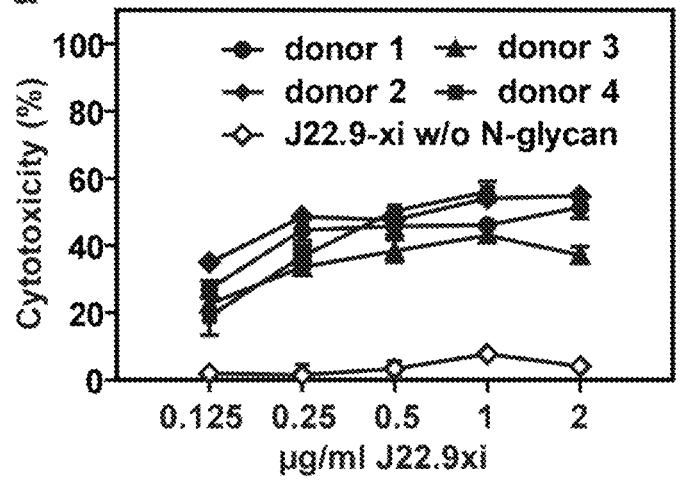
FIG. 3: In vitro cytotoxicity of J22.9-xi. (a) CD269-positive MM.1S-Luc cells mixed with human PBMCs at an effector to target ratio of 20:1 were incubated with the indicated concentrations of J22.9-xi for 4 hours. Open symbols indicate cytotoxic activity of J22.9-xi without —N-glycans when incubated with PBMCs from donor 1 and 2. Error bars indicate SEM. (b) Deglycosylation does not affect J22.9-xi binding to MM.1S cells. (c) Storage of J22.9-xi for 3 weeks at 4° C. or −80° C. does not affect cytotoxicity.
Figure 3:
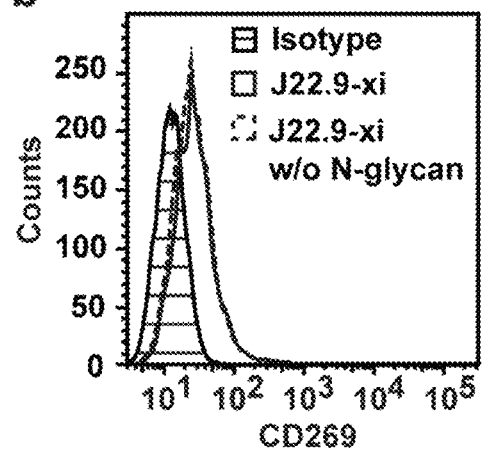
Figure 3:
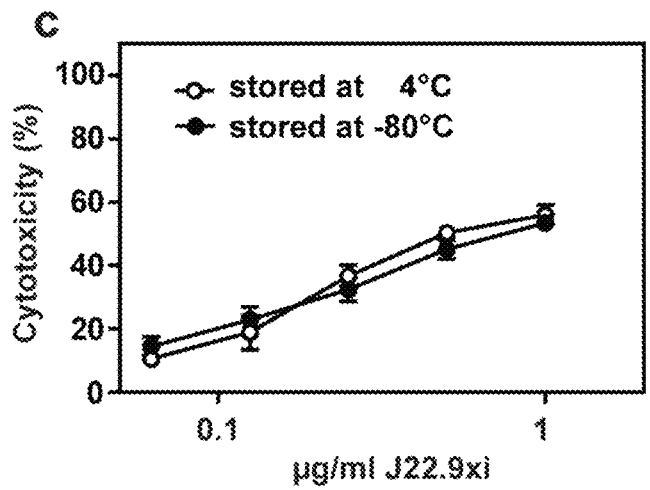

With a selection of 4 unstimulated donor PBMC preparations, the in vitro cytotoxicity of J22.9-xi was determined. The cytotoxic potential varies slightly between PBMCs from different donors. Within 4 hours of incubation, cell lysis reached 18 to 35% at a concentration of 125 ng/ml J22.9-xi. Increasing the J22.9-xi concentration to 1 ug/ml increased cell lysis up to 56% (FIG. 3, a).

After deglycosylation of J22.9-xi (J22.9-xi-N-glycan) with PNGase F, the cytotoxic activity dropped to below 8%, whereas the binding of J22.9-xi-N-glycan to BCMA-positive MM.1S cells remained unaltered (FIG. 3, (a) and (b)).

J22.9-xi Reduces Tumor Burden in Xenografted Mice and Prolongs Survival

Figure 4:
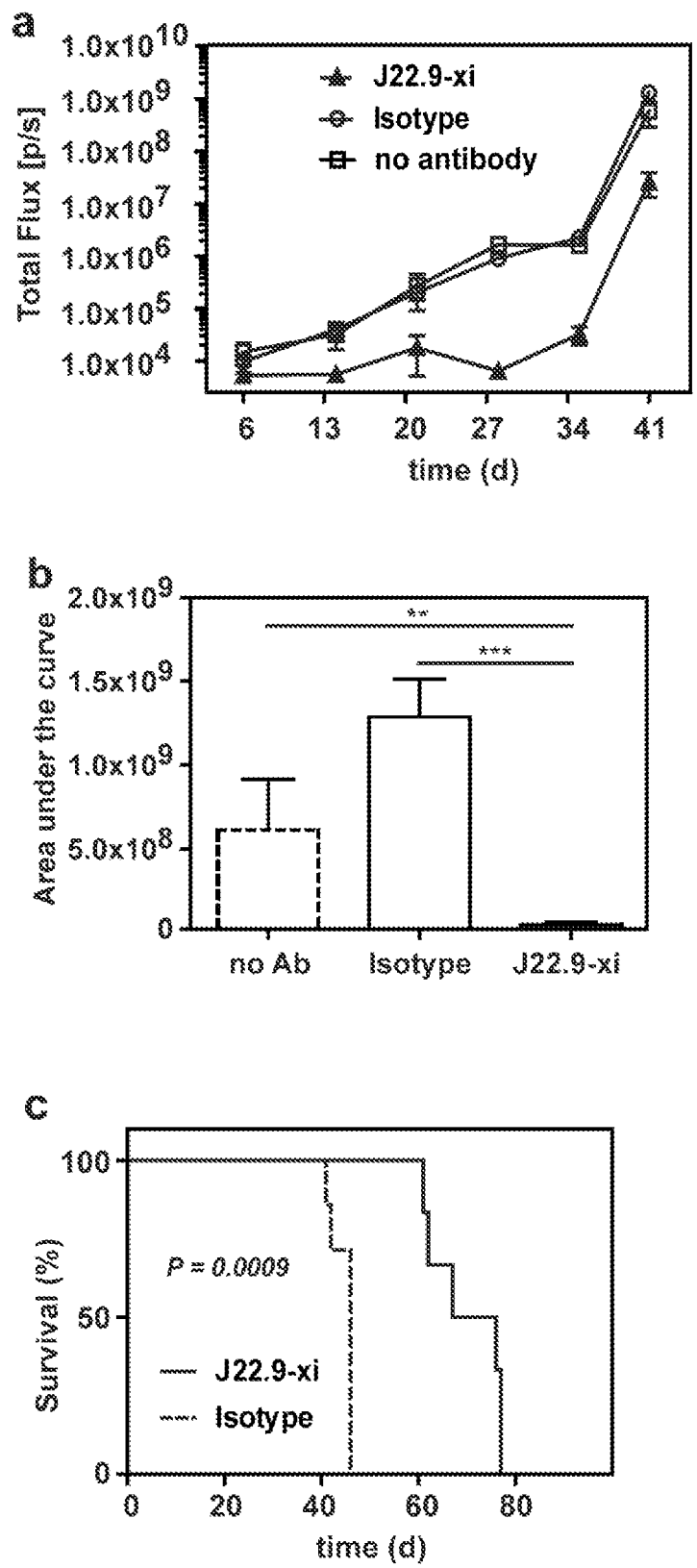
FIG. 4: Efficacy of J22.9-xi in xenografted NSG mice. (a) Tumor development over time with administration of 200 μg of J22.9-xi or the control antibody twice a week, and untreated control mice. (b) Total tumor burden between day 6 and 41 (Area under the curve (AUC) of (a)). Plotted are the mean values with SEM ($P<0.01$, $*P<0.001$, t-test). (c) Overall survival of J22.9-xi and isotype control mice. The P value was calculated using the Log-rank (Mantel-Cox) Test. (d-1) Detection of MM.1S-Luc cells in the indicated groups without administration of therapeutic antibody. Below the rightmost image the numbers (41, 41, 44, 40) indicate the days post-tumor cell injection on which the specific mouse died. (d-2) Detection of MM.1S-Luc cells in the indicated groups at day 21 and 28. Dorsal view. (e) Relationship between J22.9-xi concentration and tumor development. (f) Total tumor load between day 6 and 42 (AUC of (e)). Mean values with SEM ($P<0.01$, $*P<0.001$, t-test). (g) Overview of experimental time line.
Figure 4:
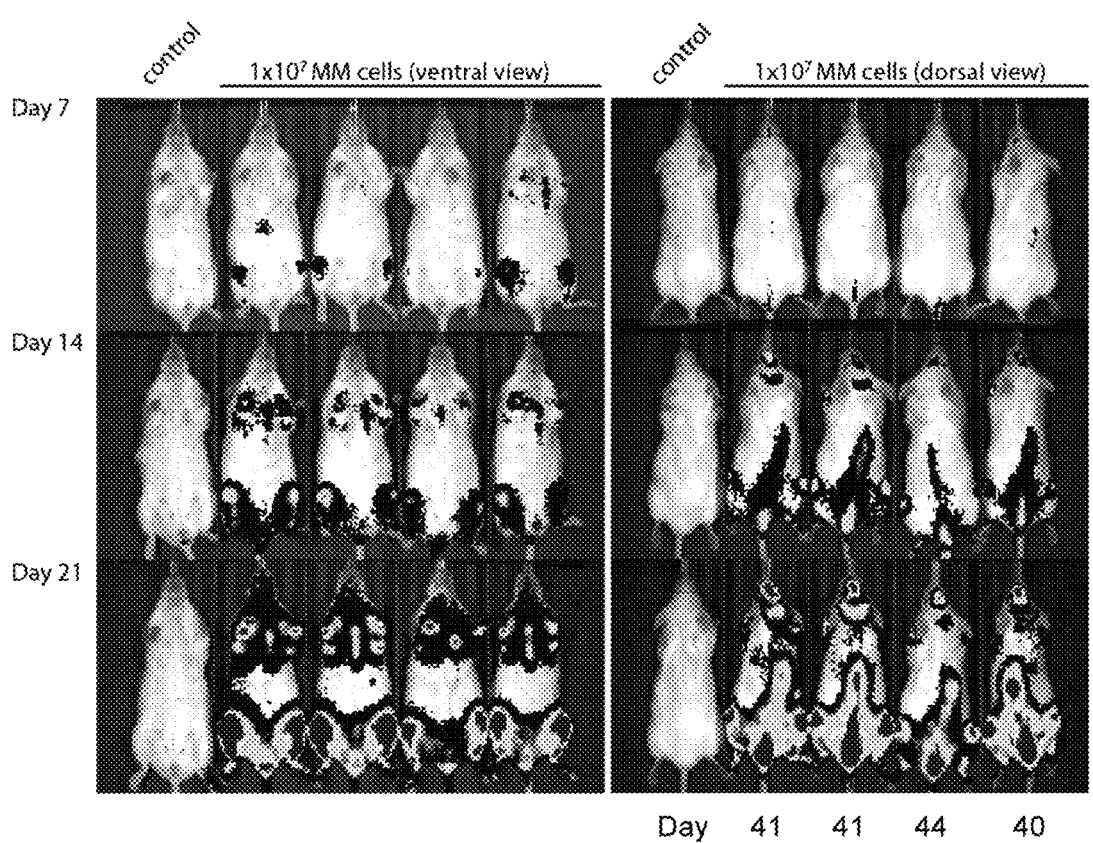
Figure 4:
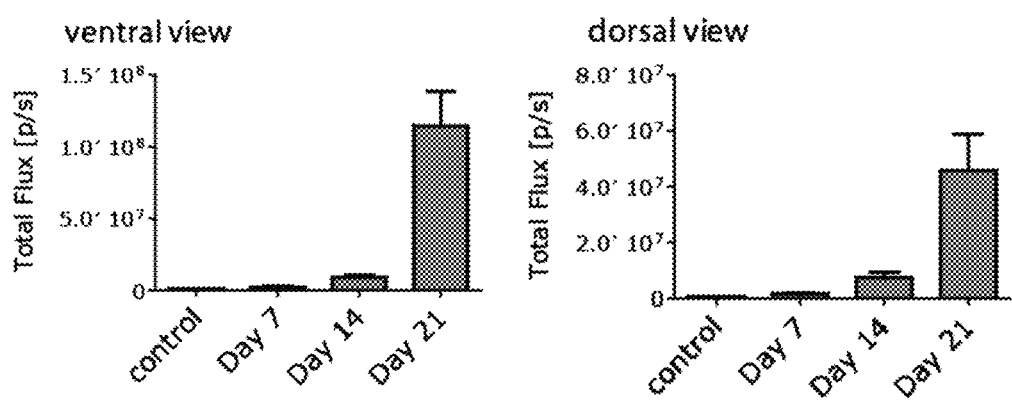
Figure 4:
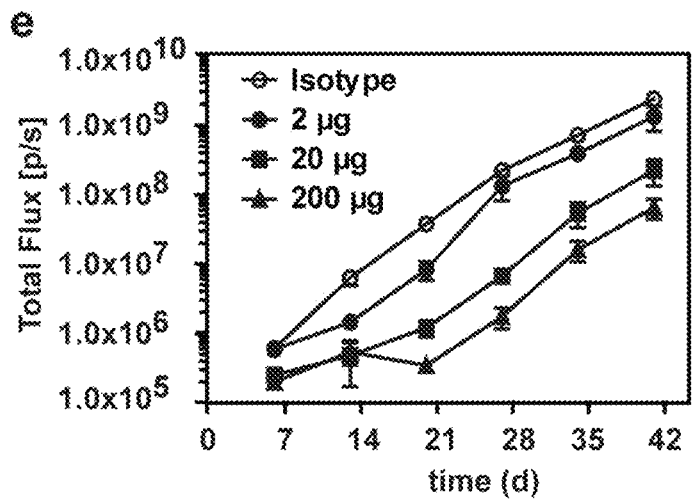
Figure 4:
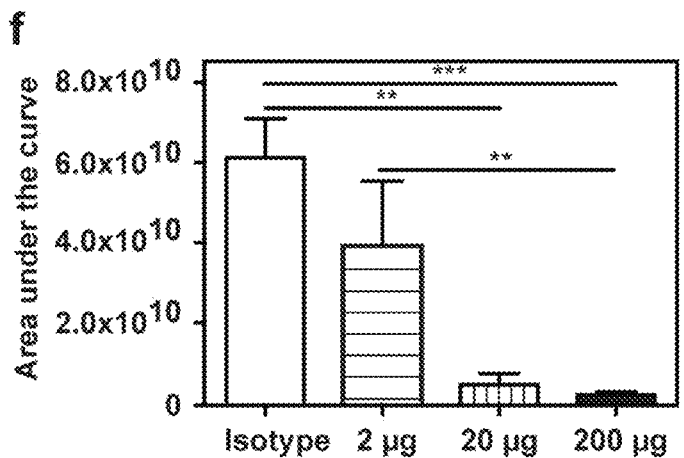
Figure 4:
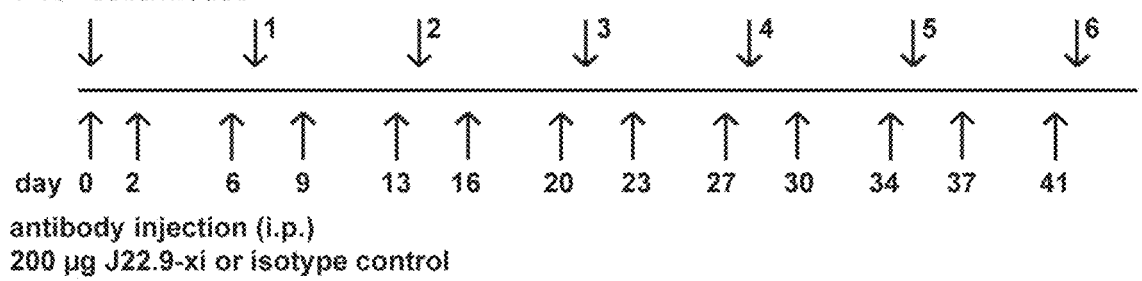

We used NOD scid common gamma chain knock out (NSG) mice lacking functional B, T and NK cell populations. These mice, injected with 1*10$^7$ MM.1S-Luc cells intravenously, develop hind limb paralysis within 6 weeks (FIG. 4, d-1). The day on which the first symptom appears, defines the day of killing.

After injection of 1×10$^7$ MM.1S-Luc in the tail vein, the mice were divided randomly into 3 groups. The first group (n=2) received no treatment until the end of the experiment, whereas the second (n=5) and the third (n=6) group received twice weekly injections of 200 µg of an isotype control or the J22.9-xi antibody, respectively. The antibodies were administered for a period of 6 weeks intraperitoneally (i.p.) starting with the day of tumor cell injection. Tumor growth was monitored once a week using the IVIS Spectrum. Bioluminescence was measured 3 minutes after i.p. injection of luciferin.

A similar course of tumor development was seen in both the untreated group and the group receiving the control antibody, whereas the group treated with J22.9-xi showed significantly less tumor burden, already beginning at the first measurement point at day six (FIG. 4, a). In addition, this group showed a smaller overall tumor load during the whole monitoring period (FIG. 4, b). Isotype control treated animals had a median survival of 46 days after cell injection. Mice receiving J22.9-xi lived an average of 26 days longer. This corresponds to an extended survival of 55% compared with mice receiving the control antibody (FIG. 4, c). Massive infiltrations of tumor cells into the spine and inguinal lymph nodes were seen in non-treated mice and in mice receiving the isotype control antibody by day 28 after cell injection (FIG. 4, d-2).

Administration of 200 µg of an antibody to a mouse corresponds to approximately 10 mg/kg bodyweight. To test the efficacy of J22.9-xi at lower doses we divided MM.1S-Luc-xenografted mice into four groups. The first group (n=7) received 200 µg of the control antibody twice weekly, and groups 2, 3 (each n=3) and 4 (n=9) were injected with 2 µg, 20 µg or 200 µg twice a week, respectively. Injection and monitoring were performed as described above.

Although tumors developed as expected in the control group mice, dramatically restricted tumor growth was observed in the groups receiving 20 µg or 200 µg of J22.9-xi (FIG. 4, (e) and (f). An overview of the experimental timeline is provided in FIG. 4, g.

Growth of Established Tumors Arrests for 5 Weeks During J22.9-xi Treatment

Figure 5:
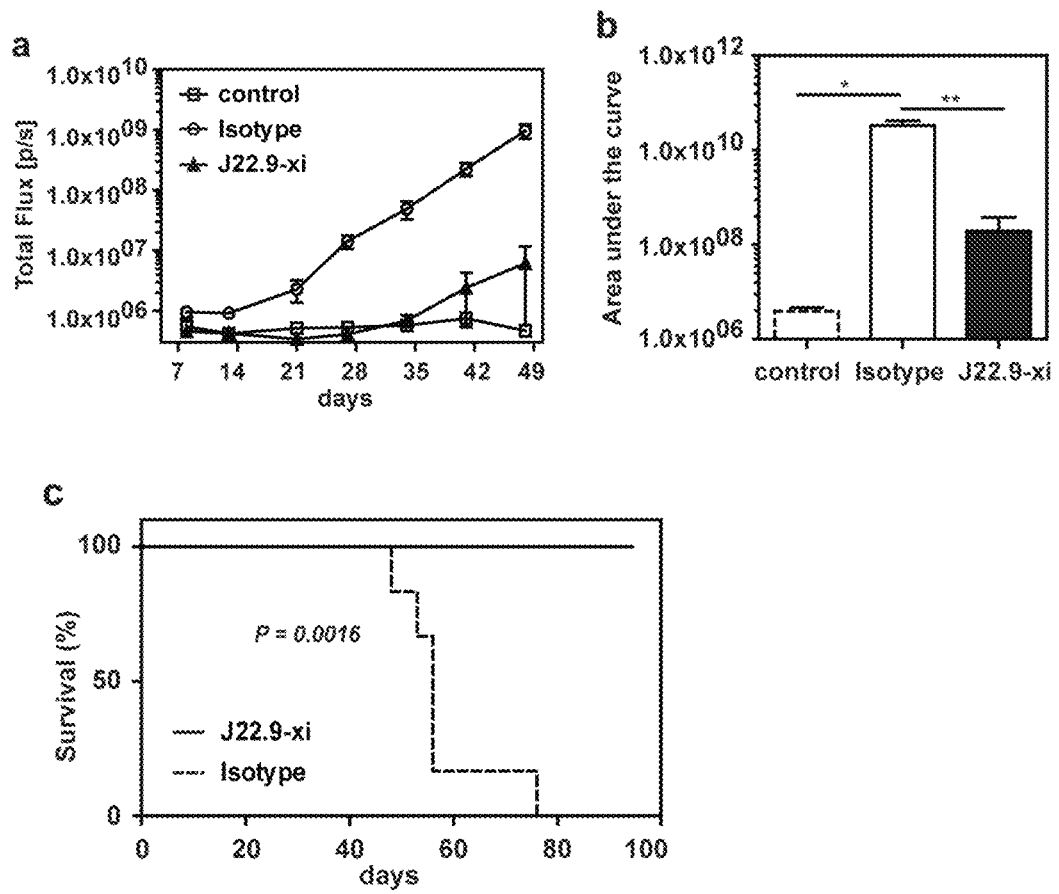
FIG. 5: Treatment of established tumors. (a) Tumor development over time with administration of 200 μg of J22.9-xi or control antibody twice weekly, and untreated control mice. (b) Total tumor load between day 8 and 48 (AUC of (a)). Plotted are the mean values with SEM ($*P<0.05$, $**P<0.01$, t-test). (c) Overall survival of J22.9-xi and isotype control mice. The P value was calculated using the Log-rank (Mantel-Cox) Test. An overview of the experimental time line is provided in (d).

Therapeutic administration was mimicked by delaying the start of antibody treatment to 5 days after tumor cell injection. The xenografted mice were divided into 2 groups (n=6). The animals received 200 µg per injection of either the isotype control or J22.9-xi antibody twice a week. The first measurement was done at day 8 post cell injection. While there is no tumor-derived bioluminescence measurable to day 35 in the group receiving J22.9-xi (n=5), a steady increase in tumor load was seen in animals receiving the isotype control antibody (n=6) (FIG. 5, (a) and (b)). Mice from the isotype control group survived an average of 56 days after the cell injection, whereas all mice receiving J22.9-xi are still alive at day 77 (FIG. 5, c). An overview of the experimental timeline is provided in FIG. 5, d.

Intensive Early Phase Treatment with J22.9-xi Prevents Tumor Growth for 7 Weeks

Figure 6:
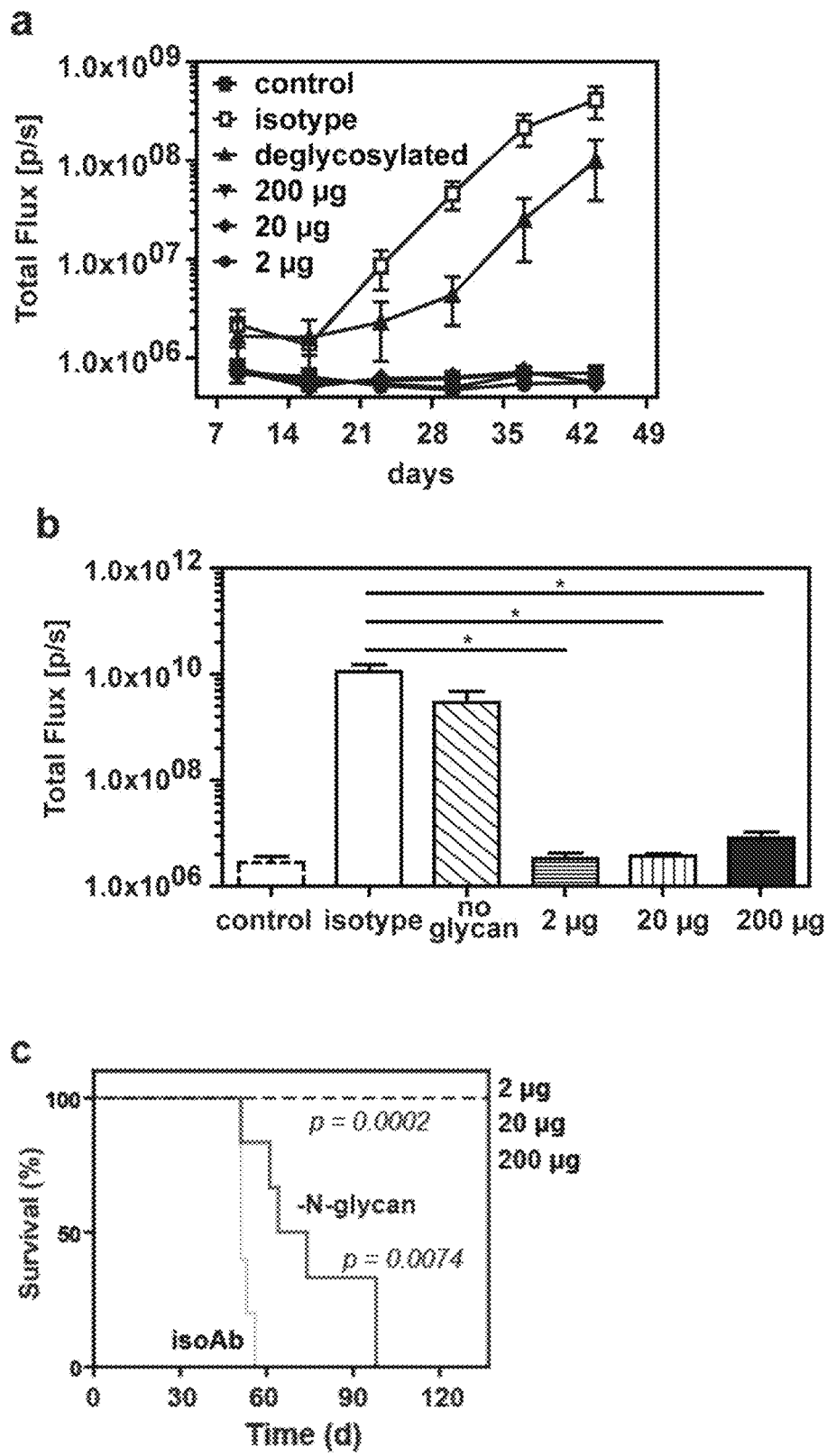
FIG. 6: Tumor treatment in the early phase of disease. (a) Course of tumor growth when treated with 2 μg, 20 μg or 200 μg of J22.9-xi or 200 μg of either the isotype control antibody or J22.9-xi without —N-glycans, and without tumor. (b) Total tumor burden within day 9 to 44 (AUC of (a)). Shown are the mean values with SEM ($*P<0.05$, $**P<0.01$, t-test). (c) Survival of antibody-treated and control xenograft SCID-Beige mice. The P values were calculated using Log-rank (Mantel-Cox) Test. An overview of the experimental time line is provided in (d).
Figure 6:
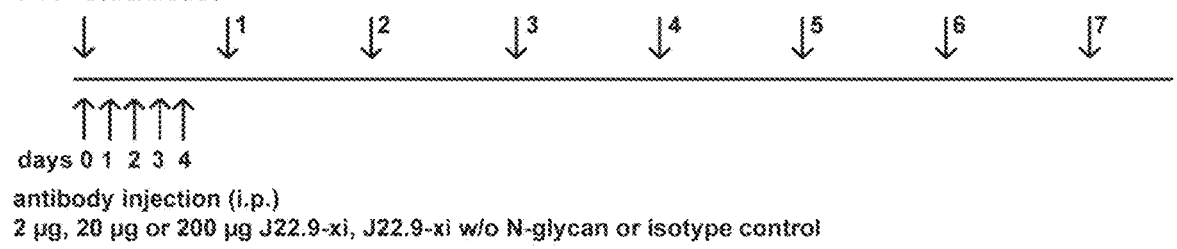
Figure 7:
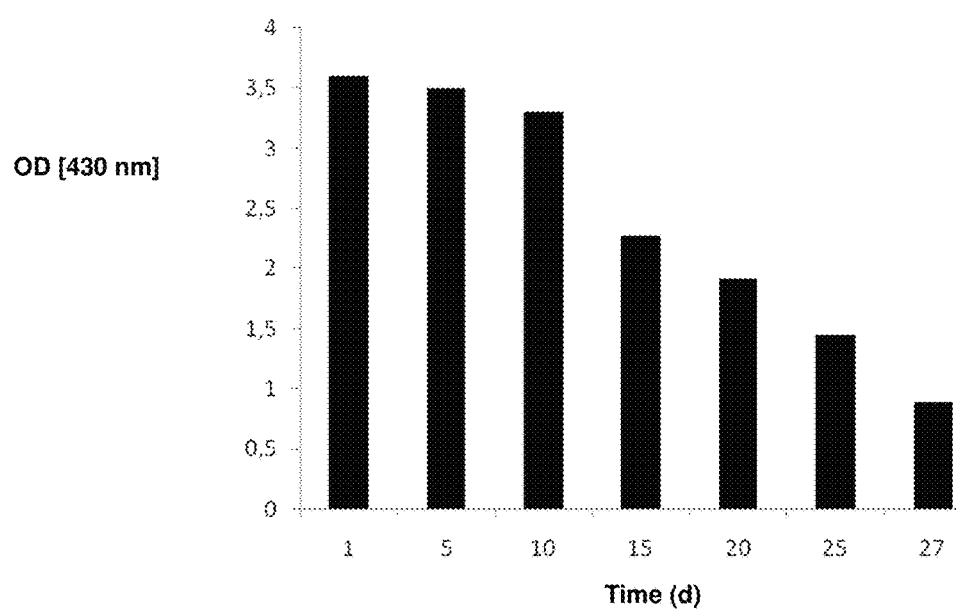
FIG. 7: Instability of hybridoma J22.9. The supernatant of hybridoma J22.9 tested positive for binding to BCMA in ELISA on BCMA-coated microtiter plates at day 1. Later analysis at indicated time points revealed a reduction of binding capacity of the supernatant. The medium was exchanged on days 7, 14 and 21.

In order to further assess the effect of treatment timing on tumor growth, different antibodies were administered for five consecutive days starting from the day of tumor cell injection. Subsequent to i.v. cell injection, the animals were divided randomly into 5 groups. Group 1 (n=5) was treated with 200 µg of the isotype control antibody per injection (i.p.), whereas group 2 (n=6) received 200 µg/injection of the J22.9-xi-N-glycan antibody. The mice from groups 3 (n=4), group 4 (n=5) and group 5 (n=5) obtained 200 µg, 20 µg and 2 µg per injection of the J22.9-xi antibody, respectively. Bioluminescence measurements began at day 9 post cell injection. Up to day 44, no tumor-derived bioluminescence was seen in any of the groups receiving the intact J22.9-xi antibody. Although the tumor growth in the animals treated with J22.9-xi-N-glycan is decelerated, the overall tumor load is not significantly different from those animals receiving the isotype control antibody (FIG. 6, (a) and (b)). Although the overall tumor load of animals treated with J22.9-xi-N-glycan (deglycosylated) was not significantly different (FIG. 6,b), the lifespan of these mice was substantially increased compared to the isoAb-treated group (FIG. 6, c). Since J22.9-xi-N-glycan was shown to be unable to induce ADCC or CDC, this result indicates that alone the binding of J22.9-xi to BCMA hinders tumor growth. It may be reasonably considered that this is due to blocking of the interaction between the receptor and its native ligands (APRIL and BAFF). An overview of the experimental timeline is provided in FIG. 6, d.

Humanisation of J22.9-xi

The J22.9-xi antibody was humanized based on sequence alignment and the data obtained from the crystal structure. The sequences of the variable regions were aligned to their respective human homologs using IgBLAST (NCBI). Each proposed mutation was evaluated by visual inspection of the structure before alteration. Binding of the mutants to BCMA can be tested using flow cytometry. The affinity is measured using surface plasmon resonance (ProteOn™ XPR36; Bio-Rad). Preliminary assessment of the binding properties of the humanised sequences shows promising results with respect to their specificity and affinity to the same epitope as described for J22.9-xi binding.

Methods

Cell Lines and Culture

The human multiple myeloma cell line MM.1S (Greenstein et al. (2003) Exp Hematol 31:271-282) was obtained from Prof. B. Dorken (MDC, Berlin, Germany). For in vivo monitoring of tumor cell growth, Luciferase and GFP were cloned into the pFU vector of the lentiviral vector system ViraPower (Invitrogen). Via GFP-expression of transduced cells, monoclonal cell lines were isolated using fluorescence-activated single cell sorting. Cell lines were cultured in RPMI-1640 medium without phenol red, containing 10% fetal calf serum, 100 units/ml of penicillin, and 100 µg/ml of streptomycin (all from PAA).

The HEK293-6E cells, purchased from the National Research Council of Canada, were maintained in Freestyle F17 medium (Invitrogen) supplemented with 7.5 mM L-Glutamine (PAA), 0.1% Pluronic F-68 (Invitrogen), and 25 µg/ml G418 (Invitrogen). Cells were grown in Erlenmeyer flasks (Corning) at 110 rpm and 37° C. in a 5% CO2 atmosphere.

Antibody Production and Purification

To obtain a BCMA-binding antibody, standard hybridoma technique was used. 4 BL/6 wild type mice were immunized 6 times with incomplete Freund's adjuvant and 30 µg of the extracellular domain of human BCMA C-terminally fused to Glutathione S-transferase (GST). After cell fusion followed by a screening period the J22.9 hybridoma was shown to secrete an anti-BCMA antibody.

Due to the instability of the hybridomas the variable regions of the light and heavy chain of hybridoma J22.9 were amplified and cloned upstream of the human kappa or the IgG1 constant domain genes, respectively. The chimeric J22.9-xi antibody was produced by transient cotransfection of 293-6E cells with a 1:2 DNA plasmid mixture encoding the light and heavy chains, respectively. In brief: 293-6E cells were resuspended to $1.7 \times 10^6$ cells/ml in serum free Freestyle F17 medium and transfected using polyethyleneimine at a final concentration of 1 µg/ml culture. Two days after transfection, cells were fed with 100% of the transfection volume Freestyle F17 medium containing 1% tryptone N1 (Organo Technie). At day 7 cells were harvested by centrifugation and the filtered (0.45 µm) culture medium was passed over a 3.5 ml Protein A Sepharose column (Bio-Rad). The column was washed with 10 ml phosphate buffered saline (PBS) and antibody eluted by addition of 20 mM sodium acetate, 150 mM NaCl, pH 3.5. Fractions of 2 ml were collected directly into tubes containing 100 µl 1 M HEPES, pH 7.5 for neutralization. The final yield of full length IgG was approximately 40 mg/l culture.

Since hybridoma J22.9 lost the capacity to produce/secrete the anti-BCMA antibody (FIG. 8), the variable regions of the heavy and light chains were amplified using PCR and subsequently cloned at the 5' end of the human constant IgG1 and K light chain genes, respectively. Through co-transfection of 293-6E cells with these two plasmids, the chimeric J22.9-xi antibody was produced. The production of the antibody of the invention was therefore inherently difficult and not achievable by straightforward routine methods.

The isotype control antibody composed of the J22.9-xi heavy chain and a random chimeric kappa light chain was produced in parallel with the J22.9-xi antibody. This antibody was shown by ELISA and flow cytometry to be unable to bind to BCMA.

The N-linked oligosaccharide chains at Asn297 of the heavy chain of J22.9-xi were removed enzymatically using N-Glycosidase F (PNGase F) (NEB). 10 mg of J22.9-xi were incubated with 15,000 units PNGase F in 500 µl PBS (pH 7.4) for 36 hours at 37° C. followed by buffer exchange into sterile PBS.

Determination of Binding and Blocking Capacities of J22.9-xi by Enzyme-Linked Immunosorbent Assays (ELISA)

Microtiter plates were coated with 10 µg/ml of the extracellular domain of human BCMA. Coated BCMA was detected with serial dilution of J22.9-xi and the isotype control ranging from 1 to 1000 ng. Binding of J22.9-xi or isotype control antibody to the coated BCMA was detected with horseradish peroxidase (HRP)-conjugated goat anti-human secondary antibody (Jackson ImmunoResearch, 109-035-098, dilution 1:5,000).

For the blocking experiment, 1 mg/ml of human recombinant BAFF fused to a His-tag (Biomol) was applied after the antibodies and washing and detected using the mouse anti-His tag (AbD Serotec, AD1.1.10, dilution 1:5,000, HRP-conjugated) antibody. All ELISAs were developed using BD OptEIA reagents A and B (BD Bioscience) and measured with a microplate spectrophotometer (BioTek) at 450 nm and 570 nm.

Flow Cytometry Analysis

For cell surface antigen detection experiments, self-made antibodies (J22.9-xi and the isotype control) and commercially available mouse anti-His tag (AbD Serotec, AD1.1.10, dilution 1:100, Alexa Fluor 488-conjugated) and goat anti-human IgG1 (Jackson ImmunoResearch, 109-116-098, dilution 1:400, PE-conjugated) antibodies and human recombinant BAFF fused to a His-tag (Biomol) were used. Experiments were performed on a FACSCalibur or a FACSCanto II flow cytometer (BD Bioscience). The data were analysed with Flowjo software version 7.6 (TreeStar Inc.).

Generation of Fab and Fab:BCMA Complexes $(Fab)_2$ fragments were generated from full length J22.9-xi IgG by incubation with pepsin. J22.9-xi was passed over a PD-10 buffer exchange column into 50 mM sodium acetate, pH 3.5 and pepsin added at 30 µg per milligram J22.9-xi. Incubation at 37° C. for 2.5 hours was sufficient to completely digest the fragment crystallizable (Fc) region and pepsin was inactivated by exchange over a PD-10 column into PBS (pH 7.2). The reduction of the $(Fab)_2$ fragments to individual Fabs was accomplished in PBS by addition of 2-Mercaptoethylamine (50 mM) in the presence of 5 mM ethylenediaminetetraacetic acid (EDTA). After incubation for 90 minutes at 37° C., the reduced cysteines were blocked by alkylation with 500 µM iodoacetamide for 30 minutes followed by buffer exchange into fresh PBS. The Fab fragments were combined with 1.5 molar equivalents of purified BCMA and the complexes isolated by size exclusion chromatography on a Superdex 75 16/60 column. Fractions were analyzed on 4-12% SDS polyacrylamide gels and fractions containing both Fab and BCMA were pooled and concentrated for crystallization trials.

Crystallization of Fab:BCMA Complexes

Concentrated complexes were supplemented with 0.5 molar equivalents of pure BCMA to ensure saturation and were subjected to crystallization screening. Initial Fab:BCMA crystallization conditions were identified from commercial screens (Qiagen) in 96-well sitting drop format plates using a Gryphon pipetting robot (200 nl drops) and optimized in 24 well plates in hanging drops (2-3 ul). The complex was concentrated to 8 mg/ml and crystallized in 21% PEG 3350, 0.1 M BisTris pH 6.5 and 5 mM $CuCl_2$ at 20° C. Crystals appeared after three days as clusters of thin plates and attained their final size (0.2-0.3 mm) within approximately 7 days. Clusters were separated and individual plates were flash frozen in liquid nitrogen in mother liquor with 20% glycerol as cryoprotectant. Complete diffraction data was collected from a single crystal at the BESSY synchrotron of the Helmoltz Zentrum Berlin. The structure was solved to a resolution of 1.9 angstroms by molecular replacement using the experimental phases from the structure of Efalizumab (3EO9) as the search model. Data processing was performed with the ccp4 suite of programs, structure refinement was performed using Phenix (Adams P D, et al. (2010), Acta Cryst. D66: 213-221) and model building and assessment using Coot. (Emsley et al, Acta Crystallographica Section D—Biological Crystallography, 2010, 66:486-501) Images were made using PyMOL (The PyMOL Molecular Graphics System, Version 1.5.0.4 Schrödinger, LLC).

In Vitro Cytotoxicity Assay

In this assay the cytotoxic effect of J22.9-xi was determined by measuring the luminescence of the remaining living cells in a bioluminescence reader. In short: freshly obtained human filter buffy coats (FBC) were back-flushed by gravity with 160 ml elution buffer (PBS (pH 7.4) containing 5 mM Na$_2$-EDTA and 2.5 [w/v] sucrose). Mononuclear cells were isolated from the eluted cells by Ficoll gradient centrifugation. Mononuclear cells from the interphases were taken and washed twice in elution buffer. After erythrocyte lysis, PBMCs were washed again, counted and adjusted by dilution in RPMI/10% FCS w/o phenol red to $1*10^7$ cells/ml. $5*10^4$ MM.1S-Luc cells in 50 µl RPMI were plated in microtiter plates. Ten minutes prior to the addition of 100 µl PBMCs, the MM.1S-Luc cells were incubated with J22.9-xi or the isotype control antibody serial dilutions in a sample volume of 200 µl. After addition of target cells, antibodies and effector cells, microtiter plates were centrifuged (300×g) for 2 minutes at room temperature (RT) and stored at 37° C. with 5% CO2. Control wells were treated with 1% Triton X instead of antibody for complete lysis. After 4 hours of incubation, 25 µl of PBS with luciferin (250 ng/ml) were applied to each well, and the bioluminescence of the living cells was measured in a bioluminescence reader (Tecan). The specific cytotoxicity was calculated according to the following formula:

100−[value (J22.9-xi)−value (total lysis)]/[value (isotype control)−value (total lysis)]*100.

In Vivo Studies

NOD.Cg-Prkdcscid Il2rgtm1Wjl Tg(CSF2)2Ygy Tg(IL3)1Ygy Tg(KITLG)3YgyJGckRolyJ mice (NSG) from The Jackson Laboratory and CB17.Cg-Prkdcscid Lystbg/Crl mice from Charles River Deutschland (Sulzfeld, Germany) were used. Experiments were performed with mice between 8-14 weeks old. All animal studies were performed according to institutional and state guidelines, under specific pathogen-free conditions. In the experimental examples relating to treatment of established tumours and tumour treatment in the early phase of disease the CB17.Cg-Prkdcscid Lystbg/Crl mice were used. The phenotype of the two mice strains mentioned herein is very similar. The animals have no functional B—, T— and NK-cells. A slightly slower tumour growth was observed in the CB17.Cg mice, indicating an even more promising effect of the therapeutic antibody of the present invention.

The xenograft model of multiple myeloma was induced by intravenous injection of $1*10^7$ MM.1S-Luc cells in the tail vein at day zero. In this model, untreated animals develop hind limb paralysis within 6 weeks. Occurrence of this symptom indicates the end point of the experiment.

For the efficacy studies, the antibodies were administered intraperitoneally (i.p.) twice a week or on 5 consecutive days starting at day zero. The J22.9-xi antibody was given in doses of 2 µg, 20 µg or 200 µg per injection; for the isotype control antibody, 200 µg/injection was used. The bioluminescence of the MM.1S-Luc cells was measured after i.p. injection of 150 µg luciferin using the IVIS Spectrum (Caliper Life Sciences). Measurements were done weekly. At each timepoint, 3 untreated control mice were also administered luciferin. Total flux values of these animals are either subtracted from each measurement or shown in the graphs.

To treat established tumors, antibody therapy was begun 5 days after injection of the MM.1S-Luc cells. 200 µg of the J22.9-xi or isotype control antibody was administered twice a week for a period of 6 weeks.

Additionally, further experimentation shows that the preferred embodiments of the invention provide surprising and unexpected effects, thereby solving the problem of the invention in a non-obvious fashion.

REFERENCES

Adams, P. D., Afonine, P. V., Bunkoczi, G., Chen, V. B., Davis, I. W., Echols, N., Headd, J. J., Hung, L. W.,
Kapral, G. J., Grosse-Kunstleve, R. W., et al. (2010). PHENIX: a comprehensive Python-based system for macromolecular structure solution. Acta Crystallogr D Biol Crystallogr 66, 213-221.

Al-Lazikani, B., Lesk, A. M., and Chothia, C. (1997). Standard conformations for the canonical structures of immunoglobulins. J Mol Biol 273, 927-948.

Anthony, R. M., and Ravetch, J. V. (2010). A novel role for the IgG Fc glycan: the anti-inflammatory activity of sialylated IgG Fcs. J Clin Immunol 30 Suppl 1, S9-14.

Arastu-Kapur, S., Anderl, J. L., Kraus, M., Parlati, F., Shenk, K. D., Lee, S. J., Muchamuel, T., Bennett, M. K., Driessen, C., Ball, A. J., et al. (2011). Nonproteasomal targets of the proteasome inhibitors bortezomib and carfilzomib: a link to clinical adverse events. Clin Cancer Res 17, 2734-2743.

Benson, M. J., Dillon, S. R., Castigli, E., Geha, R. S., Xu, S., Lam, K. P., and Noelle, R. J. (2008). Cutting edge: the dependence of plasma cells and independence of memory B cells on BAFF and APRIL. J Immunol 180, 3655-3659.

Bossen, C., and Schneider, P. (2006). BAFF, APRIL and their receptors: structure, function and signaling. Semin Immunol 18, 263-275.

Chan, A. C., and Carter, P. J. (2010). Therapeutic antibodies for autoimmunity and inflammation. Nat Rev Immunol 10, 301-316.

Chavez-Galan, L., Arenas-Del Angel, M. C., Zenteno, E., Chavez, R., and Lascurain, R. (2009). Cell death mechanisms induced by cytotoxic lymphocytes. Cell Mol Immunol 6, 15-25.

Chiu, A., Xu, W., He, B., Dillon, S. R., Gross, J. A., Sievers, E., Qiao, X., Santini, P., Hyjek, E., Lee, J. W., et al. (2007). Hodgkin lymphoma cells express TACI and BCMA receptors and generate survival and proliferation signals in response to BAFF and APRIL. Blood 109, 729-739.

D'Cruz, D. P., Khamashta, M. A., and Hughes, G. R. (2007). Systemic lupus erythematosus. Lancet 369, 587-596.

Darce, J. R., Arendt, B. K., Wu, X., and Jelinek, D. F. (2007). Regulated expression of BAFF-binding receptors during human B cell differentiation. J Immunol 179, 7276-7286.

Farge, D., Labopin, M., Tyndall, A., Fassas, A., Mancardi, G. L., Van Laar, J., Ouyang, J., Kozak, T., Moore, J., Kotter, I., et al. (2010). Autologous hematopoietic stem cell transplantation for autoimmune diseases: an observational study on 12 years' experience from the European Group for Blood and Marrow Transplantation Working Party on Autoimmune Diseases. Haematologica 95, 284-292.

Good, K. L., Avery, D. T., and Tangye, S. G. (2009). Resting human memory B cells are intrinsically programmed for enhanced survival and responsiveness to diverse stimuli compared to naive B cells. J Immunol 182, 890-901.

Gordon, N. C., Pan, B., Hymowitz, S. G., Yin, J., Kelley, R. F., Cochran, A. G., Yan, M., Dixit, V. M., Fairbrother, W. J., and Starovasnik, M. A. (2003). BAFF/BLyS receptor 3 comprises a minimal TNF receptor-like module that encodes a highly focused ligand-binding site. Biochemistry 42, 5977-5983.

Greenstein, S., Krett, N. L., Kurosawa, Y., Ma, C., Chauhan, D., Hideshima, T., Anderson, K. C., and Rosen, S. T. (2003). Characterization of the MM.1 human multiple myeloma (MM) cell lines: a model system to elucidate the characteristics, behavior, and signaling of steroid-sensitive and-resistant MM cells. Exp Hematol 31, 271-282.

Hatzoglou, A., Roussel, J., Bourgeade, M. F., Rogier, E., Madry, C., Inoue, J., Devergne, O., and Tsapis, A. (2000). TNF receptor family member BCMA (B cell maturation) associates with TNF receptor-associated factor (TRAF) 1, TRAF2, and TRAF3 and activates NF-kappa B, elk-1, c-Jun N-terminal kinase, and p38 mitogen-activated protein kinase. J Immunol 165, 1322-1330.

Jacobi, A. M., Huang, W., Wang, T., Freimuth, W., Sanz, I., Furie, R., Mackay, M., Aranow, C., Diamond, B., and Davidson, A. (2010). Effect of long-term belimumab treatment on B cells in systemic lupus erythematosus: extension of a phase II, double-blind, placebo-controlled, dose-ranging study. Arthritis Rheum 62, 201-210.

Kapoor, P., Ramakrishnan, V., and Rajkumar, S. V. (2012). Bortezomib combination therapy in multiple myeloma. Semin Hematol 49, 228-242.

Keyser, F. D. (2011). Choice of Biologic Therapy for Patients with Rheumatoid Arthritis: The Infection Perspective. Curr Rheumatol Rev 7, 77-87.

Laskowski, R. A. (2009). PDBsum new things. Nucleic Acids Res 37, D355-359.

Mackay, F., Schneider, P., Rennert, P., and Browning, J. (2003). BAFF AND APRIL: a tutorial on B cell survival. Annu Rev Immunol 21, 231-264.

Neubert, K., Meister, S., Moser, K., Weisel, F., Maseda, D., Amann, K., Wiethe, C., Winkler, T. H., Kalden, J. R., Manz, R. A., et al. (2008). The proteasome inhibitor bortezomib depletes plasma cells and protects mice with lupus-like disease from nephritis. Nat Med 14, 748-755.

Nimmerjahn, F., and Ravetch, J. V. (2008). Fcgamma receptors as regulators of immune responses. Nat Rev Immunol 8, 34-47.

Novak, A. J., Darce, J. R., Arendt, B. K., Harder, B., Henderson, K., Kindsvogel, W., Gross, J. A., Greipp, P. R., and Jelinek, D. F. (2004). Expression of BCMA, TALI, and BAFF-R in multiple myeloma: a mechanism for growth and survival. Blood 103, 689-694.

O'Connor, B. P., Raman, V. S., Erickson, L. D., Cook, W. J., Weaver, L. K., Ahonen, C., Lin, L. L., Mantchev, G. T., Bram, R. J., and Noelle, R. J. (2004). BCMA is essential for the survival of long-lived bone marrow plasma cells. J Exp Med 199, 91-98.

Queen et al., 1989; WO 90/07861

Patel, D. R., Wallweber, H. J., Yin, J., Shriver, S. K., Marsters, S. A., Gordon, N. C., Starovasnik, M. A., and Kelley, R. F. (2004). Engineering an APRIL-specific B cell maturation antigen. J Biol Chem 279, 16727-16735.

Peperzak, V., Vikstrom, I., Walker, J., Glaser, S. P., Lepage, M., Coquery, C. M., Erickson, L. D., Fairfax, K., Mackay, F., Strasser, A., et al. (2013). Mcl-1 is essential for the survival of plasma cells. Nat Immunol doi:10.1038/ni.2527.

Presta, L. G. (2008). Molecular engineering and design of therapeutic antibodies. Curr Opin Immunol 20, 460-470.

Raab, M. S., Podar, K., Breitkreutz, I., Richardson, P. G., and Anderson, K. C. (2009). Multiple myeloma. Lancet 374, 324-339.

Richardson, P. G., Hideshima, T., and Anderson, K. C. (2003). Bortezomib (PS-341): a novel, first-in-class proteasome inhibitor for the treatment of multiple myeloma and other cancers. Cancer Control 10, 361-369.

Roopenian, D. C., and Akilesh, S. (2007). FcRn: the neonatal Fc receptor comes of age. Nat Rev Immunol 7, 715-725.

Schiemann, B., Gommerman, J. L., Vora, K., Cachero, T. G., Shulga-Morskaya, S., Dobles, M., Frew, E., and Scott, M. L. (2001). An essential role for BAFF in the normal development of B cells through a BCMA-independent pathway. Science 293, 2111-2114.

Scott, D. L., Wolfe, F., and Huizinga, T. W. (2010). Rheumatoid arthritis. Lancet 376, 1094-1108.

Suzuki, K. (2013). Current therapeutic strategy for multiple myeloma. Jpn J Clin Oncol 43, 116-124.

Wang, S. Y., and Weiner, G. (2008). Complement and cellular cytotoxicity in antibody therapy of cancer. Expert Opin Biol Ther 8, 759-768.

Xu, S., and Lam, K. P. (2001). B-cell maturation protein, which binds the tumor necrosis factor family members BAFF and APRIL, is dispensable for humoral immune responses. Mol Cell Biol 21, 4067-4074.

What is claimed is:

1. A composition comprising a cell or a population thereof, wherein the cell comprises a polynucleotide encoding an antibody or a fragment thereof that binds CD269 (BCMA), and wherein the antibody or the fragment thereof comprises:

a VH domain, wherein said VH domain comprises CDR H1 comprising SEQ ID No. 1 (RYWMS) or SEQ ID No. 15 (DYWMS), CDR H2 comprising SEQ ID No. 2 (EINPDSSTINYAPSLKD) or SEQ ID No. 16 (EINPDSSTINYAPSLKG) and CDR H3 comprising SEQ ID No. 3 (SLYYDYGDAMDYW), and (ii) a VL domain, wherein said VL domain comprises CDR L1 comprising SEQ ID No. 4 (KASQSVDSNVA), CDR L2 comprising SEQ ID No. 5 (SASLRFS) or SEQ ID No. 17 (SDDLRFS) and CDR L3 comprising SEQ ID No. 6 (QQYNNYPLTFG).

2. The composition of claim 1, wherein the VL and VH domains are fused to the human Ig kappa and IgG1 constant domains, respectively.

3. The composition of claim 1, wherein the antibody or the fragment thereof comprises a VH domain comprising SEQ ID No. 7 and/or a VL domain comprising SEQ ID No. 8.

4. The composition of claim 1, wherein the antibody or the fragment thereof is chimeric, humanized, partially humanized, bi-specific or in a form of a single chain antibody or fragment thereof, or combination thereof.

5. The composition of claim 1, wherein the antibody or the fragment thereof comprises:

a VH domain comprising the sequence of one of SEQ ID No. 18 to 25, and (ii) a VL domain comprising the sequence of one of SEQ ID No. 26 to 56.

6. The composition of claim 1, wherein the antibody or the fragment thereof is glycosylated.

7. The composition of claim 6, wherein the antibody or the fragment thereof comprises a heavy chain having an N-linked oligosaccharide chain at Asn297.

8. The composition of claim 1, further comprising a pharmaceutically acceptable carrier.

9. The composition of claim 1, wherein the composition is useful for treating a medical disorder associated with B cell maturation antigen (BCMA) or the presence of pathogenic B cells.

10. The composition of claim 9, wherein the medical disorder is a cancer of plasma cells or a cancer of B lymphocytes.

11. The composition of claim 10, wherein the cancer of plasma cells is multiple myeloma, plasmacytoma, Waldenström macroglobulinemia or plasma cell leukemia; or
   wherein the cancer of B lymphocytes is Hodgkin's disease.

\* \* \* \* \*

UNITED STATES PATENT AND TRADEMARK OFFICE
CERTIFICATE OF CORRECTION

PATENT NO. : 11,667,722 B2
APPLICATION NO. : 16/923726
DATED : June 6, 2023
INVENTOR(S) : Martin Lipp It is certified that error appears in the above-identified patent and that said Letters Patent is hereby corrected as shown below:

On the Title Page

Page 2, Column 1, item (56) (Other Publications), Line 3, delete "Innumodiagnosis" and insert -- Immunodiagnostics --.

In the Specification

Column 1, Line 41-43, delete "Immunol 179:7276-7286; Benson et al. (2008) J Immunol 180:3655-3659; Good et al. (2009) J Immunol 182:890-901)." and insert the same on Column 1, Line 40, as the continuation of the same paragraph.

Column 3, Line 11, delete "cyclophosphamid" and insert -- cyclophosphamide --.

Column 6, Line 9, delete "aids" and insert -- acids --.

Column 8, Line 30 (Approx.), delete "$X_8YVVMSWVRX_9$" and insert -- $X_8YWMSWVRX_9$ --.

Column 8, Line 51 (Approx.), delete "Y WGQGTSVTVSS)," and insert -- YWGQGTSVTVSS), --.

Column 17, Line 17 (Approx.), delete "manner" and insert -- manner. --.

Column 19, Line 8, delete "103," and insert -- 103), --.

Column 19, Line 65, delete "peptabodies" and insert -- peptibodies --.

Column 21, Line 25, delete "(Al-lazikani" and insert -- (Al-Lazikani --.

Column 22, Line 5, delete "Defucolylation" and insert -- Defucosylation --.

Signed and Sealed this
Twenty-first Day of November, 2023

Katherine Kelly Vidal
*Director of the United States Patent and Trademark Office*

CERTIFICATE OF CORRECTION (continued)
U.S. Pat. No. 11,667,722 B2

Column 25, Line 32, delete "Radioimagery" and insert -- Radio Imagery --.

Column 25, Line 34, delete "4,880,935.)" and insert -- 4,880,935).) --.

Column 25, Line 62, delete "Phytolaca" and insert -- Phytolacca --.

Column 25, Line 63, delete "Momordica" and insert -- momordica --.

Column 25, Line 64, delete "Sapaonaria" and insert -- saponaria --.

Column 25, Line 65, delete "enomycin," and insert -- neomycin, --.

Column 25, Line 65, delete "tricothecenes." and insert -- trichothecenes. --.

Column 26, Line 7, delete "dolaisoleunine" and insert -- dolaisoleucine --.

Column 26, Line 16, delete "combretatstatin, chalicheamicin," and insert -- combretastatin, calicheamicin, --.

Column 26, Line 19-20, delete "cryptophysin," and insert -- cryptophycin, --.

Column 26, Line 21-22, delete "dolaisoleuine" and insert -- dolaisoleucine --.

Column 26, Line 26, delete "colcimid," and insert -- colcemid, --.

Column 26, Line 29, delete "dolostatin" and insert -- dolastatin --.

Column 25, Line 42, delete "monomethyl auristatin" and insert -- monomethylauristatin --.

Column 26, Line 47, delete "dolaisoleuine" and insert -- dolaisoleucine --.

Column 26, Line 58, delete "mitototic" and insert -- mitotic --.

Column 26, Line 64, delete "drugs drugs" and insert -- drugs --.

Column 27, Line 27, delete "streptozoicin," and insert -- streptozotocin, --.

Column 29, Line 44, delete "cutanous" and insert -- cutaneous --.

Column 29, Line 47, delete "Hennoch" and insert -- Henoch --.

Column 29, Line 52, delete "ateritis," and insert -- arteritis, --.

Column 29, Line 52, delete "Dego's" and insert -- Degos --.

Column 29, Line 53, delete "Eythema" and insert -- Erythema --.

CERTIFICATE OF CORRECTION (continued)
U.S. Pat. No. 11,667,722 B2

Column 30, Line 2-3, delete "Autoimmunthrombocytopenia," and insert
-- Autoimmunethrombocytopenia, --.

Column 30, Line 3, delete "Autoimmunneutropenia," and insert -- Autoimmuneneutropenia, --.

Column 30, Line 4, delete "Autoimmunhemolytic" and insert -- Autoimmunehemolytic --.

Column 30, Line 4-5, delete "Autoimmunlymphocytopenia," and insert
-- Autoimmunelymphocytopenia, --.

Column 30, Line 6, delete "atropic" and insert -- atrophic --.

Column 30, Line 7, delete "disase," and insert -- disease, --.

Column 35, Line 47 (Approx.), delete "YPLIFG" and insert -- YPLTFG --.

Column 36, Line 44, delete "FIG." and insert -- FIGS. --.

Column 36, Line 57-58, delete "complex" and insert -- Complex --.

Column 37, Line 2, delete "BAH-)," and insert -- BAFF), --.

Column 41, Line 2, delete "FIG." and insert -- FIGS. --.

Column 41, Line 50, delete "FIG." and insert -- FIGS. --.

Column 41, Line 63, delete "FIG." and insert -- FIGS. --.

Column 42, Line 19, delete "(FIG." and insert -- (FIGS. --.

Column 42, Line 22, delete "6,b)," and insert -- 6, b), --.

Column 42, Line 48, delete "Dorken" and insert -- Dörken --.

Column 43, Line 10 (Approx.), delete "cotransfection" and insert -- co-transfection --.

Column 43, Line 18 (Approx.), delete "(Organo Technie)." and insert -- (Organotechnie). --.

Column 44, Line 50, delete "Helmoltz" and insert -- Helmholtz --.

Column 45, Line 1, delete "Naz-EDTA" and insert -- Na$_2$-EDTA --.

Column 47, Line 37 (Approx.), delete "Fcgamma" and insert -- Fc-gamma --.

Column 47, Line 43 (Approx.), delete "TALI," and insert -- TACI, --.

Column 48, Line 6, delete "90/07861" and insert -- 90/07861. --.

In the Claims

Column 139, Line 53 (Approx.), in Claim 1, before "a VH" insert -- (i) --.

Column 140, Line 57 (Approx.), in Claim 5, before "a VH" insert -- (i) --.